(12) United States Patent
Nakano et al.

(10) Patent No.: US 8,877,779 B2
(45) Date of Patent: Nov. 4, 2014

(54) BENZIMIDAZOLE COMPOUND AND PHARMACEUTICAL USE THEREOF

(75) Inventors: Masakazu Nakano, Osaka (JP); Masanori Minoguchi, Osaka (JP); Tokushi Hanano, Osaka (JP); Shin-ichiro Ono, Osaka (JP); Hideki Horiuchi, Osaka (JP); Koji Teshima, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 631 days.

(21) Appl. No.: 12/449,874

(22) PCT Filed: Feb. 28, 2008

(86) PCT No.: PCT/JP2008/053524
§ 371 (c)(1),
(2), (4) Date: Sep. 1, 2009

(87) PCT Pub. No.: WO2008/105497
PCT Pub. Date: Sep. 4, 2008

(65) Prior Publication Data
US 2010/0120841 A1   May 13, 2010

(30) Foreign Application Priority Data

Mar. 1, 2007   (JP) ................................ 2007-051842
Mar. 8, 2007   (JP) ................................ 2007-059260
Mar. 26, 2007  (JP) ................................ 2007-078845
Mar. 30, 2007  (JP) ................................ 2007-093846

(51) Int. Cl.
*A61K 31/445*   (2006.01)
*C07D 401/04*   (2006.01)
*C07D 417/14*   (2006.01)
*C07D 405/14*   (2006.01)
*C07D 471/04*   (2006.01)

(52) U.S. Cl.
CPC ............ *C07D 401/04* (2013.01); *C07D 417/14* (2013.01); *C07D 405/14* (2013.01); *C07D 471/04* (2013.01)
USPC ............ 514/322; 514/303; 546/118; 546/199

(58) Field of Classification Search
USPC .......................... 514/322, 303; 546/199, 118
See application file for complete search history.

(56) References Cited

U.S. PATENT DOCUMENTS 6,043,366 A   3/2000   Adam et al. ................. 546/16
6,071,925 A   6/2000   Adam et al. ................ 514/278

(Continued)

FOREIGN PATENT DOCUMENTS

EP   1 491 212     12/2004
JP   10-212290     8/1998

(Continued)

OTHER PUBLICATIONS

Cai et al. "Antagonists of the orxin . . . " Expert Opin. ther. Patents 16(5) p. 631-646 (2006).*

(Continued)

*Primary Examiner* — Celia Chang
(74) *Attorney, Agent, or Firm* — Wenderoth, Lind & Ponack, L.L.P.

(57) ABSTRACT

Provided is an ORL-1 receptor agonist having improved bioavailability based on superior metabolic stability and strong and high selectivity, as compared to conventional compounds. A compound represented by the formula (I)

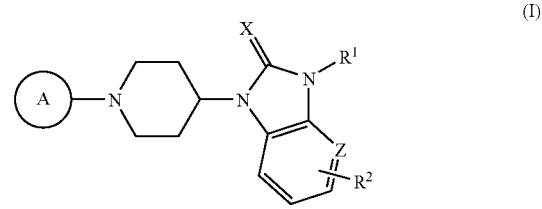

wherein each symbol is as defined in the claims.

12 Claims, 2 Drawing Sheets

(56) References Cited

U.S. PATENT DOCUMENTS

| | | | | |
|---|---|---|---|---|
| 6,075,034 | A | 6/2000 | Adam et al. | 514/278 |
| 6,258,825 | B1 | 7/2001 | Ozaki et al. | 514/322 |
| 6,262,066 | B1 * | 7/2001 | Tulshian et al. | 514/299 |
| 6,423,725 | B1 | 7/2002 | Ito et al. | 514/318 |
| 6,642,247 | B2 | 11/2003 | Adam et al. | 514/278 |
| 7,456,198 | B2 | 11/2008 | Kyle et al. | 514/322 |
| 7,566,728 | B2 * | 7/2009 | Teshima et al. | 514/322 |
| 2002/0128288 | A1 | 9/2002 | Kyle et al. | 514/322 |
| 2003/0069249 | A1 | 4/2003 | Sun et al. | 514/248 |
| 2003/0176701 | A1 | 9/2003 | Adam et al. | 546/19 |
| 2005/0070528 | A1 | 3/2005 | Den Hartog et al. | 514/221 |
| 2005/0119308 | A1 | 6/2005 | Teshima et al. | 514/322 |
| 2006/0264638 | A1 | 11/2006 | Kyle et al. | 546/199 |

FOREIGN PATENT DOCUMENTS

| | | |
|---|---|---|
| JP | 11-228575 | 8/1999 |
| JP | 2000-26466 | 1/2000 |
| WO | 98/54168 | 12/1998 |
| WO | 99/36421 | 7/1999 |
| WO | 00/06545 | 2/2000 |
| WO | 00/06546 | 2/2000 |
| WO | 01/07050 | 2/2001 |
| WO | 01/39775 | 6/2001 |
| WO | 03/082333 | 10/2003 |
| WO | 2005/028466 | 3/2005 |

OTHER PUBLICATIONS

Lang et al. "Structure activit . . . " J. Med. Chem. v.47, p. 1153-116- (2004).*
Patani et al. "Bioisoterism . . . " Chem. Rev. v. 96, p. 3147-3176 (1996).*
Smart et al. "Orexins . . . " Eur. J. Pharm. v. 440, p. 199-212 (2002).*
Smith et al. "Evidence implicating a role . . . " Neuroscience Lett. v. 341, p. 256-258 (2003).*
Taheri et al. "The role of hypcretins . . . " Ann, Rev. Neurosci. v.25, p. 283-313 (2002).*
Federal Registry "examination guidelines . . . " p. 1-34 (2011).*
Hennessy et al. "Discovery of eminopiperidine . . . " CA156:327884 (2012).*
Nakano et al. "preparation of . . . " CA149:332331 (2008).*
J. R. Bunzow et al., "Molecular Cloning and Tissue Distribution of a Putative Member of the Rat Opioid Receptor Gene Family that is not a $\mu$, $\delta$ or $\kappa$ Opioid Receptor Type", FEBS Letters, vol. 347, pp. 284-288, 1994.
C. Mollereau et al., "ORL1, A Novel Member of the Opioid Receptor Family Cloning, Functional Expression and Localization", FEBS Letters, vol. 341, pp. 33-38, 1994.
J. Meunier, "Nociceptin/Orphanin FQ and the Opioid Receptor-like ORL1 Receptor", European Journal Pharmacology, vol. 340, pp. 1-15, 1997.
J. S. Mogil et al., "The Molecular and Behavioral Pharmacology of the Orphanin FQ/Nociceptin Peptide and Receptor Family", Pharmacological Reviews, vol. 53, No. 3, pp. 381-415, 2001.
J. Meunier, et al., "Isolation and Structure of the Endogenous Agonist of Opioid Receptor-like ORL1 Receptor", Nature, vol. 377, pp. 532-535, Oct. 12, 1995.
R. K. Reinscheid et al., "Orphanin FQ: A Neuropeptide that Activates an Opioidlike G Protein-Coupled Receptor", Science, vol. 270, pp. 792-794, Nov. 3, 1995.
G. Calo et al., "Pharmacology of Nociceptin and its Receptor: A Novel Therapeutic Target", British Journal of Pharmacology, vol. 129, No. 7, pp. 1261-1283, 2000.
J. Sandin et al., "Nociceptin/Orphanin FQ Microinjected into Hippocampus Impairs Spatial Learning in Rats", European Journal of Neuroscience, vol. 9, pp. 194-197, 1997.
T. Manabe et al., "Facilitation of Long-Term Potentiation and Memory in Mice Lacking Nociceptin Receptors", Nature, vol. 394, pp. 577-581, Aug. 6, 1998.
F. Jenck et al., "Orphanin FQ Acts as an Anxiolytic to Attenuate Behavioral Responses to Stress", Proc. Natl. Acad. Sci. USA, vol. 94, pp. 14854-14858, Dec. 1997.
A. Koster et al., "Targeted Disruption of the Orphanin FQ/Nociceptin Gene Increases Stress Susceptibility and Impairs Stress Adaptation in Mice", Proc., Natl. Acad. Sci. USA, vol. 96, pp. 10444-10449, Aug. 1999.
International Search Report issued Apr. 8, 2008 in International (PCT) Application No. PCT/JP2008/053524, filed Feb. 28, 2008.
Supplementary European Search Report issued in EP Application No. 08712095.2 dated Dec. 27, 2010.
Office Action issued Sep. 11, 2012 in corresponding Japanese Application No. 2009-501298.
Palin et al., "Synthesis and evaluation of N-3 substituted phenoxylpropyl piperidine benzimidazol-2-one analogues as NOP receptor agonists with analgesic and sedative properties", *Bioorganic & Medical Chemistry*, vol. 15, 2007, pp. 1828-1847.

\* cited by examiner ptimes# BENZIMIDAZOLE COMPOUND AND PHARMACEUTICAL USE THEREOF This application is a U.S. national stage of International Application No. PCT/JP2008/053524 filed Feb. 28, 2008.

TECHNICAL FIELD

The present invention relates to an invention of a compound which is an ORL-1 receptor agonist useful in the pharmaceutical field or a salt thereof, or a medicament containing the same.

BACKGROUND ART

The ORL-1 (opioid receptor-like 1) receptor (see non-patent document 1, non-patent document 2) is a receptor found in 1994 as the fourth opioid receptor following δ, κ and μ receptors, and has about 60% homology of amino acid sequence with other opioid receptors. However, it is clearly different from other opioid receptors in that it is not bound with naloxone, which is a nonselective opioid receptor antagonist (see non-patent document 2). While ORL-1 receptor is also expressed in peripheral organs such as bowel, spleen and the like, it is widely distributed mainly in the central nervous system, and highly densely expressed particularly in the cerebral cortex, hippocampus, hypothalamus, amygdala and spinal cord (see non-patent document 3, non-patent document 4).

In 1995, endogenous ligands for ORL-1 receptors were sequentially identified by research groups in France and Switzerland, and named as nociceptin (see non-patent document 5) and orphanin FQ (see non-patent document 6). Nociceptin is reported to be a peptide consisting of 17 amino acids, which plays an important role in the central nervous functions such as learning, memory, anxiety and stress (see non-patent document 7).

To be specific, it has been reported that injection of a trace amount of nociceptin into hippocampus of rat induces a learning disorder in a water maze learning test (see non-patent document 8), and that nociceptin receptor-knockout mouse quickly acquires learning in a water maze learning test as compared to normal mouse (wild-type) and that the knockout mouse shows enhanced long term potentiation (LTP) in hippocampus as compared to normal mouse (see non-patent document 9). Hence, nociceptin is considered to suppressively act on the memory-learning function. In addition, it has been reported that administration of nociceptin to rat brain ventricle provides an antianxiety activity almost equivalent to that of diazepam in behavioral pharmacological tests such as conflict test, light/dark box test, elevated plus maze test and the like (see non-patent document 10). Furthermore, it has been reported that nociceptin-knockout mouse shows hypersensitivity to stress and impaired adaptability to stress as compared to normal mouse (see non-patent document 11). In other words, nociceptin is considered to have a physiological action that functions defensively to anxiety and stress, and an ORL-1 receptor agonist is considered to potentially show an antianxiety action based on an action mechanism completely different from that of benzodiazepine compounds.

From the foregoing, a compound having an ORL-1 receptor agonist activity is suggested to be useful for the treatment of mental disorder, neuropathy and physiological disorder, particularly, improvement of anxiety and stress disorder, melancholia, traumatic injury, loss of memory due to Alzheimer's disease or other dementia, symptom of epilepsy and convulsion, acute and/or chronic pain symptoms, relief of drug withdrawal symptoms including abstinence symptoms caused by cessation of abused drugs, alcohol abuse, control of water balance, $Na^+$ excretion, arterial blood pressure disorder, eating disorder such as obesity and anorexia, and circadian rhythm sleep disorder (see patent documents 1 to 9).

non-patent document 1: FEBS Lett. 347:284-288, 1994
non-patent document 2: FEBS Lett. 341:33-38, 1994
non-patent document 3: Eur. J. Pharmacol. 340:1-15, 1997
non-patent document 4: Pharmacol. Rev. 53:381-415, 2001
non-patent document 5: Nature 377:532-535, 1995
non-patent document 6: Science 270:792-794, 1995
non-patent document 7: Br. J. Pharmacol. 129, 1261-1283, 2000
non-patent document 8: Eur. J. Neurosci. 9, 194-197, 1997
non-patent document 9: Nature 394, 577-581, 1998-14858, 1997
non-patent document 10: Proc. Natl. Acad. Sci. USA 94, 14854-10449, 1999
non-patent document 11: Proc. Natl. Acad. Sci. USA 96, 10444
patent document 1: JP-A-2000-26466
patent document 2: JP-A-11-228575
patent document 3: JP-A-10-212290
patent document 4: WO99/36421
patent document 5: WO98/54168
patent document 6: WO01/39775
patent document 7: WO00/06545
patent document 8: WO03/082333
patent document 9: WO05/028466

DISCLOSURE OF THE INVENTION

Problems to be Solved by the Invention

The known ORL-1 receptor agonist Ro64-6198 have been reported to have bioavailability (BA) of 4% (Proc. Natl. Acad. Sci. U.S.A. 97: 4938-4943, 2000).

The present inventors have intensively studied compounds having affinity for ORL-1 receptors, particularly compounds having an agonistic action on ORL-1 receptors, and found that compounds represented by the following formula (I) or salts thereof have a strong ORL-1 receptor agonistic action, have a superior metabolic stability and are expected to show high biological availability, which resulted in the completion of the present invention.

An object of the present invention is to provide an ORL-1 receptor agonist, which is strong and has high selectivity and superior metabolic stability as compared to known compounds.

Means of Solving the Problems

Accordingly, the present invention provides the following.

[1] A compound represented by the formula (I)

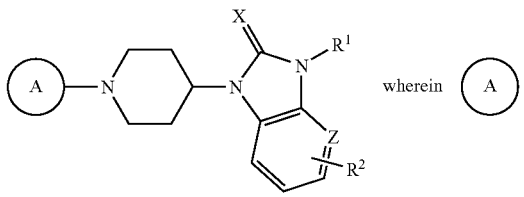

wherein (A)

is one of (a) 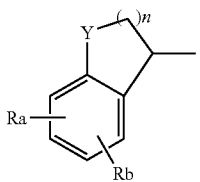

(b) 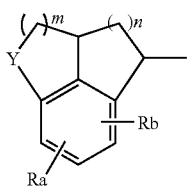

(c) 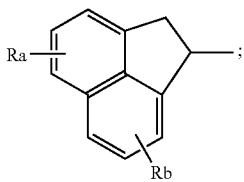

m and n are the same or different and each is an integer of 1 to 3;

$R^1$ is hydrogen,
lower alkyl,
lower alkenyl,
—C(O)-lower alkyl,
—C(O)O-lower alkyl,
—C(O)-phenyl wherein the phenyl is optionally substituted by lower alkyl, halogen, lower alkoxy, phenoxy or benzyloxy, lower alkyl-carboxyl,
lower alkyl-C(O)-phenyl wherein the phenyl is optionally substituted by lower alkyl, halogen, lower alkoxy, phenoxy or benzyloxy,
lower alkyl-C(O)O-lower alkyl,
lower alkenyl-C(O)O-lower alkyl,
lower alkyl-O-lower alkyl,
lower alkyl-C(O)—$NR^3R^4$,
—S(O)$_2$-lower alkyl,
—S(O)$_2$-phenyl wherein the phenyl is optionally substituted by lower alkyl, halogen, lower alkoxy, phenoxy or benzyloxy,
lower alkyl-S-lower alkyl,
lower alkyl-S(O)-lower alkyl,
lower alkyl-S(O)$_2$-lower alkyl,
lower alkyl-S(O)—$NR^3R^4$,
lower alkyl-$NR^3R^4$,
lower alkyl-$NR^5$—C(O)-lower alkyl,
phenyl wherein the phenyl is optionally substituted by lower alkyl, halogen, lower alkoxy, phenoxy or benzyloxy, or
benzyl wherein the phenyl is optionally substituted by lower alkyl, halogen, lower alkoxy, phenoxy or benzyloxy;

$R^3$ and $R^4$ are the same or different and each is hydrogen, lower alkyl which is optionally substituted by $C_{3-7}$ cycloalkyl, cycloalkyl or lower alkenyl, or $R^3$ and $R^4$ in combination optionally form, together with the adjacent nitrogen atom, saturated nitrogen-containing heterocycle which is optionally substituted by lower alkyl, halogen, lower alkoxy, phenoxy or benzyloxy;

$R^5$ is hydrogen, lower alkyl or lower alkenyl;

$R^2$ is hydrogen, lower alkyl, halogen, lower alkoxy, trifluoromethyl, nitro, amino or cyano;

Ra and Rb are the same or different and each is hydrogen, lower alkyl, halogen, lower alkoxy, trifluoromethyl, trifluoromethoxy, hydroxyl, nitro, amino, alkanoylamino or cyano, provided that when

is (c), either Ra or Rb is a group other than hydrogen;
X is O or S;
Y is $CH_2$, $C(CH_3)_2$, O, S, SO or $SO_2$; and
Z is CH or N, provided that when

is (b), m is 2, n is 2, Y is $CH_2$ and X is O,
then $R^1$ is a group other than hydrogen, lower alkyl, —C(O)— lower alkyl and —C(O)O-lower alkyl, or a racemic mixture thereof, or a corresponding enantiomer thereof or a pharmaceutically acceptable salt thereof.

[2] The compound of [1] wherein $R^2$ is hydrogen and X is O, or a racemic mixture thereof, or a corresponding enantiomer thereof or a pharmaceutically acceptable salt thereof.

[3] The compound of [1] wherein $R^1$ is lower alkyl-C(O)—$NR^3R^4$ (one of $R^3$ and $R^4$ is hydrogen) or lower alkyl-C(O)—$NR^3R^4$ ($R^3$ and $R^4$ in combination form, together with the adjacent nitrogen atom, saturated nitrogen-containing heterocycle which is optionally substituted by lower alkyl, halogen, lower alkoxy, phenoxy or benzyloxy), or a racemic mixture thereof, or a corresponding enantiomer thereof or a pharmaceutically acceptable salt thereof.

[4] The compound of [1] which is selected from
2-{3-[1-(1,2,3,4-tetrahydronaphthalen-1-yl)piperidin-4-yl]-2,3-dihydro-2-oxo-benzimidazol-1-yl}-N-methylacetamide,
2-{3-[1-(5-methyl-1,2,3,4-tetrahydronaphthalen-1-yl)piperidin-4-yl]-2,3-dihydro-2-oxo-benzimidazol-1-yl}-N-methylacetamide,
2-{3-[1-(5-chloro-1,2,3,4-tetrahydronaphthalen-1-yl)piperidin-4-yl]-2,3-dihydro-2-oxo-benzimidazol-1-yl}-N-methylacetamide, 2-{3-(1-indan-1-ylpiperidin-4-yl)-2,3-dihydro-2-oxo-benzimidazol-1-yl}-N-methylacetamide,
1-(4-fluoro-1-indan-1-ylpiperidin-4-yl)-1,3-dihydro-2H-benzimidazol-2-one,
2-{3-(4-methyl-1-indan-1-ylpiperidin-4-yl)-2,3-dihydro-2-oxo-benzimidazol-1-yl}-N-methylacetamide,
2-{3-(3,3-dimethyl-1-indan-1-ylpiperidin-4-yl)-2,3-dihydro-2-oxo-benzimidazol-1-yl}-N-methylacetamide,
2-{3-[1-(1,2,2a,3,4,5-hexahydroacenaphthylen-1-yl)piperidin-4-yl]-2,3-dihydro-2-oxo-benzimidazol-1-yl}-N-methylacetamide,
2-{3-[1-(2,3,3a,4,5,6-hexahydro-1H-phenalen-1-yl)piperidin-4-yl]-2,3-dihydro-2-oxo-benzimidazol-1-yl}-N-methylacetamide,
2-{3-[1-(2,3,3a,4,5,6-hexahydrobenzo[de]chromen-6-yl)piperidin-4-yl]-2,3-dihydro-2-oxo-benzimidazol-1-yl}-N-methylacetamide,
2-{3-[1-(1,2,2a,3,4,5-hexahydroacenaphthylen-5-yl)piperidin-4-yl]-2,3-dihydro-2-oxo-benzimidazol-1-yl}-N-methylacetamide,
1-[1-(6-fluoro-1,2,2a,3,4,5-hexahydroacenaphthylen-1-yl)piperidin-4-yl]-1,3-dihydro-2H-benzimidazol-2-one,
2-{3-[1-(6-fluoro-1,2,2a,3,4,5-hexahydroacenaphthylen-1-yl)piperidin-4-yl]-2,3-dihydro-2-oxo-benzimidazol-1-yl}-N-methylacetamide,
2-{3-[1-(5-fluoroacenaphthen-1-yl)piperidin-4-yl]-2,3-dihydro-2-oxo-benzimidazol-1-yl}-N-methylacetamide,
2-{3-[1-(3-chloroacenaphthen-1-yl)piperidin-4-yl]-2,3-dihydro-2-oxo-benzimidazol-1-yl}-N-methylacetamide,
2-{3-[1-(5-chloroacenaphthen-1-yl)piperidin-4-yl]-2,3-dihydro-2-oxo-benzimidazol-1-yl}-N-methylacetamide,
2-{3-[1-(8-chloroacenaphthen-1-yl)piperidin-4-yl]-2,3-dihydro-2-oxo-benzimidazol-1-yl}-N-methylacetamide,
2-{3-[1-(5-methoxyacenaphthen-1-yl)piperidin-4-yl]-2,3-dihydro-2-oxo-benzimidazol-1-yl}-N-methylacetamide,
2-{3-[1-(5-hydroxyacenaphthen-1-yl)piperidin-4-yl]-2,3-dihydro-2-oxo-benzimidazol-1-yl}-N-methylacetamide, and
2-{3-[1-(6-fluoroacenaphthen-1-yl)piperidin-4-yl]-2,3-dihydro-2-oxo-benzimidazol-1-yl}-N-methylacetamide,
or a racemic mixture thereof, or a corresponding enantiomer thereof or a pharmaceutically acceptable salt thereof.

[5] A drug for the prophylaxis and/or treatment of a disease relating to an ORL-1 receptor, comprising the compound (1) of [1], or a racemic mixture thereof, or a corresponding enantiomer thereof or a pharmaceutically acceptable salt thereof.

[6] A drug for the prophylaxis and/or treatment of a central nervous system disease relating to an ORL-1 receptor, comprising the compound (1) of [1], or a racemic mixture thereof, or a corresponding enantiomer thereof or a pharmaceutically acceptable salt thereof.

[7] A drug for the prophylaxis and/or treatment of a central nervous system disease, comprising the compound (1) of [1], or a racemic mixture thereof, or a corresponding enantiomer thereof or a pharmaceutically acceptable salt thereof.

[8] A drug for the prophylaxis and/or treatment of a sleep disorder, comprising the compound (I) of [1], or a racemic mixture thereof, or a corresponding enantiomer thereof or a pharmaceutically acceptable salt thereof.

[9] A drug for the prophylaxis and/or treatment of alcoholism, comprising the compound (I) of [1], or a racemic mixture thereof, or a corresponding enantiomer thereof or a pharmaceutically acceptable salt thereof.

[10] A drug for the prophylaxis and/or treatment of drug addiction, comprising the compound (I) of [1], or a racemic mixture thereof, or a corresponding enantiomer thereof or a pharmaceutically acceptable salt thereof.

[11] A drug for the prophylaxis and/or treatment of anxiety and stress disorder, comprising the compound (I) of [1], or a racemic mixture thereof, or a corresponding enantiomer thereof or a pharmaceutically acceptable salt thereof.

In the present specification, the pharmaceutically acceptable salt encompasses acid addition salts with inorganic acid and organic acid, and salts with inorganic bases. Moreover, the present invention also encompasses a racemic mixture of compound (I), and a corresponding enantiomer thereof.

Effect of the Invention

Compound (I) of the present invention has a superior ORL-1 receptor agonistic action, and is useful for the prophylaxis and/or treatment of diseases relating to ORL-1 receptor, for example, central nervous system diseases (e.g., anxiety and stress disorder, melancholia, traumatic injury, Alzheimer's disease, dementia, sleep disorder, drug addiction, alcoholism), acute and/or chronic pain symptom, arterial blood pressure disorder and eating disorders such as obesity and anorexia. Particularly, since the compound of the present invention is superior in the metabolic stability and expected to have high bioavailability as compared to known compounds in the prior art, it is useful as a drug substance of medicaments.

BEST MODE FOR CARRYING OUT THE INVENTION

Figure 1:
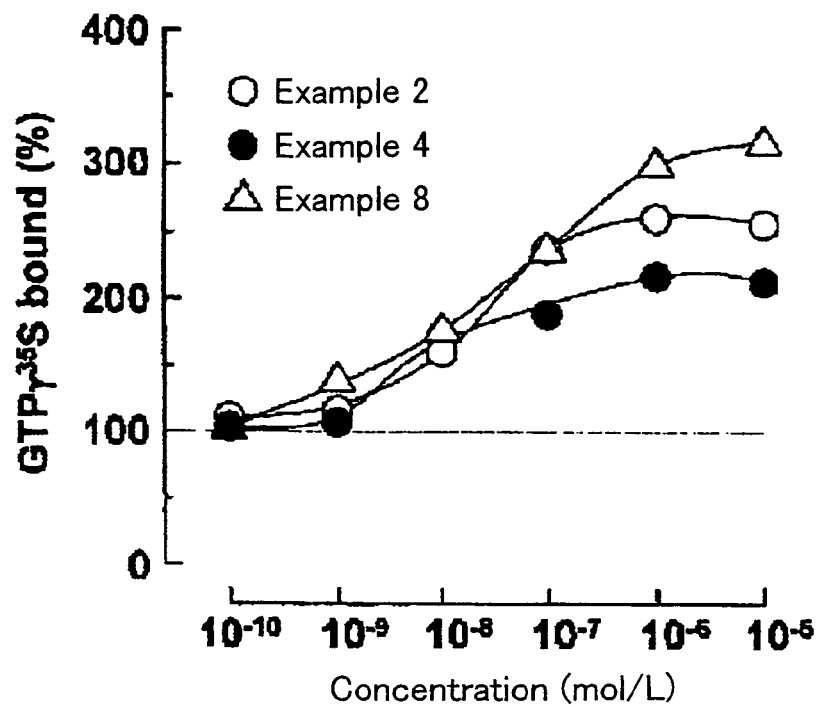
FIG. 1 shows the ORL-1 receptor agonistic activity of the compounds of Examples 2, 4 and 8.

The definition of each symbol of the formula (I) is as follows. In the present specification, the definitions apply no matter whether the term is used alone or in combination.

"Lower alkyl" means a straight or branched $C_{1-6}$ alkyl, such as methyl, ethyl, propyl, isopropyl, butyl, isobutyl, secondary butyl, tertiary butyl, pentyl, hexyl and the like, preferably a straight or branched $C_{1-4}$ alkyl, more preferably methyl, ethyl, propyl and isopropyl.

"Lower alkenyl" means straight or branched $C_{2-5}$ alkenyl, such as vinyl, 1-propenyl, 2-propenyl, isopropenyl, 1-butenyl, 2-butenyl, 3-butenyl and the like, preferably a straight or branched $C_{2-4}$ alkenyl.

"Halogen" means chlorine, iodine, fluorine or bromine, preferably chlorine, fluorine or bromine, particularly preferably fluorine.

"Lower alkoxy" means a straight or branched $C_{1-6}$ alkoxy, such as methoxy, ethoxy, propoxy, isopropoxy, butoxy, isobutoxy, secondary butoxy, tertiary butoxy, pentyloxy, hexyloxy and the like, preferably a straight or branched $C_{1-4}$ alkoxy, particularly preferably methoxy.

"Alkanoylamino" means amino having $C_{2-6}$ alkanoyl, such as acetylamino, propionylamino, butyrylamino, pentanoylamino and the like, preferably acetylamino.

"Cycloalkyl" means $C_{3-7}$ cycloalkyl, such as cyclopropyl, cyclobutyl, cyclopentyl, cyclohexyl, cycloheptyl and the like, preferably cyclopropyl.

"Saturated nitrogen-containing heterocycle formed by $R^3$ and $R^4$ in combination together with the adjacent nitrogen atom" means a 5- or 6-membered ring optionally further having 1 to 3 hetero atoms selected from nitrogen atom, oxygen atom and sulfur atom such as piperidine, pyrrolidine, morpholine, thiomorpholine, piperazine, methylpiperazine, thiazolidine, 2,4-dioxothiazolidine and the like, preferably piperazine, morpholine, pyrrolidine and 2,4-dioxothiazolidine, particularly preferably pyrrolidine and 2,4-dioxothiazolidine.

"—C(O)—" means carbonyl.

"—$NR^5$—C(O)— wherein $R^5$ is as defined in the above-mentioned formula (I)" means an amide.

"—S(O)—" means sulfinyl.

"—$S(O)_2$—" means sulfonyl.

"Pharmaceutically acceptable salt" encompasses acid addition salts with inorganic acids and organic acids such as hydrochloric acid, oxalic acid, maleic acid, fumaric acid and the like, and salts with inorganic bases such as sodium, potassium, calcium, magnesium and the like.

When the phenyl or the saturated nitrogen-containing heterocycle formed together with the adjacent nitrogen atom in the formula (I) is substituted by lower alkyl, halogen, lower alkoxy, phenoxy or benzyloxy, the number of the substituents is preferably 1 to 3.

Preferable compound is a compound of the formula (I)
wherein $R^1$ is hydrogen, —C(O)-lower alkyl, lower alkyl-carboxyl, lower alkyl-O-lower alkyl, lower alkyl-C(O)—$NR^3R^4$ or lower alkyl-$NR^3R^4$;

$R^3$ and $R^4$ are the same or different and each is hydrogen, lower alkyl which is optionally substituted by $C_{3-7}$ cycloalkyl, or cycloalkyl, or $R^3$ and $R^4$ in combination optionally form, together with the adjacent nitrogen atom, a saturated nitrogen-containing heterocycle which is optionally substituted by lower alkyl, halogen, lower alkoxy, phenoxy or benzyloxy;

$R^2$ is hydrogen or halogen;

Ra and Rb are the same or different and each is hydrogen, lower alkyl, halogen, lower alkoxy, hydroxyl, trifluoromethyl, alkanoylamino or cyano, provided that when

Ⓐ is (c), either Ra or Rb is a group other than hydrogen;

Y is $CH_2$, $C(CH_3)_2$, O, S or $SO_2$; and other symbols are as defined in the above-mentioned formula (I), provided that when

Ⓐ is (b), m is 2, n is 2, Y is $CH_2$ and X is O, $R^1$ is a group other than hydrogen and —C(O)-lower alkyl.

Particularly preferable compound is a compound of the formula (I),
wherein

Ⓐ is the following formula (a):

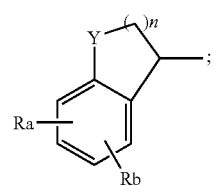

$R^1$ is hydrogen, —C(O)-lower alkyl, lower alkyl-carboxyl, lower alkyl-O-lower alkyl, lower alkyl-C(O)—$NR^3R^4$ or lower alkyl-$NR^3R^4$;

$R^3$ and $R^4$ are the same or different and each is hydrogen, lower alkyl or cycloalkyl, or $R^3$ and $R^4$ in combination optionally form, together with the adjacent nitrogen atom, saturated nitrogen-containing heterocycle which is optionally substituted by lower alkyl, halogen, lower alkoxy, phenoxy or benzyloxy;

$R^2$ is hydrogen or halogen;

Ra and Rb are the same or different and each is hydrogen, lower alkyl, halogen, lower alkoxy, hydroxyl, trifluoromethyl, alkanoylamino or cyano;

Y is $CH_2$, $C(CH_3)_2$, O, S or $SO_2$; and other symbols are as defined in the above-mentioned formula (I).

For example, the following compounds can be mentioned:
a compound selected from
2-{3-[1-(1,2,3,4-tetrahydronaphthalen-1-yl)piperidin-4-yl]-2,3-dihydro-2-oxo-benzimidazol-1-yl}-N-methylacetamide,
2-{3-[1-(5-methyl-1,2,3,4-tetrahydronaphthalen-1-yl)piperidin-4-yl]-2,3-dihydro-2-oxo-benzimidazol-1-yl}-N-methylacetamide,
2-{3-[1-(5-chloro-1,2,3,4-tetrahydronaphthalen-1-yl)piperidin-4-yl]-2,3-dihydro-2-oxo-benzimidazol-1-yl}-N-methylacetamide,
2-{3-(1-indan-1-ylpiperidin-4-yl)-2,3-dihydro-2-oxo-benzimidazol-1-yl}-N-methylacetamide,
1-(4-fluoro-1-indan-1-ylpiperidin-4-yl)-1,3-dihydro-2H-benzimidazol-2-one,
2-{3-(4-methyl-1-indan-1-ylpiperidin-4-yl)-2,3-dihydro-2-oxo-benzimidazol-1-yl}-N-methylacetamide, and
2-{3-(3,3-dimethyl-1-indan-1-ylpiperidin-4-yl)-2,3-dihydro-2-oxo-benzimidazol-1-yl}-N-methylacetamide,
or a racemic mixture thereof, or a corresponding enantiomer thereof or a pharmaceutically acceptable salt thereof.

Other particularly preferable compound is a compound of the formula (I),
wherein

Ⓐ is the following formula (b):

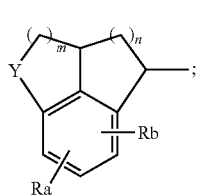

R¹ is hydrogen, —C(O)-lower alkyl, lower alkyl-C(O)—NR³R⁴ or lower alkyl-NR³R⁴;
R³ and R⁴ are the same or different and each is hydrogen, lower alkyl which is optionally substituted by $C_{3-7}$ cycloalkyl, or cycloalkyl, or R³ and R⁴ in combination optionally form, together with the adjacent nitrogen atom, saturated nitrogen-containing heterocycle which is optionally substituted by lower alkyl, halogen, lower alkoxy, phenoxy or benzyloxy;
R² is hydrogen or halogen;
Ra and Rb are the same or different and each is hydrogen, lower alkyl, halogen, lower alkoxy or hydroxyl;
X is O;
Y is $CH_2$ or O;
Z is CH; and
other symbols are as defined in the above-mentioned formula (I),
provided that when m is 2, n is 2 and Y is $CH_2$, then R¹ is a group other than hydrogen and —C(O)-lower alkyl.

For example, the following compounds can be mentioned:
a compound selected from
1-[1-(1,2,2a,3,4,5-hexahydroacenaphthylen-1-yl)piperidin-4-yl]-1,3-dihydro-2H-benzimidazol-2-one,
2-{3-[1-(1,2,2a,3,4,5-hexahydroacenaphthylen-1-yl)piperidin-4-yl]-2,3-dihydro-2-oxo-benzimidazol-1-yl}-N-methylacetamide,
2-{3-[1-(2,3,3a,4,5,6-hexahydro-1H-phenalen-1-yl)piperidin-4-yl]-2,3-dihydro-2-oxo-benzimidazol-1-yl}-N-methylacetamide,
1-[1-(2,3,3a,4,5,6-hexahydrobenzo[de]chromen-6-yl)piperidin-4-yl]-1,3-dihydro-2H-benzimidazol-2-one,
2-{3-[1-(2,3,3a,4,5,6-hexahydro-benzo[de]chromen-6-yl)piperidin-4-yl]-2,3-dihydro-2-oxo-benzimidazol-1-yl}-N-methylacetamide,
1-[1-(1,2,2a,3,4,5-hexahydroacenaphthylen-5-yl)piperidin-4-yl]-1,3-dihydro-2H-benzimidazol-2-one,
2-{3-[1-(1,2,2a,3,4,5-hexahydroacenaphthylen-5-yl)piperidin-4-yl]-2,3-dihydro-2-oxo-benzimidazol-1-yl}-N-methylacetamide,
1-[2-(cyclopropylmethylamino)ethyl]-3-[1-(1,2,2a,3,4,5-hexahydroacenaphthylen-1-yl)piperidin-4-yl]-1,3-dihydro-2H-benzimidazol-2-one,
1-[1-(1,2,2a,3,4,5-hexahydroacenaphthylen-1-yl)piperidin-4-yl]-3-(2-isopropylaminoethyl)-1,3-dihydro-2H-benzimidazol-2-one,
3-{3-{3-[1-(1,2,2a,3,4,5-hexahydroacenaphthylen-5-yl)piperidin-4-yl]-2,3-dihydro-2-oxo-benzimidazol-1-yl}propyl}thiazolidine-2,4-dione,
1-[1-(6-fluoro-1,2,2a,3,4,5-hexahydroacenaphthylen-1-yl)piperidin-4-yl]-1,3-dihydro-2H-benzimidazol-2-one, and
2-{3-[1-(6-fluoro-1,2,2a,3,4,5-hexahydroacenaphthylen-1-yl)piperidin-4-yl]-2,3-dihydro-2-oxo-benzimidazol-1-yl}-N-methylacetamide,
or a racemic mixture thereof, or a corresponding enantiomer thereof or a pharmaceutically acceptable salt thereof.

Other particularly preferable compound is a compound of the formula (I),
wherein

is the following formula (c):

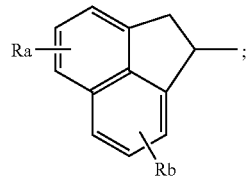

R¹ is hydrogen, —C(O)-lower alkyl or lower alkyl-C(O)—NR⁴R⁵ (one of R⁴ and R⁵ is hydrogen) or lower alkyl-C(O)—NR⁴R⁵ (R⁴ and R⁵ in combination form, together with the adjacent nitrogen atom, saturated nitrogen-containing heterocycle which is optionally substituted by lower alkyl, halogen, lower alkoxy, phenoxy or benzyloxy);
R² is hydrogen or halogen;
Ra and Rb are the same or different and each is hydrogen, lower alkyl, halogen, lower alkoxy, hydroxyl or cyano, provided one of Ra and Rb is a group other than hydrogen;
X is O; and
other symbols are as defined in the above-mentioned formula (I).

For example, the following compounds can be mentioned:
a compound selected from
2-{3-[1-(5-fluoroacenaphthen-1-yl)piperidin-4-yl]-2,3-dihydro-2-oxo-benzimidazol-1-yl}-N-methylacetamide,
2-{3-[1-(3-chloroacenaphthen-1-yl)piperidin-4-yl]-2,3-dihydro-2-oxo-benzimidazol-1-yl}-N-methylacetamide,
2-{3-[1-(5-chloroacenaphthen-1-yl)piperidin-4-yl]-2,3-dihydro-2-oxo-benzimidazol-1-yl}-N-methylacetamide,
2-{3-[1-(8-chloroacenaphthen-1-yl)piperidin-4-yl]-2,3-dihydro-2-oxo-benzimidazol-1-yl}-N-methylacetamide,
2-{3-[1-(5-methoxyacenaphthen-1-yl)piperidin-4-yl]-2,3-dihydro-2-oxo-benzimidazol-1-yl}-N-methylacetamide,
2-{3-[1-(5-hydroxyacenaphthen-1-yl)piperidin-4-yl]-2,3-dihydro-2-oxo-benzimidazol-1-yl}-N-methylacetamide, and
(R)-2-{3-[1-(6-fluoroacenaphthen-1-yl)piperidin-4-yl]-2,3-dihydro-2-oxo-benzimidazol-1-yl}-N-methylacetamide,
or a racemic mixture thereof, or a corresponding enantiomer thereof or a pharmaceutically acceptable salt thereof.

Compound of the formula (I) (unless otherwise specified, compounds of the formula (I), wherein

is one of

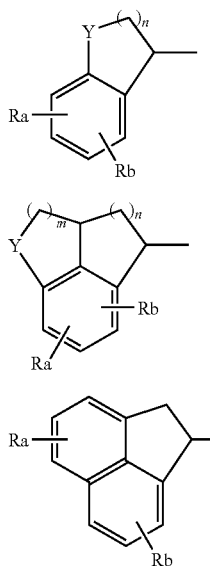

are included) can be prepared, for example, by the following methods.

Method 1

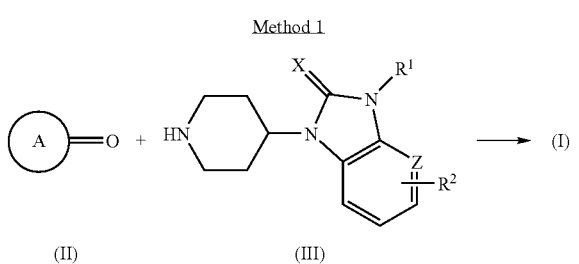

wherein each symbol is as defined in the aforementioned formula (I), provided that

is not

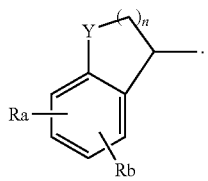

A compound of the formula (II) is reductively aminated by a compound of the formula (III) to give a compound of the formula (I). The compounds of the formula (II) and the formula (III) are known compounds, and the compound of the formula (II) can be produced by the method described in J. Chem. Soc., Perkin Trans 1, 1160, 1973, and the compound of the formula (III) can be produced by the method described in J. Med. Chem., 2001, 44, 3378 or Org. Lett., 2006, 8, 3311.

Reductive amination of a keto compound like the formula (II) using amine like the formula (III) is described in J. Org. Chem., 55, 2552-54, 1990. The reaction by this method includes a reaction of ketone and amine in a solvent such as tetrahydrofuran (THF), methanol or ethanol or a mixture of appropriate alcohol and THF in the presence of Ti(IV)-isopropoxide and sodium cyanoborohydride. The reaction temperature is about −78 to 100° C., and the reaction time is several dozen min to 2 days.

Method 2

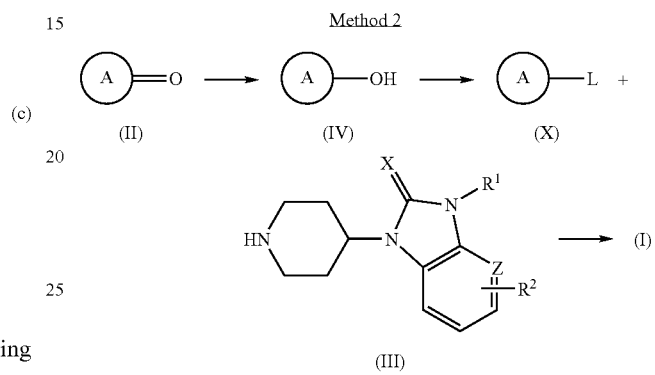

wherein L is a leaving group such as halogen, arylsulfonyloxy, alkylsulfonyloxy, arylphosphinyloxy, alkylphosphinyloxy and the like, and other symbols are as defined in the formula (I).

A compound of the formula (I) is obtained by a substitution reaction of the compound of the formula (III) and compound (X), which is induced from alcohol represented by the formula (IV), which is obtained by reducing ketone represented by the formula (II). The substitution reaction of the compound of the formula (X) and the compound of the formula (III) is performed in N,N-dimethylformamide, dimethyl sulfoxide, pyridine, dioxane, tetrahydrofuran, acetonitrile, chloroform, methylene chloride, dichloroethane, methanol, ethanol, diethyl ether etc., or a mixed solvent thereof, in the presence of an inorganic base such as potassium carbonate, potassium hydrogen carbonate, sodium carbonate, sodium hydrogen carbonate, potassium hydroxide, sodium hydroxide, sodium hydride and the like or an organic base such as triethylamine, diisopropylethylamine, pyridine, dimethylaminopyridine and the like. In addition, a catalytic amount to a small excess of sodium iodide, potassium iodide and the like may also be present. The reaction temperature is about room temperature to 200° C., and the reaction time is several min to 2 days.

Method 3

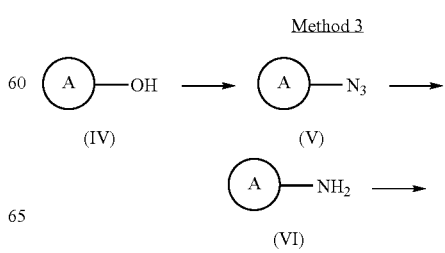

-continued

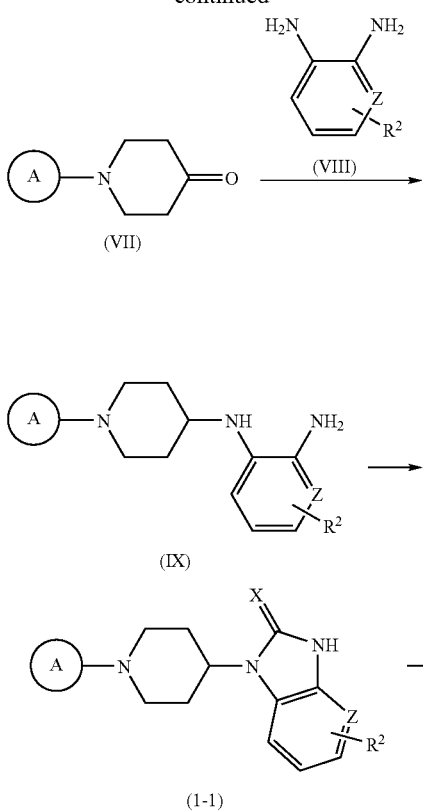

wherein each symbol is as defined in the formula (I).

The compound of the formula (VII) can be produced by the method described in WO03/082333 and using starting material (IV) as shown in the above scheme.

The compound of the formula (VII) is treated with phenylenediamine or pyridinediamine represented by the formula (VIII) to give the compound of the formula (IX), which is cyclized to give the compound of the formula (I-1) wherein $R^1$ is hydrogen.

Reductive amination of the keto compound of the formula (VII) with phenylenediamine or pyridinediamine of the formula (VIII) is performed in N,N-dimethylformamide, dimethyl sulfoxide, pyridine, dioxane, tetrahydrofuran, acetonitrile, chloroform, methylene chloride, dichloroethane, methanol, ethanol, diethyl ether etc. or a mixed solvent thereof in the presence of metal complex hydride (e.g., sodium triacetoxyborohydride, sodium cyanoborohydride, sodium borohydride, lithium borohydride, lithium aluminum hydride etc.). The reaction temperature is about −78 to 100° C., and the reaction time is several dozen min to 2 days. Phenylenediamine or pyridinediamine of the formula (VIII), and the keto compound of the formula (VII) are known compounds. For example, phenylenediamine of the formula (VIII) can be produced by the method described in J. Org. Chem., 2001, 66, 919 or Org. Synth., 1943, 501, and pyridinediamine can be produced by the method described in Org. Synth., 1964, 34. The keto compound of the formula (VII) can be produced by the method described in Bioorganic & Medicinal Chemistry Letters, 1999, 9, 2343.

The compound of the formula (IX) produced by this reaction can be carbonylated or thiocarbonylated by a known method (see Bioorganic & Medicinal Chemistry Letters, 1996, 6, 1641, Chem. Pharm. Bull., 1989, 37, 962, Bioorganic & Medicinal Chemistry Letters, 1999, 9, 1537 and the like) to give the compound of the formula (I-1).

Method 4

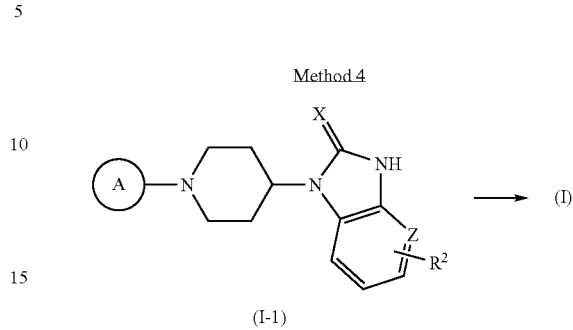

wherein each symbol is as defined in the formula (I).

The compound of the formula (I-1) wherein $R^1$ is hydrogen is subjected to alkylation, alkenylation, phenylation, benzylation or acylation to give the compound of the formula (I).

The compound of the formula (I-1) wherein $R^1$ is hydrogen to can be subjected to alkylation, alkenylation, phenylation, benzylation or acylation by a conventional method, for example, in the presence of the corresponding alkyl halide, alkenyl halide, benzyl halide or acyl halide such as methyl iodide, allyl bromide, benzyl bromide, ethyl bromide, acetyl chloride, ethyl bromoacetate and the like. This reaction is performed in the presence of metal hydride such as sodium hydride at a temperature of about −78 to 100° C. for a reaction time of several dozen min to 2 days.

Compound (VII) can also be obtained by a reduction reaction via compound (XI) that can be produced by reacting the compound of the formula (II) with hydroxylamine, as shown in the following scheme.

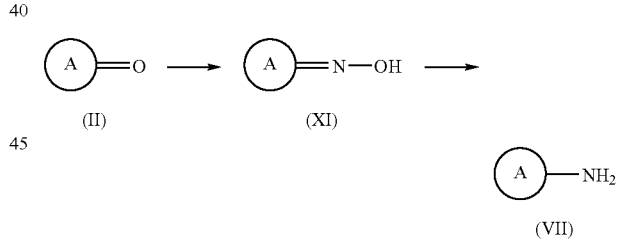

wherein ring A is as defined in the formula (I).

The compound of the formula (XI), which is a starting material compound, can be produced by a known method. For example, those described in "The Chemistry of Open-Chain Organic Nitrogen Compounds", Vol 2, p 1 (1966) and "Organic Functional Group Preparations", Vol 3, p 322 (1972) can be applied.

Reduction of oxime like the formula (XI) to amine can be performed by catalytic hydrogenation, Raney alloy-sodium hydroxide, diborane and sodium bis(2-methoxyethoxy)aluminum hydride and the like according to a known method. For example, those described in "Shin Jikken Kagaku Koza (Courses in Experimental Chemistry) vol. 14", p 1339 (1978) can be used.

Method 5

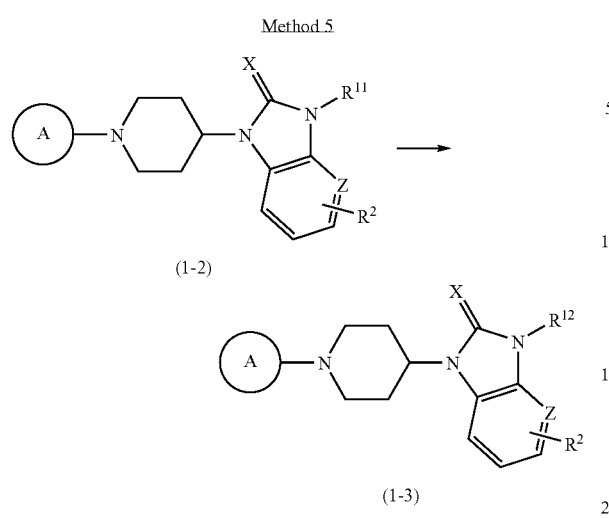

(1-2)

(1-3)

wherein $R^{11}$ is lower alkyl-carboxyl, $R^{12}$ is lower alkyl-C(O)NR³R⁴, and $R^3$, $R^4$ and other symbols are as defined in the formula (I).

A carboxylic acid compound represented by the formula (I-2) or a reactive derivative thereof and amine are reacted to give the compound of the formula (I-3). A reactive derivative of the carboxylic acid compound includes acid halide such as acid chloride, acid anhydride, mixed acid anhydride formed from ethyl chloroformate and the like, ester such as methyl ester, ethyl ester and the like, and reactive derivatives produced from carbodiimide such as WSC.HCl (water soluble carbodiimide hydrochloride), DCC (dicyclohexylcarbodiimide) and the like.

The reaction is performed in an organic solvent such as N,N-dimethylformamide, dimethyl sulfoxide, dioxane, tetrahydrofuran, acetonitrile, chloroform, methylene chloride, dichloroethane, toluene and the like. The reaction temperature is about −78 to 100° C., and the reaction time is several dozen min to 2 days. Where necessary, an organic base such as pyridine, triethylamine, diisopropylethylamine and the like is used as an acid scavenger.

When the compound of the formula (I) synthesized as shown above is obtained as a racemate, an optically pure compound can be produced by converting the racemic mixture to an enantiomer component thereof. It is also possible to separate the sterically selective isomer from its racemic mixture at a suitable intermediate stage.

In addition, an enantiomer of the compound of the formula (I) can be produced using an optically active starting material (IV)' by the method described in WO03/082333 as shown in the following scheme.

Method 3'

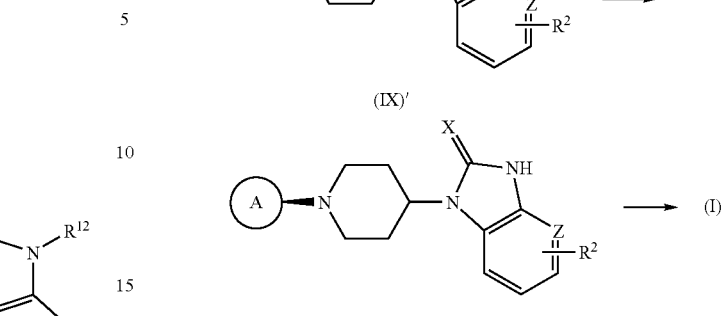

wherein each symbol is as defined in the above-mentioned formula (I).

Where necessary, the obtained compound of the formula (I) is converted to a pharmaceutically acceptable salt. Formation of salt is known per se, and is performed at room temperature by a well-known method. Not only salts with inorganic acid but also salts with organic acid are considered and, when the compound has a carboxyl group, salts with inorganic base and organic base are also considered. Acid addition salts such as hydrochloride, oxalate, fumarate, maleate and the like, sodium salt, potassium salt, calcium salt, magnesium salt and the like are examples of such salts.

The compound of the present invention can be administered orally and parenterally. The dosage form includes tablet, capsule, granule, powder, injection, ointment, suppository and the like. These can be formulated by combining the compound of the present invention with various pharmaceutically acceptable additives such as excipient, bulking agent, lubricant, binder, disintegrant, coating agent, film-forming agent, base, solvent and the like, using conventional techniques.

While the dose can be appropriately selected according to symptom, age, dosage form and the like, it is generally 0.1 to 5000 mg, preferably 1 to 1000 mg per day in the case of an oral preparation, which can be administered in one to several portions.

EXAMPLES

While the results of Examples, Preparation Examples and Pharmacological tests are shown in the following, these Examples are provided for better understanding of the present invention and do not limit the scope of the present invention.

Example 1

1-[1-(1,2,3,4-tetrahydronaphthalen-1-yl)piperidin-4-yl]-1,3-dihydro-2H-benzimidazol-2-one α-Tetralone (1.0 g) was dissolved in ethanol (20 ml), sodium borohydride (0.26 g) was added, and the mixture was stirred at room temperature for 30 min. 1N Hydrochloric acid (10 ml) was added to cease the reaction. Ethanol was evaporated, and the aqueous solution was extracted with chloroform. The extract was dried over anhydrous magnesium sulfate, and concentrated. The obtained residue was dissolved in chloroform (10 ml), thionyl chloride (1.0 ml) was added, and the mixture was stirred with heating under reflux for 30 min.

Chloroform and thionyl chloride were evaporated under reduced pressure, and the residue was dissolved in dimethylformamide (10 ml). Potassium carbonate (2.5 g), 4-(2-keto-1-benzimidazolinyl)piperidine (0.50 g) and sodium iodide (0.69 g) were added, and the mixture was stirred at 150° C. for 2 hr. After cooling to room temperature, water was added, and the mixture was extracted with ethyl acetate. The extract was washed with saturated brine, and dried over anhydrous magnesium sulfate, and the solvent was evaporated. The residue was purified by silica gel column chromatography (hexane/ethyl acetate) to give the title compound (481 mg) as a yellow solid.

$^1$H-NMR (CDCl$_3$)$\delta_{TMS}$:1.63-1.74(m, 3H), 1.92-2.05(m, 3H), 2.27-2.32(m, 2H), 2.60(m, 1H), 2.73(m, 4H), 3.01(m, 1H), 3.92(m, 1H), 4.36(m, 1H), 7.06-7.26(m, 6H), 7.33(d, J=7.8 Hz, 1H), 7.80(d, J=7.5 Hz, 1H), 9.21(brs, 1H)

FAB-MS (M+H)$^+$:348

Example 2

2-{3-[1-(1,2,3,4-tetrahydronaphthalen-1-yl)piperidin-4-yl]-2,3-dihydro-2-oxo-benzimidazol-1-yl}-N-methylacetamide 1-[1-(1,2,3,4-Tetrahydronaphthalen-1-yl)piperidin-4-yl]-1,3-dihydro-2H-benzimidazol-2-one (476 mg) was dissolved in tetrahydrofuran (5 ml), 60% sodium hydride (66 mg) was added, and the suspension was stirred at 50° C. for 30 min. After cooling to room temperature, ethyl bromoacetate (0.167 ml) was added, and the mixture was stirred for 1 hr. 40% Methylamine-methanol solution (5 ml) was added, the mixture was stirred at room temperature for 1 hr, and the reaction mixture was concentrated under reduced pressure. The obtained residue was purified by silica gel column chromatography (chloroform/methanol) to give the title compound (567 mg) as a pale-yellow powder.

$^1$H-NMR (CDCl$_3$)$\delta_{TMS}$:1.67-1.74(m, 3H), 1.93-2.04(m, 3H), 2.27-2.32(m, 2H), 2.60(m, 1H), 2.71-2.86(m, 7H), 3.02 (m, 1H), 3.92(m, 1H), 4.35(m, 1H), 4.51(s, 2H), 6.18(brs, 1H), 7.06-7.26(m, 6H), 7.35(d, J=7.5 Hz, 1H), 7.78(d, J=7.6 Hz, 1H)

FAB-MS (M+H)$^+$:419

Example 3

(R)-1-[1-(1,2,3,4-tetrahydronaphthalen-1-yl)piperidin-4-yl]-1,3-dihydro-2H-benzimidazol-2-one (1) (S)-(+)-1,2,3,4-Tetrahydro-1-naphthol (1.0 g) and diphenylphosphoryl azide (2.23 g) were dissolved in toluene (10 ml), diazabicycloundecene (1.23 g) was added, and the mixture was stirred at room temperature for 6 hr. The reaction mixture was poured into water, the mixture was extracted with toluene, and the combined organic layer was washed with 1N hydrochloric acid and water, dried over anhydrous magnesium sulfate, and concentrated. The residue was purified by silica gel column chromatography (hexane/ethyl acetate) to give (R)-1-azido-1,2,3,4-tetrahydronaphthalene (1.20 g) as a colorless oil.

$^1$H-NMR (CDCl$_3$)$\delta_{TMS}$1.81-1.84(m, 1H), 1.93-2.04(m, 3H), 2.77-2.85(m, 2H), 4.57(m, 1H), 7.14-7.29(m, 4H)

(2) (R)-1-Azido-1,2,3,4-tetrahydronaphthalene (1.20 g) was dissolved in a mixed solvent (11 ml) of tetrahydrofuran/water (10:1), triphenylphosphine (2.35 g) was added, and the mixture was stirred with heating under reflux for 2 hr. After cooling to room temperature, the solvent was evaporated, 1N hydrochloric acid was added to the residue, and unnecessary substances were removed by extraction with ethyl acetate. The aqueous phase was alkalified with potassium carbonate, and the mixture was extracted with ethyl acetate. The extract was washed with water and saturated brine, dried over anhydrous magnesium sulfate, and concentrated. The residue was purified by amine-coated silica gel to give (R)-1,2,3,4-tetrahydronaphthalen-1-ylamine (759 mg) as a colorless oil.

$^1$H-NMR (CDCl$_3$)$\delta_{TMS}$: 1.67-1.81(m, 2H), 1.92-2.05(m, 2H), 2.34-2.82(m, 2H), 3.98(t, J=5.7 Hz, 1H), 7.07-7.19(m, 3H), 7.41(d, J=8.7 Hz, 1H)

(3) (R)-1,2,3,4-Tetrahydronaphthalen-1-ylamine (759 mg) was dissolved in ethanol (7.3 ml), and potassium carbonate (70 mg) was added. 1-Ethyl-1-methyl-4-oxopiperidinium iodide (1.59 g) dissolved in water (4.4 ml) was added, and the mixture was stirred with heating under reflux for 1 hr. The reaction mixture was poured into water, and the mixture was extracted with ethyl acetate. The extract was washed with saturated brine, dried over anhydrous magnesium sulfate, and concentrated. The obtained residue was purified by silica gel column chromatography (hexane/ethyl acetate) to give (R)-1-(1,2,3,4-tetrahydronaphthalen-1-yl)piperidin-4-one (910 mg) as a pale-yellow oily substance.

$^1$H-NMR (CDCl$_3$)$\delta_{TMS}$:1.59-1.69(m, 2H), 1.96-2.01(m, 2H), 2.43-2.49(m, 4H), 2.75-2.82(m, 4H), 2.86-2.92(m, 2H), 4.00-4.05(m, 1H), 7.07-7.22(m, 3H), 7.77(d, J=6.9 Hz, 1H)

(4) (R)-1-(1,2,3,4-tetrahydronaphthalen-1-yl)piperidin-4-one (910 mg) was dissolved in tetrahydrofuran (21 ml), and 1,2-phenylenediamine (859 mg) was added. The solution was ice-cooled, sodium triacetoxyborohydride (2.31 g) and acetic acid (0.92 ml) were added, and the mixture was stirred at room temperature for 3 hr. The reaction mixture was poured into water, and the mixture was alkalified with potassium carbonate, and extracted with ethyl acetate. The extract was washed with saturated brine, dried over anhydrous sodium sulfate, and concentrated. The obtained residue was purified by silica gel column chromatography (hexane/ethyl acetate) to give (R)-N-[1-(1,2,3,4-tetrahydronaphthalen-1-yl)piperidin-4-yl]-benzene-1,2-diamine (970 mg) as a pale-yellow solid.

$^1$H-NMR (CDCl$_3$)$\delta_{TMS}$:1.40(m, 1H), 1.55-1.75(m, 3H), 1.96-2.01(m, 3H), 2.10(m, 1H), 2.24(m, 1H), 2.61-2.83(m, 5H), 3.20-3.35(m, 3H), 3.83-3.88(m, 1H), 6.64-6.80(m, 4H), 7.07-7.16(m, 3H), 7.71(d, J=6.9 Hz, 1H)

(5) (R)-N-[1-(1,2,3,4-Tetrahydronaphthalen-1-yl)piperidin-4-yl]-benzene-1,2-diamine (570 mg) was dissolved in tetrahydrofuran (3 ml), 1,1'-carbonyldiimidazole (344 mg) was added, and the mixture was stirred at room temperature for 3 hr. The reaction mixture was poured into water, and the mixture was extracted with ethyl acetate. The extract was washed with saturated brine, dried over anhydrous magnesium sulfate, and concentrated. The obtained residue was purified by silica gel column chromatography (hexane/ethyl acetate) to give the title compound (543 mg) as a white solid.

$^1$H-NMR (CDCl$_3$)$\delta_{TMS}$:1.63-1.74(m, 3H), 1.92-2.05(m, 3H), 2.27-2.32(m, 2H), 2.60(m, 1H), 2.73(m, 4H), 3.01(m, 1H), 3.92(m, 1H), 4.36(m, 1H), 7.06-7.26(m, 6H), 7.33(d, J=7.8 Hz, 1H), 7.80(d, J=7.5 Hz, 1H), 9.21(brs, 1H)

FAB-MS (M+H)$^+$:348

The following compounds can be synthesized according to the above-mentioned Examples.

Example 4

(R)-2-{3-[1-(1,2,3,4-tetrahydronaphthalen-1-yl)piperidin-4-yl]-2,3-dihydro-2-oxo-benzimidazol-1-yl}-N-methylacetamide In the same manner as in Example 2 and using (R)-1-[1-(1,2,3,4-tetrahydronaphthalen-1-yl)piperidin-4-yl]-1,3-dihydro-2H-benzimidazol-2-one, the title compound was obtained as a white solid.

$^1$H-NMR (CDCl$_3$)$\delta_{TMS}$:1.65-1.75(m, 3H), 1.93-2.04(m, 3H), 2.28-2.33(m, 2H), 2.60(m, 1H), 2.70-2.86(m, 7H), 3.02 (m, 1H), 3.92(m, 1H), 4.35(m, 1H), 4.51(s, 2H), 6.15(brs, 1H), 7.06-7.26(m, 6H), 7.35(d, J=7.5 Hz, 1H), 7.78(d, J=7.6 Hz, 1H)

FAB-MS (M+H)$^+$:419

$[\alpha]_D^{24}$=+17.2°

Example 5

(S)-1-[1-(1,2,3,4-tetrahydronaphthalen-1-yl)piperidin-4-yl]-1,3-dihydro-2H-benzimidazol-2-one In the same manner as in Example 3 and using (R)-(−)-1,2,3,4-tetrahydro-1-naphthol, the title compound was obtained as a white solid.

$^1$H-NMR (CDCl$_3$)$\delta_{TMS}$:1.64-1.73(m, 3H), 1.92-2.05(m, 3H), 2.29-2.32(m, 2H), 2.61(m, 1H), 2.73(m, 4H), 3.01(m, 1H), 3.92(m, 1H), 4.36(m, 1H), 7.06-7.26(m, 6H), 7.33(d, J=7.2 Hz, 1H), 7.80(d, J=7.5 Hz, 1H), 9.45(brs, 1H)

FAB-MS (M+H)$^+$:348

Example 6

(S)-2-{3-[1-(1,2,3,4-tetrahydronaphthalen-1-yl)piperidin-4-yl]-2,3-dihydro-2-oxo-benzimidazol-1-yl}-N-methylacetamide In the same manner as in Example 2 and using (S)-1-[1-(1,2,3,4-tetrahydronaphthalen-1-yl)piperidin-4-yl]-1,3-dihydro-2H-benzimidazol-2-one, the title compound was obtained as a white solid.

$^1$H-NMR (CDCl$_3$)$\delta_{TMS}$:1.66-1.72(m, 3H), 1.89-2.03(m, 3H), 2.28-2.33(m, 2H), 2.60(m, 1H), 2.71-2.86(m, 7H), 3.02 (m, 1H), 3.92(m, 1H), 4.35(m, 1H), 4.51(s, 2H), 6.16(brs, 1H), 7.06-7.22(m, 6H), 7.35(d, J=7.5 Hz, 1H), 7.79(d, J=7.6 Hz, 1H)

FAB-MS (M+H)$^+$:419

$[\alpha]_D^{25}$=+16.8°

Example 7

1-[1-(5-methyl-1,2,3,4-tetrahydronaphthalen-1-yl)piperidin-4-yl]-1,3-dihydro-2H-benzimidazol-2-one In the same manner as in Example 1 and using 5-methyl-1-tetralone, the title compound was obtained as a white solid.

$^1$H-NMR (CDCl$_3$)$\delta_{TMS}$:1.63-1.73(m, 3H), 1.92-2.09(m, 3H), 2.23(s, 3H), 2.27-2.32(m, 2H), 2.57-2.72(m, 4H), 2.87 (m, 1H), 3.01(m, 1H), 3.92(m, 1H), 4.36(m, 1H), 7.03-7.17 (m, 5H), 7.33(d, J=8.9 Hz, 1H), 7.72(d, J=7.7 Hz, 1H), 9.36 (brs, 1H)

FAB-MS (M+H)$^+$:362

Example 8

2-{3-[1-(5-methyl-1,2,3,4-tetrahydronaphthalen-1-yl)piperidin-4-yl]-2,3-dihydro-2-oxo-benzimidazol-1-yl}-N-methylacetamide In the same manner as in Example 2 and using 1-[1-(5-methyl-1,2,3,4-tetrahydronaphthalen-1-yl)piperidin-4-yl]-1,3-dihydro-2H-benzimidazol-2-one, the title compound was obtained as a white solid.

$^1$H-NMR (CDCl$_3$)$\delta_{TMS}$:1.63-1.74(m, 3H), 1.89-2.09(m, 3H), 2.23(s, 3H), 2.28(m, 2H), 2.56-2.72(m, 4H), 2.79(d, J=4.5 Hz, 3H), 2.85(m, 1H), 3.02(m, 1H), 3.90(m, 1H), 4.35 (m, 1H), 4.51(s, 2H), 6.16(brs, 1H), 7.03-7.17(m, 5H), 7.36 (d, J=7.5 Hz, 1H), 7.70(d, J=7.86 Hz, 1H)

FAB-MS (M+H)$^+$:433

Example 9

(R)-1-[1-(5-methyl-1,2,3,4-tetrahydronaphthalen-1-yl)piperidin-4-yl]-1,3-dihydro-2H-benzimidazol-2-one (1) A solution of 5-methyl-1,2,3,4-tetrahydronaphthalen-1-one (3.2 g), (R)-t-butylsulfinamide (2.4 g) and titanium tetraisopropoxide (9.0 g) in tetrahydrofuran (50 ml) was stirred at 75° C. for 96 hr. The reaction mixture was cooled to −50° C., and sodium borohydride (3.0 g) was added by small portions. The mixture was stirred for 7 hr while allowing to warm to room temperature. The reaction mixture was poured into ice water, the mixture was extracted with ethyl acetate, and the extract was washed with water and saturated brine, dried over anhydrous sodium sulfate, and concentrated. The obtained residue was purified by silica gel column chromatography (hexane/ethyl acetate) to give (RS)-2-methyl-N-((S)-5-methyl-1,2,3,4-tetrahydronaphthalen-1-yl)propane-2-sulfinamide (2.3 g) as a pale-brown solid.

$^1$H-NMR (CDCl$_3$)$\delta_{TMS}$:1.21(s, 9H), 1.79-1.85(m, 2H), 1.90-2.02(m, 2H), 2.23(s, 3H), 2.50-2.60(m, 1H), 2.70-2.80 (m, 1H), 3.20(s, 1H), 4.58(m, 1H), 7.08-7.15(m, 2H), 7.29-7.31(m, 1H)

(2) (RS)-2-Methyl-N-((S)-5-methyl-1,2,3,4-tetrahydronaphthalen-1-yl)propane-2-sulfinamide (277 mg) was dissolved in 5-10% hydrogen chloride-methanol (25 ml) under ice-cooling, and the mixture was stirred for 2 hr under ice-cooling. To the reaction mixture was added 1N aqueous sodium hydroxide solution, and the mixture was extracted with ethyl acetate. The extract was washed with saturated brine, dried over anhydrous sodium sulfate, and concentrated. The obtained residue was purified by amino-silica gel column chromatography (hexane/ethyl acetate) to give (R)-1-amino-5-methyl-1,2,3,4-tetrahydronaphthalene (130 mg) as a brown oily substance.

$^1$H-NMR (CDCl$_3$)$\delta_{TMS}$:1.67-1.73(m, 1H), 1.78-1.85(m, 1H), 1.92-2.01(m, 2H), 2.52-2.71(m, 2H), 3.97-4.00(m, 1H), 7.03(d, J=7.3 Hz, 1H), 7.13(t, J=7.3 Hz, 1H), 7.26(m, 1H)

(3) (R)-1-Amino-5-methyl-1,2,3,4-tetrahydronaphthalene (1.71 g) was dissolved in ethanol (20 ml), and potassium carbonate (1.47 g) was added. 1-Ethyl-1-methyl-4-oxopiperidinium iodide (3.14 g) dissolved in water (5 ml) was added, and the mixture was stirred with heating under reflux for 5 hr. The reaction mixture was poured into water, and the mixture was extracted with ethyl acetate. The extract was washed with saturated brine, dried over anhydrous sodium sulfate, and concentrated. The obtained residue was purified by silica gel column chromatography (hexane/ethyl acetate) to give (R)-1-(5-methyl-1,2,3,4-tetrahydronaphthalen-1-yl)piperidin-4-one (1.84 g) as a pale-yellow oily substance.

$^1$H-NMR (CDCl$_3$)$\delta_{TMS}$:1.50-1.70(m, 2H), 1.96-1.99(m, 1H), 2.04-2.09(m, 1H), 2.22(s, 1H), 2.43-2.58(m, 5H), 2.64-2.73(m, 1H), 2.73-2.79(m, 2H), 2.86-2.92(m, 2H), 4.01-4.13(m, 1H), 7.04(d, J=7.3 Hz, 1H), 7.11(t, J=7.6 Hz, 1H), 7.68(d, J=7.6 Hz, 1H)

(4) (R)-1-(5-Methyl-1,2,3,4-tetrahydronaphthalen-1-yl)piperidin-4-one (1.84 g) was dissolved in dichloroethane (55 ml), and 1,2-phenylenediamine (1.23 g) was added. To the solution were added sodium triacetoxyborohydride (3.61 g) and acetic acid (0.97 ml). The mixture was stirred at room temperature for 24 hr, alkalified with saturated sodium hydrogen carbonate, and extracted with chloroform. The extract was washed with saturated brine, dried over anhydrous sodium sulfate, and concentrated. The obtained residue was purified by silica gel column chromatography (hexane/ethyl acetate) to give (R)-N-[1-(5-methyl-1,2,3,4-tetrahydronaphthalen-1-yl)piperidin-4-yl]-benzene-1,2-diamine (1.83 g) as a pale-brown solid.

$^1$H-NMR (CDCl$_3$)$\delta_{TMS}$:1.40(m, 1H), 1.55-1.75(m, 3H), 1.96-2.01(m, 2H), 2.04-2.15(m, 2H), 2.22(s, 3H), 2.24(m, 1H), 2.50-2.75(m, 4H), 2.80-2.90(m, 1H), 3.20-3.35(m, 3H), 3.83-3.88(m, 1H), 6.65-6.80(m, 4H), 7.01(d, J=7.2 Hz, 1H), 7.08(t, J=7.6 Hz, 1H), 7.62(d, J=7.6 Hz, 1H)

(5) (R)-N-[1-(5-Methyl-1,2,3,4-tetrahydronaphthalen-1-yl)piperidin-4-yl]-benzene-1,2-diamine (1.83 g) was dissolved in tetrahydrofuran (100 ml), 1,1'-carbonyldiimidazole (973 mg) was added, and the mixture was stirred at room temperature for 10 hr. The reaction mixture was poured into water, and the mixture was extracted with ethyl acetate. The extract was washed with saturated brine, dried over anhydrous sodium sulfate, and concentrated. The obtained residue was purified by silica gel column chromatography (hexane/ethyl acetate) and crystallized with hexane/ethyl acetate to give the title compound (1.2 g) as a white solid.

$^1$H-NMR (CDCl$_3$)$\delta_{TMS}$:1.63-1.74(m, 3H), 1.89-2.15(m, 3H), 2.22(s, 3H), 2.27-2.36(m, 2H), 2.50-2.71(m, 4H), 2.88 (m, 1H), 3.02(m, 1H), 3.90(m, 1H), 4.36(m, 1H), 7.02-7.16 (m, 5H), 7.34(d, J=7.6 Hz, 1H), 7.71(d, J=7.6 Hz, 1H), 9.57 (brs, 1H)

FAB-MS (M+H)$^+$:362

$[\alpha]_D^{29.7}$=+38.4 (c=0.5, chloroform)

Example 10

(R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide (R)-1-[1-(5-Methyl-1,2,3,4-tetrahydronaphthalen-1-yl) piperidin-4-yl]-1,3-dihydro-2H-benzimidazol 2-one (995 mg) was dissolved in DMF (10 ml). Sodium hydride (132 mg, 60%) was added, and the suspension was stirred at room temperature for 40 min. Ethyl bromoacetate (458 μl) was added, and the mixture was stirred for 4 hr. The reaction mixture was poured into ice water, and the mixture was extracted with ethyl acetate. The extract was washed with water and saturated aqueous ammonium chloride solution, dried over sodium sulfate, and concentrated. To the residue was added 40% methylamine-methanol solution (30 ml), the mixture was stirred at room temperature for 2.5 hr, and the reaction mixture was concentrated under reduced pressure. The obtained residue was purified by silica gel column chromatography (chloroform/methanol), and crystallized with ethyl acetate to give the title compound (1.0 g) as pale-yellow crystals.

$^1$H-NMR (CDCl$_3$)$\delta_{TMS}$:1.63-1.74(m, 3H), 1.89-2.09(m, 3H), 2.23(s, 3H), 2.28(m, 2H), 2.56-2.72(m, 4H), 2.79(d, J=4.5 Hz, 3H), 2.85(m, 1H), 3.02(m, 1H), 3.90(m, 1H), 4.35 (m, 1H), 4.51(s, 2H), 6.16(brs, 1H), 7.03-7.17(m, 5H), 7.36 (d, J=7.5 Hz, 1H), 7.70(d, J=7.86 Hz, 1H)

FAB-MS (M+H)$^+$:433

$[\alpha]_D^{29.1}$=+26.8 (c=0.5, chloroform)

Example 11

1-[1-(5-chloro-1,2,3,4-tetrahydronaphthalen-1-yl) piperidin-4-yl]-1,3-dihydro-2H-benzimidazol-2-one In the same manner as in Example 1 and using 5-chloro-1-tetralone, the title compound was obtained as a white solid.

$^1$H-NMR (CDCl$_3$)$\delta_{TMS}$:1.62-1.76(m, 3H), 1.92-2.10(m, 3H), 2.28-2.32(m, 2H), 2.58-2.67(m, 3H), 2.87-3.04(m, 3H), 3.88(m; 1H), 4.35(m, 1H), 7.06-7.25(m, 5H), 7.31(d, J=7.5 Hz, 1H), 7.78(d, J=7.5 Hz, 1H), 9.40(brs, 1H)

FAB-MS (M+H)$^+$:382

Example 12

2-{3-[1-(5-chloro-1,2,3,4-tetrahydronaphthalen-1-yl) piperidin-4-yl]-2,3-dihydro-2-oxo-benzimidazol-1-yl}-N-methylacetamide In the same manner as in Example 2 and using 1-[1-(5-chloro-1,2,3,4-tetrahydronaphthalen-1-yl)piperidin-4-yl]-1, 3-dihydro-2H-benzimidazol-2-one, the title compound was obtained as a white solid.

$^1$H-NMR (CDCl$_3$)$\delta_{TMS}$:1.62-1.76(m, 3H), 1.89-2.09(m, 3H), 2.29(m, 2H), 2.58-2.68(m, 3H), 2.79(d, J=4.8 Hz, 3H), 2.89(m, 2H), 3.01(m, 1H), 3.90(m, 1H), 4.32(m, 1H), 4.51(s, 2H), 6.17(brs, 1H), 7.06-7.19(m, 5H), 7.32(d, J=7.5 Hz, 1H), 7.76(d, J=7.68 Hz, 1H)

FAB-MS (M+H)$^+$:453

Example 13

1-[1-(5,7-dimethyl-1,2,3,4-tetrahydronaphthalen-1-yl)piperidin-4-yl]-1,3-dihydro-2H-benzimidazol-2-one In the same manner as in Example 1 and using 5,7-dimethyl-1-tetralone, the title compound was obtained as a white solid.

$^1$H-NMR (CDCl$_3$)$\delta_{TMS}$:1.62-1.72(m, 3H), 1.93-2.13(m, 3H), 2.19(s, 3H), 2.27-2.34(m, 5H), 2.54-2.99(m, 6H), 3.86 (m, 1H), 4.35(m, 1H), 6.87(s, 1H), 7.04-7.14(m, 3H), 7.34(d, J=6.9 Hz, 1H), 7.51(s, 1H), 9.62(brs, 1H)

FAB-MS (M+H)$^+$:376

Example 14

2-{3-[1-(5,7-dimethyl-1,2,3,4-tetrahydronaphthalen-1-yl)piperidin-4-yl]-2,3-dihydro-2-oxo-benzimidazol-1-yl}-N-methylacetamide In the same manner as in Example 2 and using 1-[1-(5,7-dimethyl-1,2,3,4-tetrahydronaphthalen-1-yl)piperidin-4-yl]-1,3-dihydro-2H-benzimidazol-2-one, the title compound was obtained as a white solid.

¹H-NMR (CDCl₃)δ_TMS:1.65-1.71(m, 3H), 1.92-2.07(m, 3H), 2.19(s, 3H), 2.25-2.33(m, 5H), 2.61-2.84(m, 8H), 3.00 (m, 1H), 3.86(m, 1H), 4.33(m, 1H), 4.51(s, 2H), 6.21(brs, 1H), 6.88(s, 1H), 7.06-7.17(m, 3H), 7.35(d, J=7.5 Hz, 1H), 7.49(s, 1H)
FAB-MS (M+H)⁺:447

Example 15

1-(1-indan-1-ylpiperidin-4-yl)-1,3-dihydro-2H-benzimidazol-2-one

In the same manner as in Example 1 and using 1-indanone, the title compound was obtained as a brown solid.
¹H-NMR (CDCl₃)δ_TMS:1.78-1.86(m, 2H), 2.09-2.16(m, 2H), 2.39(m, 2H), 2.56(m, 2H), 2.79-3.09(m, 4H), 4.35(m, 1H), 4.44(m, 1H), 7.04-7.12(m, 3H), 7.21-7.26(m, 3H), 7.35 (m, 1H), 7.43(m, 1H), 9.64(brs, 1H)
FAB-MS (M+H)⁺:334

Example 16

2-{3-(1-indan-1-ylpiperidin-4-yl)-2,3-dihydro-2-oxo-benzimidazol-1-yl}-N-methylacetamide In the same manner as in Example 2 and using 1-(1-indan-1-ylpiperidin-4-yl)-1,3-dihydro-2H-benzimidazol-2-one, the title compound was obtained as a brown solid.
¹H-NMR (CDCl₃)δ_TMS:1.76-1.86(m, 2H), 2.08-2.16(m, 2H), 2.39(m, 2H), 2.55(m, 2H), 2.80(d, J=4.9 Hz, 3H), 2.82-3.10(m, 4H), 4.35(m, 1H), 4.44(m, 1H), 4.50(s, 2H), 6.17 (brs, 1H), 7.05-7.14(m, 3H), 7.23-7.26(m, 3H), 7.36-7.43(m, 2H)
FAB-MS (M+H)⁺:406

Example 17

1-(4-fluoro-1-indan-1-ylpiperidin-4-yl)-1,3-dihydro-2H-benzimidazol-2-one hydrochloride In the same manner as in Example 1 and using 4-fluoro-1-indanone, 1-(4-fluoro-1-indan-1-ylpiperidin-4-yl)-1,3-dihydro-2H-benzimidazol-2-one was synthesized, which was then converted to hydrochloride with 4N hydrochloric acid-ethyl acetate solution to give the title compound as a brown solid.
¹H-NMR (DMSO-d₆)δ_TMS:1.83(m, 2H), 2.50(m, 2H), 2.60(m, 1H) 2.80(m, 1H), 2.99-3.29(m, 5H), 3.51(m, 1H), 4.60(m, 1H), 5.10(m, 1H), 6.98(m, 3H), 7.26(t, J=9 Hz, 1H), 7.43(m, 1H), 7.71(m, 1H), 7.86(m, J=7.5 Hz, 1H), 10.9(brs, 1H), 11.6(brs, 1H)
FAB-MS (M+H)⁺:352

Example 18

2-{3-(4-fluoro-1-indan-1-ylpiperidin-4-yl)-2,3-dihydro-2-oxo-benzimidazol-1-yl}-N-methylacetamide hydrochloride In the same manner as in Example 2 and using 1-(4-fluoro-1-indan-1-ylpiperidin-4-yl)-1,3-dihydro-2H-benzimidazol-2-one, 2-{3-(4-fluoro-1-indan-1-ylpiperidin-4-yl)-2,3-dihydro-2-oxo-benzimidazol-1-yl}-N-methylacetamide was synthesized, which was then converted to hydrochloride with 4N hydrochloric acid-ethyl acetate solution to give the title compound as a pale-yellow solid.
¹H-NMR (DMSO-d₆)δ_TMS:1.87(m, 2H), 2.44(m, 3H), 2.60(m, 3H), 2.83(m, 1H), 3.01-3.41(m, 5H), 3.53(m, 1H), 4.43(s, 2H), 4.67(m, 1H), 5.10(m, 1H), 7.05(m, 3H), 7.27(t, J=9 Hz, 1H), 7.42(m, 1H), 7.76(m, 1H), 7.82(m, J=7.5 Hz, 1H), 8.11(brs, 1H), 11.4(brs, 1H)
FAB-MS (M+H)⁺:423

Example 19

1-(4-methyl-1-indan-1-ylpiperidin-4-yl)-1,3-dihydro-2H-benzimidazol-2-one

In the same manner as in Example 1 and using 4-methyl-1-indanone, the title compound was obtained as a brown solid.
¹H-NMR (CDCl₃)δ_TMS:1.74-1.85(m, 2H), 2.11-2.16(m, 2H), 2.27(s, 3H), 2.39(m, 2H), 2.54(m, 2H), 2.74-2.85(m, 3H), 3.05(m, 1H), 4.34(m, 1H), 4.45(m, 1H), 7.04-7.18(m, 5H), 7.26-7.34(m, 2H), 9.54(brs, 1H)
FAB-MS (M+H)⁺:348

Example 20

2-{3-(4-methyl-1-indan-1-ylpiperidin-4-yl)-2,3-dihydro-2-oxo-benzimidazol-1-yl}-N-methylacetamide hydrochloride In the same manner as in Example 2 and using 1-(4-methyl-1-indan-1-ylpiperidin-4-yl)-1,3-dihydro-2H-benzimidazol-2-one, 2-{3-(4-methyl-1-indan-1-ylpiperidin-4-yl)-2,3-dihydro-2-oxo-benzimidazol-1-yl}-N-methylacetamide was synthesized, which was then converted to hydrochloride with 4N hydrochloric acid-ethyl acetate solution to give the title compound as a brown solid.
¹H-NMR (DMSO-d₆)δ_TMS:1.86(m, 2H), 2.26(s, 3H), 2.39 (m, 1H), 2.60(m, 4H), 2.87(m, 2H), 3.00-3.26(m, 5H), 3.49 (m, 1H), 4.43(s, 2H), 4.66(m, 1H), 5.04(m, 1H), 7.04(m, 3H), 7.24(m, 2H), 7.79(m, 2H), 8.12 (m, 1H), 11.3(brs, 1H)
FAB-MS (M+H)⁺:419

Example 21

1-(6-methyl-1-indan-1-ylpiperidin-4-yl)-1,3-dihydro-2H-benzimidazol-2-one

In the same manner as in Example 1 and using 6-methyl-1-indanone, the title compound was obtained as a brown solid.
¹H-NMR (CDCl₃)δ_TMS:1.78-1.86(m, 2H), 2.08-2.15(m, 2H), 2.38(s, 3H), 2.41(m, 2H), 2.54(m, 2H), 2.79-2.89(m, 3H), 3.05(m, 1H), 4.33-4.42(m, 2H), 7.03-7.12(m, 5H), 7.23 (m, 1H), 7.34(m, 1H), 9.37(brs, 1H)
FAB-MS (M+H)⁺:348

Example 22

2-{3-(6-methyl-1-indan-1-ylpiperidin-4-yl)-2,3-dihydro-2-oxo-benzimidazol-1-yl}-N-methylacetamide hydrochloride In the same manner as in Example 2 and using 1-(6-methyl-1-indan-1-ylpiperidin-4-yl)-1,3-dihydro-2H-benzimidazol-2-one, 2-{3-(6-methyl-1-indan-1-ylpiperidin-4-yl)-2,3-dihydro-2-oxo-benzimidazol-1-yl}-N-methylacetamide was synthesized, which was then converted to hydrochloride with 4N hydrochloric acid-ethyl acetate solution to give the title compound as a brown solid.

¹H-NMR (DMSO-d₆)δ$_{TMS}$:1.86(m, 2H), 2.35(s, 3H), 2.39 (m, 1H), 2.51(m, 4H), 2.85(m, 2H), 3.03-3.26(m, 5H), 3.49 (m, 1H), 4.43(s, 2H), 4.66(m, 1H), 4.97(m, 1H), 7.04(m, 3H), 7.24(m, 2H), 7.79(m, 2H), 8.13(m, 1H), 11.3(brs, 1H)

FAB-MS (M+H)⁺:419

Example 23

1-(7-methyl-1-indan-1-ylpiperidin-4-yl)-1,3-dihydro-2H-benzimidazol-2-one

In the same manner as in Example 1 and using 7-methyl-1-indanone, the title compound was obtained as a brown solid.

¹H-NMR (CDCl₃)δ$_{TMS}$:1.67(m, 1H), 1.90(m, 2H), 2.23 (m, 3H), 2.42(m, 2H), 2.52(s, 3H), 2.69(m, 1H), 2.90(m, 2H), 3.04(m, 1H), 4.35(m, 1H), 4.46(m, 1H), 7.00-7.22(m, 7H), 9.33(brs, 1H)

FAB-MS (M+H)⁺:348

Example 24

2-{3-(7-methyl-1-indan-1-ylpiperidin-4-yl)-2,3-dihydro-2-oxo-benzimidazol-1-yl}-N-methylacetamide hydrochloride In the same manner as in Example 2 and using 1-(7-methyl-1-indan-1-ylpiperidin-4-yl)-1,3-dihydro-2H-benzimidazol-2-one, 2-{3-(7-methyl-1-indan-1-ylpiperidin-4-yl)-2,3-dihydro-2-oxo-benzimidazol-1-yl}-N-methylacetamide was synthesized, which was then converted to hydrochloride with 4N hydrochloric acid-ethyl acetate solution to give the title compound as a brown solid.

¹H-NMR (DMSO-d₆)δ$_{TMS}$:1.84(m, 2H), 2.30(m, 1H), 2.50(s, 3H), 2.59(d, J=4.5 Hz, 3H), 2.68-3.01(m, 4H), 3.23-3.64(m, 5H), 4.42(s, 2H), 4.66(m, 1H), 4.90(m, 1H), 7.02(m, 3H), 7.15(d, J=7.4 Hz, 1H), 7.24(d, J=7.4 Hz, 1H), 7.33 (t, J=7.5 Hz, 1H), 7.80(m, 1H), 8.13 (m, 1H), 10.3(brs, 1H)

FAB-MS (M+H)⁺:419

Example 25

1-(3,3-dimethyl-1-indan-1-ylpiperidin-4-yl)-1,3-dihydro-2H-benzimidazol-2-one

In the same manner as in Example 1 and using 3,3-dimethyl-1-indanone, the title compound was obtained as a white solid.

¹H-NMR (CDCl₃)δ$_{TMS}$:1.20(s, 3H), 1.39(s, 3H), 1.80(m, 1H), 1.94(m, 3H), 2.29(m, 2H), 2.65(m, 2H), 2.75(m, 1H), 3.10(m, 1H), 4.38(m, 1H), 4.54(m, 1H), 7.05-7.11(m, 3H), 7.18(m, 1H), 7.23(m, 2H), 7.34(m, 2H), 9.47(brs, 1H)

FAB-MS (M+H)⁺:362

Example 26

2-{3-(3,3-dimethyl-1-indan-1-ylpiperidin-4-yl)-2,3-dihydro-2-oxo-benzimidazol-1-yl}-N-methylacetamide In the same manner as in Example 2 and using 1-(3,3-dimethyl-1-indan-1-ylpiperidin-4-yl)-1,3-dihydro-2H-benzimidazol-2-one, the title compound was obtained as a white solid.

¹H-NMR (CDCl₃)δ$_{TMS}$:1.20(s, 3H), 1.38(s, 3H), 1.76-1.96 (m, 4H), 2.27-2.40(m, 2H), 2.62(m, 2H), 2.75(m, 1H), 2.79 (d, J=4.7 Hz, 3H), 3.11(m, 1H), 4.37(m, 1H), 4.51(s, 2H), 4.54(m, 1H), 6.73(brs, 1H), 7.06-7.19(m, 4H), 7.25(m, 2H), 7.38(m, 2H)

FAB-MS (M+H)⁺:433

Example 27

1-[1-(6,7,8,9-tetrahydro-5H-benzocyclohepten-5-yl) piperidin-4-yl]-1,3-dihydro-2H-benzimidazol-2-one In the same manner as in Example 1 and using 1-benzosuberone, the title compound was obtained as a white solid.

¹H-NMR (CDCl₃)δ$_{TMS}$:1.40(m, 1H), 1.72(m, 3H), 1.91-2.15 (m, 6H), 2.34(m, 1H), 2.49-2.58(m, 3H), 3.27(m, 1H), 3.32(m, 1H), 3.59(m, 1H), 4.36(m, 1H), 7.05-7.14(m, 7H), 7.24 (m, 1H), 9.46(brs, 1H)

FAB-MS (M+H)⁺:362

Example 28

2-{3-[1-(6,7,8,9-tetrahydro-5H-benzocyclohepten-5-yl)piperidin-4-yl]-2,3-dihydro-2-oxo-benzimidazol-1-yl}-N-methylacetamide In the same manner as in Example 2 and using 1-[1-(6,7,8,9-tetrahydro-5H-benzocyclohepten-5-yl)piperidin-4-yl]-1,3-dihydro-2H-benzimidazol-2-one, the title compound was obtained as a pale-yellow solid.

¹H-NMR (CDCl₃)δ$_{TMS}$:1.44(m, 1H), 1.68(m, 3H), 1.87-2.17 (m, 6H), 2.34(m, 1H), 2.51-2.63(m, 3H), 2.79(d, J=4.9 Hz, 3H), 3.23(m, 1H), 3.32(m, 1H), 3.58(m, 1H), 4.33(m, 1H), 4.50(s, 2H), 6.17(brs, 1H), 7.04-7.14(m, 7H), 7.26 (m, 1H)

FAB-MS (M+H)⁺:433

The following compounds of Examples 29-45 can be synthesized in the same manner as in Example 1.

Example 29

1-[1-(5-methoxy-1,2,3,4-tetrahydronaphthalen-1-yl) piperidin-4-yl]-1,3-dihydro-2H-benzimidazol-2-one In the same manner as in Example 1 and using 5-methoxy-1-tetralone, the title compound was obtained as a white solid.

¹H-NMR (CDCl₃)δ$_{TMS}$:1.59-1.74(m, 3H), 1.88-2.06(m, 3H), 2.26-2.35(m, 2H), 2.40-2.71(m, 3H), 2.77-2.89(m, 2H), 3.02(m, 1H), 3.82(s, 3H), 3.89(m, 1H), 4.35(m, 1H), 6.72 (d, J=8.0 Hz, 1H), 7.06-7.13(m, 3H), 7.20(t, J=8.0 Hz, 1H), 7.33(d, J=7.4 Hz, 1H), 7.47(d, J=7.8 Hz, 1H), 8.88(brs, 1H)

FAB-MS (M+H)⁺:378

Example 30

1-[1-(5-trifluoromethyl-1,2,3,4-tetrahydronaphthalen-1-yl)piperidin-4-yl]-1,3-dihydro-2H-benzimidazol-2-one Example 31

1-[1-(5-bromo-1,2,3,4-tetrahydronaphthalen-1-yl) piperidin-4-yl]-1,3-dihydro-2H-benzimidazol-2-one

Example 32

1-[1-(5-fluoro-1,2,3,4-tetrahydronaphthalen-1-yl) piperidin-4-yl]-1,3-dihydro-2H-benzimidazol-2-one

Example 33

1-[1-(8-fluoro-1,2,3,4-tetrahydronaphthalen-1-yl) piperidin-4-yl]-1,3-dihydro-2H-benzimidazol-2-one

Example 34

1-[1-(6-fluoro-1,2,3,4-tetrahydronaphthalen-1-yl) piperidin-4-yl]-1,3-dihydro-2H-benzimidazol-2-one

Example 35

1-[1-(7-fluoro-1,2,3,4-tetrahydronaphthalen-1-yl) piperidin-4-yl]-1,3-dihydro-2H-benzimidazol-2-one In the same manner as in Example 1 and using 7-fluoro-1-tetralone, the title compound was obtained as a white solid.

$^1$H-NMR (CDCl$_3$)$\delta_{TMS}$:1.65-1.77(m, 3H), 1.92(m, 1H), 2.01-2.05(m, 2H), 2.31-2.37(m, 2H), 2.56-2.72(m, 4H), 2.89 (m, 1H), 3.01(m, 1H), 3.87(m, 1H), 4.38(m, 1H), 6.84 (dt, J=2.7, 8.3 Hz, 1H), 7.00-7.15(m, 4H), 7.34(d, J=7.7 Hz, 1H), 7.55(dd, J=2.7, 10.7 Hz, 1H), 9.28(brs, 1H)

FAB-MS (M+H)$^+$:366

Example 36

1-[1-(6-methyl-1,2,3,4-tetrahydronaphthalen-1-yl) piperidin-4-yl]-1,3-dihydro-2H-benzimidazol-2-one

Example 37

1-[1-(7-methyl-1,2,3,4-tetrahydronaphthalen-1-yl) piperidin-4-yl]-1,3-dihydro-2H-benzimidazol-2-one

Example 38

1-[1-(6-methoxy-1,2,3,4-tetrahydronaphthalen-1-yl) piperidin-4-yl]-1,3-dihydro-2H-benzimidazol-2-one

Example 39

1-[1-(7-methoxy-1,2,3,4-tetrahydronaphthalen-1-yl) piperidin-4-yl]-1,3-dihydro-2H-benzimidazol-2-one In the same manner as in Example 1 and using 7-methoxy-1-tetralone, the title compound was obtained as a white solid.

$^1$H-NMR (CDCl$_3$)$\delta_{TMS}$:1.63-1.76(m, 3H), 1.89-2.05(m, 3H), 2.29-2.36(m, 2H), 2.57-2.73(m, 4H), 2.88(m, 1H), 3.03 (m, 1H), 3.85(s, 3H), 3.88(m, 1H), 4.36(m, 1H), 6.73 (dd, J=2.8, 8.3 Hz, 1H), 6.99(d, J=8.3 Hz), 7.06-7.11(m, 3H), 7.32(d, J=7.6 Hz, 1H), 7.42(d, J=2.7 Hz, 1H), 9.02(brs, 1H)
FAB-MS (M+H)$^+$:378

Example 40

1-[1-(8-methoxy-1,2,3,4-tetrahydronaphthalen-1-yl) piperidin-4-yl]-1,3-dihydro-2H-benzimidazol-2-one

Example 41

1-[(1-chroman-4-yl)piperidin-4-yl]-1,3-dihydro-2H-benzimidazol-2-one

In the same manner as in Example 1 and using 4-chromanol, the title compound was obtained as a white solid.

$^1$H-NMR (CDCl$_3$)$\delta_{TMS}$:1.75-1.79(m, 1H), 1.89-1.92(m, 1H), 1.97-2.15(m, 2H), 2.25-2.37(m, 2H), 2.57(m, 1H), 2.76-2.85(m, 2H), 3.03(m, 1H), 3.99(m, 1H), 4.11-4.16(m, 1H), 4.18-4.41(m, 2H), 6.80 (dd, J=0.9, 8.1 Hz, 1H), 6.94(dt, J=1.0, 7.4 Hz), 7.06-7.15(m, 4H), 7.30(d, J=7.1 Hz, 1H), 7.60(d, J=7.6 Hz, 1H), 8.87(brs, 1H)

FAB-MS (M+H)$^+$:350

Example 42

1-[(1-thiochroman-4-yl)piperidin-4-yl]-1,3-dihydro-2H-benzimidazol-2-one

Example 43

1-[(1,1-dioxide-3,4-dihydro-2H-thiochromen-4-yl) piperidin-4-yl]-1,3-dihydro-2H-benzimidazol-2-one

Example 44

1-[1-(5-cyano-1,2,3,4-tetrahydronaphthalen-1-yl) piperidin-4-yl]-1,3-dihydro-2H-benzimidazol-2-one

Example 45

1-[1-(5-acetoamino-1,2,3,4-tetrahydronaphthalen-1-yl)piperidin-4-yl]-1,3-dihydro-2H-benzimidazol-2-one The compounds of the following Examples 46-74 can be synthesized using the compounds obtained above and in the same manner as in Example 2.

Example 46

2-{3-[1-(5-methoxy-1,2,3,4-tetrahydronaphthalen-1-yl)piperidin-4-yl]-2,3-dihydro-2-oxo-benzimidazol-1-yl}-N-methylacetamide In the same manner as in Example 2 and using 1-[1-(5-methoxy-1,2,3,4-tetrahydronaphthalen-1-yl)piperidin-4-yl]-1,3-dihydro-2H-benzimidazol-2-one, the title compound was obtained as a white solid.

$^1$H-NMR (CDCl$_3$)$\delta_{TMS}$:1.63-1.73(m, 3H), 1.88-2.05(m, 3H), 2.23-2.35(m, 2H), 2.46-2.71(m, 3H), 2.78-2.88(m, 5H), 3.02(m, 1H), 3.89(d, J=4.0 Hz, 1H), 3.89(m, 1H), 4.34(m, 1H), 4.50(d, J=3.7 Hz, 2H), 6.14(brs, 1H), 6.72(m, 1H), 7.04-7.21(m, 4H), 7.36(m, 1H), 7.46(m, 1H)

FAB-MS (M+H)$^+$:449

Example 47

2-{3-[1-(5-trifluoromethyl-1,2,3,4-tetrahydronaphthalen-1-yl)piperidin-4-yl]-2,3-dihydro-2-oxo-benzimidazol-1-yl}-N-methylacetamide

Example 48

2-{3-[1-(5-bromo-1,2,3,4-tetrahydronaphthalen-1-yl)piperidin-4-yl]-2,3-dihydro-2-oxo-benzimidazol-1-yl}-N-methylacetamide

Example 49

2-{3-[1-(5-fluoro-1,2,3,4-tetrahydronaphthalen-1-yl)piperidin-4-yl]-2,3-dihydro-2-oxo-benzimidazol-1-yl}-N-methylacetamide

Example 50

2-{3-[1-(1,2,3,4-tetrahydronaphthalen-1-yl)piperidin-4-yl]-2,3-dihydro-2-oxo-benzimidazol-1-yl}-N,N-dimethylacetamide

Example 51

2-{3-[1-(1,2,3,4-tetrahydronaphthalen-1-yl)piperidin-4-yl]-2,3-dihydro-2-oxo-benzimidazol-1-yl}acetamide

Example 52

2-{3-[1-(1,2,3,4-tetrahydronaphthalen-1-yl)piperidin-4-yl]-2,3-dihydro-2-oxo-benzimidazol-1-yl}-N-ethylacetamide

Example 53

2-{3-[1-(5-cyano-1,2,3,4-tetrahydronaphthalen-1-yl)piperidin-4-yl]-2,3-dihydro-2-oxo-benzimidazol-1-yl}-N-methylacetamide

Example 54

2-{3-[1-(5-acetylamino-1,2,3,4-tetrahydronaphthalen-1-yl)piperidin-4-yl]-2,3-dihydro-2-oxo-benzimidazol-1-yl}-N-methylacetamide

Example 55

2-{3-[1-(8-fluoro-1,2,3,4-tetrahydronaphthalen-1-yl)piperidin-4-yl]-2,3-dihydro-2-oxo-benzimidazol-1-yl}-N-methylacetamide

Example 56

2-{3-[1-(6-fluoro-1,2,3,4-tetrahydronaphthalen-1-yl)piperidin-4-yl]-2,3-dihydro-2-oxo-benzimidazol-1-yl}-N-methylacetamide

Example 57

2-{3-[1-(7-fluoro-1,2,3,4-tetrahydronaphthalen-1-yl)piperidin-4-yl]-2,3-dihydro-2-oxo-benzimidazol-1-yl}-N-methylacetamide In the same manner as in Example 2 and using (RS)-1-[1-(7-fluoro-1,2,3,4-tetrahydronaphthalen-1-yl)piperidin-4-yl]-1,3-dihydro-2H-benzimidazol 2-one, the title compound was obtained as a white solid.

$^1$H-NMR (CDCl$_3$)$\delta_{TMS}$:1.64-1.78(m, 3H), 1.89-2.03(m, 3H), 2.29-2.36(m, 2H), 2.57-2.72(m, 4H), 2.80(d, J=4.9 Hz, 3H), 2.85-2.91(m, 1H), 3.02(m, 1H), 3.87(m, 1H), 4.36(m, 1H), 4.51(s, 2H), 6.13(brs, 1H), 6.85(m, 1H), 7.00-7.08(m, 2H), 7.12-7.21(m, 2H), 7.36(d, J=7.4 Hz), 7.54(dd, J=2.6, 10.6 Hz, 1H)

FAB-MS (M+H)$^+$:437

Example 58

2-{3-[1-(6-methyl-1,2,3,4-tetrahydronaphthalen-1-yl)piperidin-4-yl]-2,3-dihydro-2-oxo-benzimidazol-1-yl}-N-methylacetamide

Example 59

2-{3-[1-(7-methyl-1,2,3,4-tetrahydronaphthalen-1-yl)piperidin-4-yl]-2,3-dihydro-2-oxo-benzimidazol-1-yl}-N-methylacetamide

Example 60

2-{3-[1-(6-methoxy-1,2,3,4-tetrahydronaphthalen-1-yl)piperidin-4-yl]-2,3-dihydro-2-oxo-benzimidazol-1-yl}-N-methylacetamide

Example 61

2-{3-[1-(7-methoxy-1,2,3,4-tetrahydronaphthalen-1-yl)piperidin-4-yl]-2,3-dihydro-2-oxo-benzimidazol-1-yl}-N-methylacetamide In the same manner as in Example 2 and using 1-[1-(7-methoxy-1,2,3,4-tetrahydronaphthalen-1-yl)piperidin-4-yl]-1,3-dihydro-2H-benzimidazol-2-one, the title compound was obtained as a white solid.

$^1$H-NMR (CDCl$_3$)$\delta_{TMS}$:1.64-1.76(m, 3H), 1.92-2.01(m, 3H), 2.28-2.36(m, 2H), 2.73(d, J=7.9 Hz, 3H), 2.78-2.89(m, 1H), 3.02(m, 1H), 3.84(s, 3H), 3.88(m, 1H), 4.35(m, 1H), 4.50(s, 2H), 6.14(brs, 1H), 6.73(m, 1H), 6.99-7.16(m, 4H), 7.34(m, 1H), 7.40(m, 1H)

FAB-MS (M+H)$^+$:449

Example 62

2-{3-[1-(8-methoxy-1,2,3,4-tetrahydronaphthalen-1-yl)piperidin-4-yl]-2,3-dihydro-2-oxo-benzimidazol-1-yl}-N-methylacetamide

Example 63

1-[2-(methylamino)ethyl]-3-[1-(1,2,3,4-tetrahydronaphthalen-1-yl)piperidin-4-yl]-1,3-dihydro-2H-benzimidazol-2-one

Example 64

1-[2-(dimethylamino)ethyl]-3-[1-(1,2,3,4-tetrahydronaphthalen-1-yl)piperidin-4-yl]-1,3-dihydro-2H-benzimidazol-2-one

Example 65

1-(2-methoxyethyl)-3-[1-(1,2,3,4-tetrahydronaphthalen-1-yl)piperidin-4-yl]-1,3-dihydro-2H-benzimidazol-2-one

Example 66

2-{3-[1-(1,2,3,4-tetrahydronaphthalen-1-yl)piperidin-4-yl]-2,3-dihydro-2-oxo-benzimidazol-1-yl}-N-cyclopropylacetamide

Example 67

2-{3-[1-(1-chroman-4-yl)piperidin-4-yl]-2,3-dihydro-2-oxo-benzimidazol-1-yl}-N-methylacetamide In the same manner as in Example 2 and using 1-[(1-chroman-4-yl)piperidin-4-yl]-1,3-dihydro-2H-benzimidazol-2-one, the title compound was obtained as a white solid.
$^1$H-NMR (CDCl$_3$)$\delta_{TMS}$:1.75-1.78(m, 1H), 1.89-1.92(m, 1H), 1.97-2.14(m, 2H), 2.24-2.37(m, 2H), 2.55-2.62(m, 1H), 2.75-2.86(m, 5H), 3.02-3.05(m, 1H), 3.99(m, 1H), 4.13-4.19(m, 1H), 4.33-4.42(m, 2H), 4.51(s, 2H), 6.12(brs, 1H), 6.80(d, J=8.2 Hz, 1H), 6.94(dt, J=0.9, 7.4 Hz, 1H), 7.05-7.18(m, 4H), 7.34(m, 1H), 7.59(d, J=7.7 Hz, 1H)
FAB-MS (M+H)$^+$:421

Example 68

2-{3-[1-(1-thiochroman-4-yl)piperidin-4-yl]-2,3-dihydro-2-oxo-benzimidazol-1-yl}-N-methylacetamide

Example 69

2-{3-[1-(1,1-dioxide-3,4-dihydro-2H-thiochromen-4-yl)piperidin-4-yl]-2,3-dihydro-2-oxo-benzimidazol-1-yl}-N-methylacetamide

Example 70

2-{3-[1-(5-ethyl-1,2,3,4-tetrahydronaphthalen-1-yl)piperidin-4-yl]-2,3-dihydro-2-oxo-benzimidazol-1-yl}-N-methylacetamide

Example 71

2-{3-[1-(8-methyl-1,2,3,4-tetrahydronaphthalen-1-yl)piperidin-4-yl]-2,3-dihydro-2-oxo-benzimidazol-1-yl}-N-methylacetamide

Example 72

2-{3-[1-(1,2,3,4-tetrahydronaphthalen-1-yl)piperidin-4-yl]-2,3-dihydro-6-fluoro-2-oxo-benzimidazol-1-yl}-N-methylacetamide

Example 73

2-{3-[1-(1,2,3,4-tetrahydronaphthalen-1-yl)piperidin-4-yl]-2,3-dihydro-2-oxo-benzimidazol-1-yl}acetic acid

Example 74

2-{3-[1-(1,2,3,4-tetrahydronaphthalen-1-yl)piperidin-4-yl]-2,3-dihydro-2-thioxo-benzimidazol-1-yl}-N-methylacetamide

Example 75

1-[1-(1,2,2a,3,4,5-hexahydroacenaphthylen-1-yl)piperidin-4-yl]-1,3-dihydro-2H-benzimidazol-2-one (1) 1,2,2a,3,4,5-hexahydroacenaphthylen-1-ylamine To a solution of ethyl (1,2,3,4-tetrahydronaphthalen-1-yl)acetate (31.0 g) in ethanol (100 ml) was added sodium hydroxide (4N, 100 ml), and the mixture was stirred at room temperature for 1 hr. The reaction mixture was concentrated to a half volume under reduced pressure, and the residue was washed with ethyl acetate. The aqueous layer was acidified with dilute hydrochloric acid, and extracted with chloroform. The obtained organic layer was washed with water and saturated brine, dried over magnesium sulfate, and filtered. The solvent was evaporated under reduced pressure to give (1,2,3,4-tetrahydronaphthalen-1-yl)acetic acid.

To (1,2,3,4-tetrahydronaphthalen-1-yl)acetic acid was added polyphosphoric acid (75%, 150 g), and the mixture was stirred at 100° C. for 1.5 hr. The reaction mixture was poured into ice water, and the mixture was extracted with ethyl acetate. The obtained organic layer was washed with water and saturated brine, dried over magnesium sulfate, and filtered, and the solvent was evaporated under reduced pressure. The obtained residue was purified by silica gel column chromatography (hexane/ethyl acetate) to give 2a,3,4,5-tetrahydro-2H-acenaphthylen-1-one (12.1 g, 37%) as a white solid.

2a,3,4,5-Tetrahydro-2H-acenaphthylen-1-one (4.85 g) was dissolved in methanol (70 ml). Sodium borohydride (1.07 g) was added to the solution under ice-cooling, and the mixture was stirred at room temperature for 1 hr. The reaction mixture was poured into water, and the mixture was extracted with ethyl acetate. The extract was washed with water and saturated brine, dried over magnesium sulfate, and concentrated to give 2a,3,4,5-tetrahydro-2H-acenaphthylen-1-ol.

To a cooled (0° C.) solution of 2a,3,4,5-tetrahydro-2H-acenaphthylen-1-ol and diphenylphosphoryl azide (9.31 g) in toluene (90 ml) was added DBU (diazabicycloundecene) (5.04 mL), and the mixture was stirred at room temperature for 3 hr. The reaction mixture was poured into water, and the mixture was extracted with toluene. The combined organic layer was washed with water, dried over magnesium sulfate, and concentrated. The crude product was dissolved in a mixed solvent (77 ml) of THF/water (10:1), triphenylphosphine (9.61 g) was added, and the mixture was heated under reflux for 1 hr. After cooling to room temperature, the solvent was evaporated, 1N hydrochloric acid (100 ml) was added to the residue, and unnecessary substances were removed by extraction with ethyl acetate. The aqueous phase was alkalified with potassium carbonate, and extracted with chloroform. The extract was washed with water and saturated brine, dried over magnesium sulfate, and concentrated to give 1,2,2a,3,4,5-hexahydroacenaphthylen-1-ylamine.

(2) 1-(1,2,2a,3,4,5-hexahydroacenaphthylen-1-yl)piperidin-4-one

To a mixture of 1,2,2a,3,4,5-hexahydroacenaphthylen-1-ylamine, potassium carbonate (3.89 g) and ethanol (60 ml) was added 1-ethyl-1-methyl-4-oxopiperidinium iodide (8.36 g) dissolved in water (15 ml), and the mixture was heated under reflux for 2 hr. The reaction mixture was poured into water, and the mixture was extracted with ethyl acetate. The extract was washed with water and saturated brine, dried over magnesium sulfate, and concentrated. The obtained residue was purified by silica gel column chromatography (hexane/ethyl acetate) to give 1-(1,2,2a,3,4,5-hexahydroacenaphthylen-1-yl)piperidin-4-one (1.01 g, 14%) as an oil.

(3) 1-[1-(1,2,2a,3,4,5-hexahydroacenaphthylen-1-yl)piperidin-4-yl]-1,3-dihydro-2H-benzimidazol-2-one To a cooled (0° C.) solution of 1-(1,2,2a,3,4,5-hexahydroacenaphthylen-1-yl)piperidin-4-one (1.00 g, 3.92 mmol) and 1,2-phenylenediamine (642 mg) in dichloroethane (30 ml) were added sodium triacetoxyborohydride (1.99 g) and acetic acid (0.509 ml), and the mixture was stirred at room temperature for 19 hr. The reaction mixture was poured into water, and the mixture was neutralized with potassium carbonate, and extracted with chloroform. The extract was washed with water and saturated brine, dried over sodium sulfate, and concentrated. The obtained residue was purified by silica gel column chromatography (chloroform/methanol) to give N-[1-(1,2,2a,3,4,5-hexahydroacenaphthylen-1-yl)piperidin-4-yl]-benzene-1,2-diamine (1.16 g) as an oil.

N-[1-(1,2,2a,3,4,5-Hexahydroacenaphthylen-1-yl)piperidin-4-yl]-benzene-1,2-diamine (1.15 g) was dissolved in THF (70 ml), 1,1'-carbonyldiimidazole (0.591 g) was added, and the mixture was stirred at room temperature for 3 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (0.76 g) as a white solid.

$^1$H-NMR (CDCl$_3$)$\delta_{TMS}$:9.10(s, 1H), 7.30-7.00(m, 7H), 4.40-4.30(m, 1H), 4.06(d, J=7.8 Hz, 1H), 3.20-3.00(m, 3H), 2.97-2.62(m, 2H), 2.60-2.34(m, 5H), 2.20-2.00(m, 2H), 1.90-1.60(m, 6H), 1.18-1.00(m, 2H).

FAB-MS (M+H)$^+$:374

Example 76

2-{3-[1-(1,2,2a,3,4,5-hexahydroacenaphthylen-1-yl)piperidin-4-yl]-2,3-dihydro-2-oxo-benzimidazol-1-yl}-N-methylacetamide N-[1-(1,2,2a,3,4,5-Hexahydroacenaphthylen-1-yl)piperidin-4-yl]-1,3-dihydro-2H-benzimidazol 2-one (0.30 g) was dissolved in DMF (15 ml). Sodium hydride (35 mg, 60%) was added, and the suspension was stirred at room temperature for 30 min. Ethyl bromoacetate (0.1 ml) was added, and the mixture was stirred for 1 hr. The reaction mixture was poured into water, and the mixture was extracted with ethyl acetate. The extract was washed with water and saturated aqueous ammonium chloride solution, dried over magnesium sulfate, and concentrated to give ethyl {3-[1-(1,2,2a,3,4,5-hexahydroacenaphthylen-1-yl)piperidin-4-yl]-2,3-dihydro-2-oxo-benzimidazol-1-yl} acetate. 40% Methylamine-methanol solution (20 ml) was added, the mixture was stirred at room temperature for 1 hr, and the reaction mixture was concentrated under reduced pressure. The obtained residue was purified by silica gel column chromatography (chloroform/methanol) to give the title compound (333 mg) as a white powder.

$^1$H-NMR (DMSO-d$_6$)$\delta_{TMS}$:8.10-8.00(m, 1H), 7.30-6.90 (m, 7H), 4.39(s, 2H), 4.25-4.05(m, 1H), 3.93(d, J=7.5 Hz, 1H), 3.10-2.75(m, 4H), 2.60-2.52(m, 3H), 2.40-1.50(m, 6H), 1.10-0.90(m, 2H).

FAB-MS (M+H)$^+$:445

Example 77

1-[1-(1,2,2a,3,4,5-hexahydroacenaphthylen-1-yl)piperidin-4-yl]-1,3-dihydro-2H-benzimidazol-2-one (stereoisomer of Example 75)

(1) 1,2,2a,3,4,5-hexahydroacenaphthylen-1-ylamine (stereoisomer of Example 75(1))

To a mixture of 2a,3,4,5-tetrahydro-2H-acenaphthylen-1-one (12.2 g, 70.9 mmol), hydroxylamine hydrochloride (7.85 g) and water (90 ml) were slowly added sodium acetate (14.5 g), methanol (120 ml), THF (30 ml) and water (60 ml) with stirring while heating at 75° C., and the mixture was stirred for 2 hr and 40 min. After cooling to room temperature, methanol was evaporated under reduced pressure, and the obtained precipitate was collected by filtration, and washed with water to give 2a,3,4,5-tetrahydro-2H-acenaphthylen-1-one oxime (13.5 g).

To 2a,3,4,5-tetrahydro-2H-acenaphthylen-1-one oxime (7.00 g) was added a solution (about 65%, 50 ml) of sodium bis(2-methoxyethoxy)aluminum dihydride in toluene, and the mixture was stirred with heating at 80° C. for 2 hr. After cooling to room temperature, the reaction mixture was poured into ice water, and the mixture was extracted with chloroform. After concentration under reduced pressure, the residue was extracted with 1N hydrochloric acid. The aqueous layer was alkalified with potassium carbonate, and extracted with chloroform. The extract was washed with saturated brine, dried over sodium sulfate, and concentrated under reduced pressure to give the title compound (5.34 g, 83%).

(2) 1-[1-(1,2,2a,3,4,5-hexahydroacenaphthylen-1-yl)piperidin-4-yl]-1,3-dihydro-2H-benzimidazol-2-one (stereoisomer of Example 75)

In the same manner as Example 75(2) and (3) and using 1,2,2a,3,4,5-hexahydroacenaphthylen-1-ylamine (stereoisomer of Example 75(1)), the title compound was obtained as a white solid.

$^1$H-NMR (CDCl$_3$)$\delta_{TMS}$:9.17(bs, 1H), 7.40-6.95(m, 6H), 4.57-4.37(m, 2H), 3.21-3.06(m, 1H), 2.91-1.50(m, 16H), 1.30-1.15(m, 1H).

FAB-MS (M+H)$^+$:374

Example 78

2-{3-[1-(1,2,2a,3,4,5-hexahydroacenaphthylen-1-yl)piperidin-4-yl]-2,3-dihydro-2-oxo-benzimidazol-1-yl}-N-methylacetamide (stereoisomer of Example 76)

In the same manner as Example 76 and using 1-[1-(1,2,2a,3,4,5-hexahydroacenaphthylen-1-yl)piperidin-4-yl]-1,3-dihydro-2H-benzimidazol-2-one (stereoisomer of Example 75), the title compound was obtained as a white solid.

$^1$H-NMR (DMSO-d$_6$)$\delta_{TMS}$:8.10-8.05(m, 1H), 7.38-6.92 (m, 7H), 4.40(s, 2H), 4.26-4.08(m, 1H), 3.18-2.99(m, 1H), 2.82-2.58(m, 8H), 2.44-1.95(m, 6H), 1.80-1.05(m, 5H).

FAB-MS (M+H)$^+$:445

Example 79

(1RS,3aSR)-2-{3-[1-(2,3,3a,4,5,6-hexahydro-1H-phenalen-1-yl)piperidin-4-yl]-2,3-dihydro-2-oxo-benzimidazol-1-yl}-N-methylacetamide In the same manner as Example 76 and using (1RS,3aSR)-1-[1-{(2,3,3a,4,5,6-hexahydro-1H-phenalen-1-yl)piperidin-4-yl}-1,3-dihydro-2H-benzimidazol-2-one (see WO2005/028466, Example 1), the title compound was obtained as a white solid.

The obtained (1RS,3aSR)-2-{3-[1-(2,3,3a,4,5,6-hexahydro-1H-phenalen-1-yl)piperidin-4-yl]-2,3-dihydro-2-oxo-benzimidazol-1-yl}-N-methylacetamide was resolved into (+) form and (−) form by optical resolution using HPLC.
optical resolution analysis conditions
column: CHIRALPAK$^{(R)}$AD-H
size: 0.46 cm I.D.×25 cm
mobile phase: hexane/ethanol/diethylamine=70/30/0.1(v/v)
flow rate: 1.0 ml/min
temperature: 40° C.
wavelength: 283 nm
Isomer 1) $^1$H-NMR (CDCl$_3$)$\delta_{TMS}$:7.60-7.53(m, 1H), 7.39-7.32(m, 1H), 7.21-6.95(m, 5H), 6.13(bs, 1H), 4.51(s, 2H), 4.41-4.29(m, 1H), 3.87-3.80(m, 1H), 3.08-2.97(m, 1H), 2.90-2.73(m, 7H), 2.68-2.20(m, 4H), 2.11-1.20(m, 15H), 0.92-0.82(m, 2H).
FAB-MS (M+H)$^+$:459
$[\alpha]_D$=−36.6° (c0.24, MeOH)
Isomer 2) $^1$H-NMR (CDCl$_3$)$\delta_{TMS}$:7.60-7.53(m, 1H), 7.39-7.32(m, 1H), 7.21-6.95(m, 5H), 6.12(bs, 1H), 4.51(s, 2H), 4.41-4.29(m, 1H), 3.87-3.80(m, 1H), 3.08-2.97(m, 1H), 2.90-2.73(m, 7H), 2.68-2.20(m, 4H), 2.11-1.20(m, 15H), 0.92-0.82(m, 2H).
FAB-MS (M+H)$^+$:459
$[\alpha]_D$=+37.2° (c0.24, MeOH)

Example 80

(1RS,3aRS)-2-{3-[1-(2,3,3a,4,5,6-hexahydro-1H-phenalen-1-yl)piperidin-4-yl]-2,3-dihydro-2-oxo-benzimidazol-1-yl}-N-methylacetamide In the same manner as Example 76 and using (1RS,3aRS)-1-[1-(2,3,3a,4,5,6-hexahydro-1H-phenalen-1-yl)piperidin-4-yl]-1,3-dihydro-2H-benzimidazol-2-one (see WO2005/028466, Example 1), the title compound was obtained as a white solid.

The obtained (1RS,3aRS) form was resolved into (+) form and (−) form by optical resolution using HPLC.
optical resolution analysis conditions
column: CHIRALRAI0$^1$) IA
size: 0.46 cm I.D.×25 cm
mobile phase: hexane/ethanol/diethylamine=60/40/0.1(v/v)
flow rate: 1.0 ml/min
temperature: 40° C.
wavelength: 283 nm
Isomer 1) $^1$H-NMR (CDCl$_3$)$\delta_{TMS}$:7.67-7.48(m, 1H), 7.40-7.30(m, 1H), 7.20-6.95(m, 5H), 6.12(bs, 1H), 4.51(s, 2H), 4.40-4.29(m, 1H), 4.05-3.95(m, 1H), 3.08-2.97(m, 1H), 2.87-2.70(m, 7H), 2.67-2.51(m, 2H), 2.42-2.25(m, 2H), 2.10-1.70 (m, 8H), 1.55-1.20(m, 5H).
FAB-MS (M+H)$^+$:459
$[\alpha]_D$=+54.6° (c0.14, CDCl$_3$)
Isomer 2) $^1$H-NMR (CDCl$_3$)$\delta_{TMS}$:7.67-7.48(m, 1H), 7.40-7.30(m, 1H), 7.20-6.95(m, 5H), 6.13(bs, 1H), 4.51(s, 2H), 4.40-4.29(m, 1H), 4.05-3.95(m, 1H), 3.08-2.97(m, 1H), 2.87-2.70(m, 7H), 2.67-2.51(m, 2H), 2.42-2.25(m, 2H), 2.10-1.70 (m, 8H), 1.55-1.20(m, 5H).
FAB-MS (M+H)$^+$:459
$[\alpha]_D$=−58.3° (c0.13, MeOH)

Example 81

1-[1-(2,3,3a,4,5,6-hexahydrobenzo[de]chromen-6-yl)piperidin-4-yl]-1,3-dihydro-2H -benzimidazol-2-one (1) 3,3a,4,5-tetrahydro-2H-benzo[de]chromen-6-one To a suspension of lithium aluminum hydride (3.45 g) in THF (400 ml) was added dropwise a solution of ethyl chroman-4-ylacetate (10.0 g) in THF (50 ml) under ice-cooling, and the mixture was stirred at room temperature for 1 hr. To the reaction mixture were added water (3.45 ml), 15% aqueous sodium hydroxide solution (3.45 ml) and water (10 ml), and the mixture was filtered, washed with ethyl acetate, and concentrated under reduced pressure to give chroman-4-ylmethanol (7.58 g).

To chroman-4-ylmethanol (15.0 g), methylene chloride (80 ml) and triethylamine (12.9 ml) was added dropwise methanesulfonyl chloride (6.85 ml) under ice-cooling, and the mixture was stirred for 2 hr. The reaction mixture was poured into water, and the mixture was extracted with methylene chloride. The extract was washed with water and saturated brine, dried over magnesium sulfate, and concentrated to give chroman-4-ylmethyl methanesulfonate.

To a solution of chroman-4-ylmethyl methanesulfonate in ethanol (650 ml) was added potassium cyanide (9.23 g), and the mixture was stirred with heating under reflux for 15 hr. After cooling to room temperature, the mixture was concentrated under reduced pressure, water was added to the obtained residue, and the mixture was extracted with ethyl acetate. The extract was washed with water and saturated brine, dried over magnesium sulfate, and concentrated to give 3-chroman-4-ylpropionitrile.

A mixture of 3-chroman-4-ylpropionitrile, ethanol (150 ml) and 50% sodium hydroxide (100 ml) was stirred with heating under reflux for 26 hr. After cooling to room temperature, the mixture was washed with ether, and the aqueous layer was acidified with 4N hydrochloric acid, and extracted with chloroform. The extract was washed with water and saturated brine, dried over magnesium sulfate, and concentrated to give 3-chroman-4-ylpropionic acid (9.96 g).

To 3-chroman-4-ylpropionic acid (9.95 g) was added polyphosphoric acid (75%, 150 g), and the mixture was stirred at 100° C. for 1.5 hr. The reaction mixture was poured into ice water, and the mixture was extracted with ethyl acetate. The obtained organic layer was washed with water and saturated brine, dried over magnesium sulfate, and filtered, and the solvent was evaporated under reduced pressure. The obtained residue was purified by silica gel column chromatography (hexane/ethyl acetate) to give 3,3a,4,5-tetrahydro-2H-benzo[de]chromen-6-one (4.03 g, 44%) as a yellow solid.

(2) 2,3,3a,4,5,6-hexahydro-2H-benzo[de]chromen-6-ylamine

In the same manner as Example 75(1) and using 3,3a,4,5-tetrahydro-2H-benzo[de]chromen-6-one, the title compound was obtained as a white solid.

(3) 1-[1-(2,3,3a,4,5,6-hexahydro-benzo[de]chromen-6-yl)piperidin-4-yl]-1,3-dihydro-2H-benzimidazol-2-one In the same manner as Example 75(2) and (3) and using 2,3,3a,4,5,6-hexahydro-2H-benzo[de]chromen-6-ylamine, the title compound was obtained as a white solid.

¹H-NMR (CDCl₃)δ$_{TMS}$:9.47(s, 1H), 7.35-7.25(m, 2H), 7.13-7.03(m, 4H), 6.67(d, J=8.1 Hz, 1H), 4.43-4.32(m, 2H), 4.13(t, J=10.8 Hz, 1H), 3.88(d, J=6.9 Hz, 1H), 3.05-2.50(m, 5H), 2.40-2.15(m, 3H), 2.05-1.60(m, 7H), 1.18-1.05(m, 1H).
FAB-MS (M+H)⁺:390

Example 82

2-{3-[1-(2,3,3a,4,5,6-hexahydro-benzo[de]chromen-6-yl)piperidin-4-yl]-2,3-dihydro-2-oxo-benzimidazol-1-yl}-N-methylacetamide In the same manner as Example 76 and using 1-[1-(2,3,3a,4,5,6-hexahydro-benzo[de]chromen-6-yl)piperidin-4-yl]-1,3-dihydro-2H-benzimidazol-2-one, the title compound was obtained as a white solid.
¹H-NMR (CDCl₃)δ$_{TMS}$:7.36-7.23(m, 2H), 7.20-7.00(m, 4H), 6.67(d, J=7.8 Hz, 1H), 6.16(bs, 1H), 4.50(s, 2H), 4.45-4.23(m, 2H), 4.22-4.09(m, 1H), 3.90-3.83(m, 1H), 3.06-2.50 (m, 8H), 2.40-1.60(m, 9H), 1.25-1.05(m, 1H).
FAB-MS (M+H)⁺:461

Example 83

1-[1-(1,2,2a,3,4,5-hexahydroacenaphthylen-5-yl)piperidin-4-yl]-1,3-dihydro-2H-benzimidazol-2-one (1) 1,2,2a,3,4,5-hexahydroacenaphthylen-5-ylamine In the same manner as Example 75(1) and using ethyl indan-1-ylacetate, 2,2a,3,4-tetrahydro-1H-acenaphthylen-5-one was obtained as a white solid.
In the same manner as Example 75(1) and using the obtained 2,2a,3,4-tetrahydro-1H-acenaphthylen-5-one, the title compound was obtained as a white solid.

(2) 1-[1-(1,2,2a,3,4,5-hexahydroacenaphthylen-5-yl)piperidin-4-yl]-1,3-dihydro-2H-benzimidazol-2-one In the same manner as Example 75(2) and (3) and using 1,2,2a,3,4,5-hexahydroacenaphthylen-5-ylamine, the title compound was obtained as a white solid.
Isomer 1) ¹H-NMR(CDCl₃)δ$_{TMS}$:9.48(bs, 1H), 7.53-7.45 (m, 1H), 7.38-7.00(m, 6H), 4.40-4.23(m, 1H), 3.93(d, J=7.8 Hz, 1H), 3.03-2.07(m, 12H), 1.97-1.83(m, 1H), 1.73-1.45(m, 4H), 1.07-0.98(m, 1H).
FAB-MS (M+H)⁺:373
Isomer 2) ¹H-NMR (CDCl₃)δ$_{TMS}$:9.29(bs, 1H), 7.50-7.00 (m, 7H), 4.50-4.30(m, 1H), 4.17-4.00(m, 1H), 3.10-2.00(m, 12H), 1.94-1.20(m, 7H).
FAB-MS (M+H)⁺:373

Example 84

2-{3-[1-(1,2,2a,3,4,5-hexahydroacenaphthylen-5-yl)piperidin-4-yl]-2,3-dihydro-2-oxo-benzimidazol-1-yl}-N-methylacetamide In the same manner as Example 76 and using 1-[1-(1,2,2a,3,4,5-hexahydroacenaphthylen-5-yl)piperidin-4-yl]-1,3-dihydro-2H-benzimidazol-2-one, the title compound was obtained as a white solid.

Isomer 1) ¹H-NMR (CDCl₃)δ$_{TMS}$:7.50-7.37(m, 2H), 7.21-7.03(m, 5H), 6.12(bs, 1H), 4.51(s, 2H), 4.41-4.30(m, 1H), 4.10-4.00(m, 1H), 3.10-2.77(m, 9H), 2.67-2.03(m, 6H), 1.93-1.25(m, 6H).
FAB-MS (M+H)⁺:445
Isomer 2) ¹H-NMR (CDCl₃)δ$_{TMS}$:7.57-7.50(m, 1H), 7.46-7.02(m, 6H), 6.15(bs, 1H), 4.50(s, 2H), 4.40-4.25(m, 1H), 4.00-3.90(m, 1H), 3.17-2.10(m, 15H), 1.95-1.47(m, 5H), 1.17-0.98(m, 1H).
FAB-MS (M+H)⁺:445

Example 85

1-[2-(cyclopropylmethylamino)ethyl]-3-[1-(1,2,2a,3,4,5-hexahydroacenaphthylen-1-yl)piperidin-4-yl]-1,3-dihydro-2H-benzimidazol-2-one 1-[1-(1,2,2a,3,4,5-Hexahydroacenaphthylen-1-yl)piperidin-4-yl]-1,3-dihydro-2H-benzimidazol 2-one (1.00 g) was dissolved in DMF (30 ml), 60% sodium hydride (140 mg) was added, and the suspension was stirred for 1 hr. Then, N-(2-bromoethyl)phthalimide (818 mg) was added, and the mixture was stirred at 100° C. for 1 hr. The reaction mixture was cooled to room temperature, and poured into saturated aqueous ammonium chloride solution, and the mixture was extracted with ethyl acetate. The extract was washed with water and saturated brine, dried over magnesium sulfate, and concentrated. The obtained residue was purified by silica gel column chromatography (hexane/ethyl acetate) to give 2-{2-{3-[1-(1,2,2a,3,4,5-hexahydroacenaphthylen-1-yl)piperidin-4-yl]-1,3-dihydro-2-oxobenzimidazol-1-yl}ethyl}isoindole-1,3-dione.
2-{2-{3-[1-(1,2,2a,3,4,5-Hexahydroacenaphthylen-1-yl)piperidin-4-yl]-1,3-dihydro-2-oxobenzimidazol-1-yl}ethyl}isoindole-1,3-dione, ethanol (35 ml) and hydrazine (0.42 ml) were stirred with heating under reflux for 2 hr. After cooling to room temperature, the solvent was evaporated, and the residue was purified by silica gel column chromatography (chloroform/methanol) to give 1-(2-aminoethyl)-3-[1-(1,2,2a,3,4,5-hexahydroacenaphthylen-1-yl)piperidin-4-yl]-1,3-dihydro-2-oxobenzimidazol-2-one (420 mg, 38%) as an oil.
1-(2-Aminoethyl)-3-[1-(1,2,2a,3,4,5-hexahydroacenaphthylen-1-yl)piperidin-4-yl]-1,3-dihydro-2-oxobenzimidazol-2-one (210 mg) was dissolved in dichloroethane (10 ml), and cyclopropanecarboxyaldehyde (41 μL), sodium triacetoxyborohydride (0.248 g) and acetic acid (0.032 ml) were added. The mixture was stirred at room temperature for 13 hr, the reaction mixture was poured into saturated aqueous sodium hydrogen carbonate solution, and the mixture was extracted with chloroform. The extract was washed with saturated brine, dried over anhydrous sodium sulfate, and concentrated. The obtained residue was purified by silica gel column chromatography (chloroform/methanol) to give the title compound (80 mg, 34%) as an oil.
¹H-NMR (CDCl₃)δ$_{TMS}$:7.42-7.38(m, 1H), 7.22-6.95(m, 6H), 4.56-4.37(m, 2H), 4.09-3.95(m, 2H), 3.20-3.10(m, 1H), 3.01(t, J=6.9 Hz, 2H), 2.90-1.50(m, 19H), 1.37-1.13(m, 2H), 1.00-0.83(m, 1H), 0.50-0.37(m, 2H), 0.17-0.08(m, 2H).
FAB-MS (M+H)⁺:471

Example 86

1-[1-(1,2,2a,3,4,5-hexahydroacenaphthylen-1-yl)piperidin-4-yl]-3-(2-isopropylaminoethyl)-1,3-dihydro-2H-benzimidazol-2-one In the same manner as Example 85 and using acetone instead of cyclopropanecarboxyaldehyde, the title compound was obtained as an oil.

$^1$H-NMR (CDCl$_3$)$\delta_{TMS}$:7.41-7.37(m, 1H), 7.22-6.91(m, 5H), 4.50-4.37(m, 2H), 3.99(t, J=6.9 Hz, 2H), 3.20-1.50(m, 21H), 1.05(d, J=6.0 Hz, 6H).
FAB-MS (M+H)$^+$:459

Example 87

3-{3-{3-[1-(1,2,2a,3,4,5-hexahydroacenaphthylen-5-yl)piperidin-4-yl]-2,3-dihydro-2-oxo-benzimidazol-1-yl}propyl}thiazolidine-2,4-dione To 1-[1-(1,2,2a,3,4,5-hexahydroacenaphthylen-5-yl)piperidin-4-yl]-1,3-dihydro-2H-benzimidazol-2-one (500 mg), dimethylacetamide (3 ml) and potassium carbonate (370 mg) was added 3-bromopropanol (0.242 ml), and the mixture was stirred with heating at 85° C. for 2 hr. The reaction mixture was cooled to room temperature, water was added, and the precipitate was collected by filtration to give 1-[1-(1,2,2a,3,4,5-hexahydroacenaphthylen-5-yl)piperidin-4-yl]-3-(3-hydroxypropyl)-1,3-dihydro-2H-benzimidazol-2-one.

1-[1-(1,2,2a,3,4,5-Hexahydroacenaphthylen-5-yl)piperidin-4-yl]-3-(3-hydroxypropyl)-1,3-dihydro-2H-benzimidazol-2-one and 2,4-thiazolidinedione (314 mg) were dissolved in THF (25 ml), 40% solution (1.22 ml) of triphenylphosphine (702 mg) and diethyl azodicarboxylate (DEAD) in toluene was added, and the mixture was stirred at 50° C. for 2 hr. The reaction mixture was concentrated under reduced pressure, and the obtained residue was purified by silica gel column chromatography (hexane/ethyl acetate) to give the title compound (160 mg).

$^1$H-NMR (CDCl$_3$)$\delta_{TMS}$:12.3(bs, 1H), 9.20(bs, 1H), 7.63-7.42(m, 2H), 7.38-7.20(m, 2H), 7.20-7.03(m, 2H), 7.00-6.92 (m, 1H), 4.85(d, J=6.3 Hz, 1H), 4.78-4.58(m, 1H), 4.00-3.85 (m, 3H), 3.81(s, 2H), 3.66(t, J=6.9 Hz, 2H), 3.30-2.70(m, 8H), 2.68-1.80(m, 8H), 1.70-1.25(m, 2H)(trifluoroacetate).
FAB-MS (M+H)$^+$:531

Example 88

1-[1-(6-fluoro-1,2,2a,3,4,5-hexahydroacenaphthylen-1-yl)piperidin-4-yl]-1,3-dihydro-2H-benzimidazol-2-one (1) 6-fluoro-2a,3,4,5-tetrahydro-2H-acenaphthylen-1-one To a solution of 2-fluorophenethylalcohol (25.0 g) in triethylamine (37.5 ml) and methylene chloride (250 ml) was added dropwise methanesulfonyl chloride (16.7 ml) under ice-cooling, and the mixture was stirred for 30 min. The reaction mixture was warmed to room temperature, washed with water and saturated brine, dried over anhydrous magnesium sulfate, and concentrated to give 2-(2-fluorophenyl) ethyl methanesulfonate.

To a suspension of 60% sodium hydride (8.24 g) in DMF (200 ml) was added dropwise dimethyl malonate (24.9 g) under ice-cooling, and the suspension was stirred at 50° C. for 30 min. After cooling to room temperature, a solution of 2-(2-fluorophenyl)ethyl methanesulfonate in DMF (30 ml) was added dropwise, and the mixture was stirred at 150° C. for 1 hr. After cooling to room temperature, the reaction mixture was poured into ice water, and the mixture was extracted with ethyl acetate. The extract was washed with water and saturated brine, dried over magnesium sulfate, and concentrated under reduced pressure to give dimethyl 2-[2-(2-fluorophenyl)ethyl]malonate.

Dimethyl 2-[2-(2-fluorophenyl)ethyl]malonate, sodium hydroxide (22.7 g), ethanol (150 ml) and water (100 ml) were heated under reflux for 1.5 hr. The reaction mixture was concentrated under reduced pressure, and the residue was acidified with hydrochloric acid, and extracted with chloroform. The extract was washed with water and saturated brine, dried over magnesium sulfate, and concentrated under reduced pressure to give 4-(2-fluorophenyl)butanoic acid.

To 4-(2-fluorophenyl)butanoic acid was added polyphosphoric acid (75%, 100 g), and the mixture was stirred at 150° C. for 1.5 hr. The reaction mixture was poured into ice water, and the mixture was extracted with ethyl acetate. The obtained organic layer was washed with water and saturated brine, dried over magnesium sulfate, and filtered, and the solvent was evaporated under reduced pressure. The obtained residue was purified by silica gel column chromatography (hexane/ethyl acetate) to give 5-fluoro-3,4-dihydro-2H-naphthalen-1-one (10.2 g, 33%) as an oil.

To a suspension of 60% sodium hydride (4.12 g) in toluene (200 ml) was added dropwise ethyl diethylphosphonoacetate (20.4 ml) under ice-cooling, and the mixture was stirred at room temperature for 45 min. Then, a solution of 5-fluoro-3,4-dihydro-2H-naphthalen-1-one (15.3 g) in toluene (50 ml) was added dropwise, and the mixture was stirred at 80° C. for 2 hr. After cooling to room temperature, the reaction mixture was poured into ice water, and the mixture was extracted with toluene. The extract was washed with water and saturated brine, dried over magnesium sulfate, and concentrated under reduced pressure. The obtained residue was purified by silica gel column chromatography (hexane/ethyl acetate) to give ethyl (5-fluoro-3,4-dihydro-2H-naphthalen-1-ylidene)acetate.

Ethyl (5-fluoro-3,4-dihydro-2H-naphthalen-1-ylidene)acetate, 10% palladium carbon catalyst (3 g) and ethanol (150 ml) were stirred under a hydrogen atmosphere for 4 hr. The reaction mixture was filtered through celite, and concentrated to give ethyl (5-fluoro-1,2,3,4-tetrahydronaphthalen-1-yl)acetate.

To a solution of ethyl 5-fluoro-1,2,3,4-tetrahydronaphthalen-1-yl)acetate in ethanol (30 ml) was added sodium hydroxide (4N, 30 ml), and the mixture was stirred at room temperature for 2 hr. The reaction mixture was concentrated to ½ under reduced pressure, and the residue was washed with ethyl acetate. The aqueous layer was acidified with dilute hydrochloric acid, and extracted with chloroform. The obtained organic layer was washed with water and saturated brine, dried over magnesium sulfate, and filtered, and the solvent was evaporated under reduced pressure to give (5-fluoro-1,2,3,4-tetrahydronaphthalen-1-yl)acetic acid.

To the obtained (5-fluoro-1,2,3,4-tetrahydronaphthalen-1-yl)acetic acid was added polyphosphoric acid (75%, 100 g), and the mixture was stirred at 120° C. for 1 hr. The reaction mixture was poured into ice water, and the mixture was extracted with ethyl acetate. The obtained organic layer was washed with water and saturated brine, dried over magnesium sulfate, and filtered, and the solvent was evaporated under reduced pressure. The obtained residue was purified by silica gel column chromatography (hexane/ethyl acetate) to give 6-fluoro-2a,3,4,5-tetrahydro-2H-acenaphthylen-1-one (6.70 g, 34%) as an orange solid.

(2) 6-fluoro-1,2,2a,3,4,5-hexahydroacenaphthylen-1-ylamine

In the same manner as Example 75(1) and using 6-fluoro-2a,3,4,5-tetrahydro-2H-acenaphthylen-1-one, the title compound was obtained as an oil.

(3) 1-[1-(6-fluoro-1,2,2a,3,4,5-hexahydroacenaphthylen-1-yl)piperidin-4-yl]-1,3-dihydro-2H-benzimidazol 2-one In the same manner as Example 75(2) and (3) and using 6-fluoro-1,2,2a,3,4,5-hexahydroacenaphthylen-1-ylamine, the title compound was obtained as an oil.

¹H-NMR (CDCl₃)δ$_{TMS}$:9.14(bs, 1H), 7.35-6.80(m, 6H), 4.42-4.27(m, 1H), 4.00(d, J=7.5 Hz, 1H), 3.18-2.97(m, 3H), 2.96-2.80(m, 1H), 2.70-2.30(m, 6H), 2.20-2.03(m, 2H), 1.87-1.63(m, 4H), 1.20-1.00(m, 1H).

FAB-MS (M+H)⁺:392

Example 89

2-{3-[1-(6-fluoro-1,2,2a,3,4,5-hexahydroacenaphthylen-1-yl)piperidin-4-yl]-2,3-dihydro-2-oxo-benzimidazol-1-yl}-N-methylacetamide In the same manner as Example 76 and using 1-[1-(6-fluoro-1,2,2a,3,4,5-hexahydroacenaphthylen-1-yl)piperidin-4-yl]-1,3-dihydro-2H-benzimidazol-2-one, the title compound was obtained as an oil.

¹H-NMR (DMSO-d₆)δ$_{TMS}$:8.13-8.05(m, 1H), 7.30-7.22 (m, 1H), 7.20-7.13(m, 1H), 7.07-6.83(m, 4H), 4.40(s, 2H), 4.25-4.10(m, 1H), 3.92(d, J=7.6 Hz, 2H), 3.50-3.30(m, 2H), 3.20-2.72(m, 4H), 2.59(d, J=4.8 Hz, 3H), 2.40-2.00(m, 6H), 1.80-1.52(m, 4H), 1.10-0.93(m, 1H).

FAB-MS (M+H)⁺:463

In the same manner as in the above-mentioned Examples 75-89, the compounds of the following Examples 90-102 can be obtained.

Example 90

2-{3-[1-(1,2,2a,3,4,5-hexahydroacenaphthylen-1-yl)piperidin-4-yl]-2,3-dihydro-2-oxo-benzimidazol-1-yl}-N-ethylacetamide

Example 91

2-{3-[1-(1,2,2a,3,4,5-hexahydroacenaphthylen-1-yl)piperidin-4-yl]-2,3-dihydro-2-oxo-benzimidazol-1-yl}-N-dimethylacetamide

Example 92

2-{3-[1-(8-fluoro-1,2,2a,3,4,5-hexahydroacenaphthylen-5-yl)piperidin-4-yl]-2,3-dihydro-2-oxo-benzimidazol-1-yl}-N-methylacetamide

Example 93

2-{3-[1-(1,2,2a,3,4,5-hexahydroacenaphthylen-5-yl)piperidin-4-yl]-2,3-dihydro-2-oxo-benzimidazol-1-yl}-N-ethylacetamide

Example 94

2-{3-[1-(7-fluoro-2,3,3a,4,5,6-hexahydro-1H-phenalen-1-yl)piperidin-4-yl]-2,3-dihydro-2-oxo-benzimidazol-1-yl}-N-methylacetamide

Example 95

2-{3-[1-(7-methyl-2,3,3a,4,5,6-hexahydro-1H-phenalen-1-yl)piperidin-4-yl]-2,3-dihydro-2-oxo-benzimidazol-1-yl}-N-methylacetamide

Example 96

2-{6-fluoro-3-[1-(2,3,3a,4,5,6-hexahydro-1H-phenalen-1-yl)piperidin-4-yl]-2,3-dihydro-2-oxo-benzimidazol-1-yl}-N-methylacetamide

Example 97

1-[1-(2,3,3a,4,5,6-hexahydro-1H-phenalen-1-yl)piperidin-4-yl]-3-(2-isopropylaminoethyl)-1,3-dihydro-2H-benzimidazol-2-one

Example 98

1-[1-(2,3,3a,4,5,6-hexahydro-1H-phenalen-1-yl)piperidin-4-yl]-3-(2-cyclopropylaminoethyl)-1,3-dihydro-2H-benzimidazol-2-one

Example 99

1-[1-(1,2,2a,3,4,5-hexahydroacenaphthylen-5-yl)piperidin-4-yl]-3-(2-oxo-2-pyrrolidin-1-ylethyl)-1,3-dihydro-2H-benzimidazol-2-one

Example 100

2-{3-[1-(9-fluoro-2,3,3a,4,5,6-hexahydro-benzo[de]chromen-6-yl)piperidin-4-yl]-2,3-dihydro-2-oxo-benzimidazol-1-yl}-N-methylacetamide

Example 101

2-{3-[1-(1,2,3,7,8,9,10,10a-octahydrocyclohepta[de]naphthalen-6-yl)piperidin-3-yl]-2,3-dihydro-2-oxo-benzimidazol-1-yl}-N-methylacetamide

Example 102

2-{3-[1-(2,6,7,8,9,9a-hexahydrobenzo[cd]azulen-6-yl)piperidin-4-yl]-2,3-dihydro-2-oxo-benzimidazol-1-yl}-N-methylacetamide

Example 103

(R)-1-[1-(5-fluoroacenaphthen-1-yl)piperidin-4-yl]-1,3-dihydro-2H-benzimidazol-2-one (1) To 4-fluoro-1-naphthylacetic acid (18 g) were added thionyl chloride (70 ml) and N,N-dimethylformamide (several drops), and the mixture was heated under reflux for 1 hr. The reaction mixture was concentrated under reduced pressure, and dichloromethane (1200 ml) was dissolved in the obtained residue. Aluminum chloride (23.5 g) was added under ice-cooling, and the mixture was stirred at room temperature for 2 hr. The reaction mixture was poured into ice water, and the mixture was extracted with chloroform. The extract was washed with water and saturated brine, dried over sodium sulfate, and concentrated. The residue was purified by silica gel column chromatography to give 5-fluoroacenaphthen-1-one (9.4 g).
$^1$H-NMR (CDCl$_3$)$\delta_{TMS}$:3.79(s, 2H), 7.24(dd, 1H), 7.35-7.40(m, 1H), 7.77(t, 1H), 7.78(d, 1H), 8.24(d, 1H)

(2) To a cooled (−30° C.) solution of (R)-2-methyl-CBS-oxazaborolidine (3.0 ml, 1M toluene solution) was added borane-THF complex (14 ml, 1M THF solution), and the mixture was stirred for 45 min. A solution of 5-fluoroacenaphthen-1-one (2.5 g) in dichloromethane (30 ml) was added dropwise, and the mixture was cooled to and stirred at −30° C. for 1 hr. Then, methanol (8 ml) and 1N hydrochloric acid were added under ice-cooling, and the mixture was extracted with chloroform. The extract was washed with water and saturated aqueous sodium chloride solution, dried over sodium sulfate, and concentrated to give (S)-5-fluoro-1-acenaphthenol (2.55 g).
$^1$H-NMR (CDCl$_3$)$\delta_{TMS}$:2.07(brs, 1H), 3.20(d, 1H), 3.76 (dd, 1H), 5.70-5.80(m, 1H), 7.20-7.35(m, 2H), 7.55-7.65(m, 2H), 7.90(dd, 1H)

(3) To a solution of (S)-5-fluoro-1-acenaphthenol (2.3 g, 12.2 mmol) and diphenylphosphoryl azide (4.4 g, 16 mmol) in toluene (25 ml) was added DBU (2.44 g), and the mixture was stirred at room temperature for 3 hr. The reaction mixture was poured into water, and the mixture was extracted with toluene. The combined organic layer was washed with 1N hydrochloric acid, dried over magnesium sulfate, and concentrated. A crude azide form product obtained by purification by silica gel column chromatography was dissolved in a mixed solvent (25 ml) of THF/water (10/1). Triphenylphosphine (2.7 g) was added, and the mixture was stirred at room temperature for 18 hr. The solvent was evaporated, 1N hydrochloric acid (200 ml) was added to the residue, and unnecessary substances were removed by extraction with ethyl acetate. The aqueous phase was alkalified with potassium carbonate, and extracted with chloroform. The extract was dried over sodium sulfate, and concentrated to give a amino form crude product. The crude amino form product (1.35 g) was dissolved in ethanol (15 ml). 1-Ethyl-1-methyl-4-oxopiperidinium iodide (2.35 g) dissolved in potassium carbonate (180 mg) and water (5 ml) was added, and the mixture was heated under reflux for 1 hr. The reaction mixture was poured into water, and the mixture was extracted with ethyl acetate. The extract was washed with water and saturated brine, dried over magnesium sulfate, and concentrated. The obtained residue was purified by silica gel column chromatography (chloroform/methanol) to give (R)-1-(5-fluoroacenaphthen-1-yl)-piperidin-4-one (630 mg).
$^1$H-NMR (CDCl$_3$)$\delta_{TMS}$:2.40-2.55(m, 4H), 2.65-2.75(m, 2H), 2.85-2.95(m, 2H), 3.25-3.45(m, 2H), 5.05-5.15(m, 1H), 7.05-7.20(m, 2H), 7.50-7.60(m, 2H), 7.85(d, 1H)

(4) To a cooled (0° C.) solution of (R)-1-(5-fluoroacenaphthen-1-yl)-piperidin-4-one (630 mg) and 1,2-phenylenediamine (510 mg) in THF (100 ml) were added sodium triacetoxyborohydride (1.35 g) and acetic acid (0.6 ml), and the mixture was stirred at room temperature for 12 hr. The reaction mixture was poured into water, and the mixture was neutralized with potassium carbonate, and extracted with chloroform. The extract was washed with water and saturated brine, dried over sodium sulfate, and concentrated. The obtained residue was purified by silica gel column chromatography (chloroform/methanol) to give (R)-N-[1-(5-fluoro-acenaphthen-1-yl)piperidin-4-yl]-benzene-1,2-diamine (1.08 g). The obtained diamine form (1.08 g) was dissolved in THF (10 ml), carbonyldiimidazole (600 mg) was added, and the mixture was stirred at room temperature for 2 hr. The reaction mixture was poured into water, and the mixture was extracted with chloroform. The extract was washed with water and saturated aqueous sodium chloride solution, dried over sodium sulfate, and concentrated. The obtained residue was purified by silica gel column chromatography (chloroform/methanol) and recrystallized from a mixed solvent of ethyl acetate/diisopropylether to give the title compound (1.1 g) as a white solid.
$^1$H-NMR (CDCl$_3$)$\delta_{TMS}$:1.70-1.90(m, 2H), 2.35-2.60(m, 4H), 2.75-2.85(m, 1H), 2.95-3.10(m, 1H), 3.38(d, 2H), 4.27-4.40(m, 1H), 5.00-5.08(m, 1H), 7.00-7.40(m, 5H), 7.25-7.35 (m, 1H), 7.55-7.60(m, 2H), 7.80-7.90(m, 1H), 9.85(brs, 1H)
FAB-MS (M+H)$^+$:388

Example 104

(R)-2-{3-[1-(5-fluoroacenaphthen-1-yl)piperidin-4-yl]-2,3-dihydro-2-oxo-benzimidazol-1-yl}-N-methylacetamide.maleate (R)-1-[1-(5-Fluoroacenaphthen-1-yl)piperidin-4-yl]-1,3-dihydro-2H-benzimidazol-2-one (1.1 g) was dissolve in THF (20 ml). Sodium hydride (150 mg, 60%) was added, and the suspension was stirred at 40° C. for 20 min. After cooling to room temperature, ethyl bromoacetate (550 mg) was added, and the mixture was stirred at 45° C. for 30 min. Then, methylamine (40% methanol solution, 27 ml) was added at room temperature, and the mixture was stirred for 40 min. After confirmation of disappearance of the ester form, the reaction mixture was poured into water, and the mixture was extracted with chloroform. The extract was washed with water and saturated aqueous sodium chloride solution, dried over sodium sulfate, and concentrated to give a crude product (1.36 g) of (R)-2-{3-[1-(5-fluoroacenaphthen-1-yl)piperidin-4-yl]-2,3-dihydro-2-oxo-benzimidazol-1-yl}-N-methylacetamide. The obtained crude product was treated with 1.1 equivalents of maleic acid to give the title compound (950 mg).
$^1$H-NMR (DMSO-d$_6$)$\delta_{TMS}$:1.80-2.00(m, 2H), 2.59(s, 3H), 2.50-2.70(m, 1H), 2.80-3.80(m, 7H), 4.42(s, 2H), 4.45-4.60 (m, 1H), 5.50-5.60(m, 1H), 6.07(s, 2H), 7.00-7.15(m, 3H), 7.30-7.48(m, 3H), 7.75-7.80(m, 1H), 7.88(brs, 1H), 7.99(d, 1H), 8.05-8.15(m, 1H)
FAB-MS (M+H)$^+$:459
$[\alpha]_D^{20}$=+26.4°

Example 105

1-[1-(5-fluoroacenaphthen-1-yl)piperidin-4-yl]-1,3-dihydro-2H-benzimidazol-2-one 5-Fluoroacenaphthen-1-one (1.9 g) was dissolved in methanol (40 ml), sodium borohydride (470 mg) was added, and the mixture was stirred at room temperature for 40 min. To the reaction mixture was gradually added aqueous ammonium chloride solution, and the mixture was extracted with ethyl acetate. The extract was washed with saturated sodium chloride, dried over anhydrous magnesium sulfate, and concentrated under reduced pressure to give 5-fluoro-1-acenaphthenol (1.8 g). The obtained alcohol form (1.56 g) was dissolved in chloroform (12 ml). Thionyl chloride (2 ml) was added under ice-cooling, and the mixture was heated under reflux for 1 hr. The solvent was evaporated, and the obtained residue was dissolved in N,N-dimethylformamide (20 ml). 4-(2-Keto-1-benzimidazolinyl)piperidine (1.4 g), potassium carbonate (3.4 g) and sodium iodide (1.3 g) were added, and the mixture was stirred at 145° C. for 40 min. After allowing to cool, the reaction mixture was extracted with ethyl acetate, and the extract was washed with saturated sodium chloride, dried over anhydrous magnesium sulfate, and concentrated under reduced pressure. The residue was purified by silica gel chromatography, and recrystallized from ethyl acetate to give the title compound (690 mg).

$^1$H-NMR (CDCl$_3$)$\delta_{TMS}$:1.70-1.90(m, 2H), 2.35-2.60(m, 4H), 2.75-2.85(m, 1H), 2.95-3.10(m, 1H), 3.38(d, 2H), 4.27-4.40(m, 1H), 5.00-5.08(m, 1H), 7.00-7.40(m, 5H), 7.25-7.35(m, 1H), 7.55-7.60(m, 2H), 7.80-7.90(m, 1H), 9.85(brs, 1H)
FAB-MS (M+H)$^+$:388

Example 106

2-{3-[1-(5-fluoroacenaphthen-1-yl)piperidin-4-yl]-2,3-dihydro-2-oxo-benzimidazol-1-yl}-N-methylacetamide.3/2 maleate A crude product obtained in the same manner as Example 104 and using 1-[1-(5-fluoroacenaphthen-1-yl)piperidin-4-yl]-1,3-dihydro-2H-benzimidazol-2-one (700 mg) was treated with 1.5 equivalents of maleic acid to give the title compound (420 mg).

$^1$H-NMR (DMSO-d$_6$)$\delta_{TMS}$:1.80-2.00(m, 2H), 2.59(s, 3H), 2.55-2.80(m, 2H), 3.00-3.60(m, 5H), 3.70-3.90(m, 2H), 4.42(s, 2H), 4.50-4.65(m, 1H), 5.60-5.68(m, 1H), 6.12(s, 3H), 7.00-7.15(m, 3H), 7.30-7.35(d, 1H), 7.37-7.48(m, 1H), 7.78-7.85(m, 1H), 7.83(d, 1H), 7.90(d, 1H), 8.08-8.15(m, 1H)
FAB-MS (M+H)$^+$:459

Example 107

1-[1-(3-chloroacenaphthen-1-yl)piperidin-4-yl]-1,3-dihydro-2H-benzimidazol-2-one (1) To a mixture (11 g) of 2-chloro-1-naphthylacetic acid and 7-chloro-1-naphthylacetic acid were added thionyl chloride (50 ml) and N,N-dimethylformamide (several drops), and the mixture was heated under reflux for 1 hr. The reaction mixture was concentrated under reduced pressure, and the obtained residue was dissolved in dichloromethane (500 ml). Aluminum chloride (13 g) was added under ice-cooling, and the mixture was stirred at room temperature for 3 hr. The reaction mixture was poured into ice water, and the mixture was extracted with chloroform. The extract was washed with water and saturated brine, dried over sodium sulfate, and concentrated. The residue was isolated and purified by silica gel column chromatography to give 3-chloroacenaphthen-1-one (600 mg) and 8-chloro-acenaphthen-1-one (3.0 g).
3-chloroacenaphthen-1-one
$^1$H-NMR (CDCl$_3$)$\delta_{TMS}$:3.82(s, 2H), 7.26(d, 1H), 7.54(t, 1H), 7.70(d, 1H), 7.98(d, 1H), 8.07(d, 1H)
8-chloroacenaphthen-1-one
$^1$H-NMR (CDCl$_3$)$\delta_{TMS}$:3.84(s, 2H), 7.25(d, 1H), 7.49(d, 1H), 7.55-7.65(m, 2H), 7.80(d, 1H), 8.08(d, 1H)
(2) 3-Chloroacenaphthen-1-one (1.0 g) was dissolved in methanol (25 ml), sodium borohydride (220 mg) was added, and the mixture was stirred at room temperature for 1 hr. To the reaction mixture was gradually added aqueous ammonium chloride solution, and the mixture was extracted with ethyl acetate. The extract was washed with saturated brine, dried over anhydrous magnesium sulfate, and concentrated under reduced pressure to give 3-chloro-1-acenaphthenol (1.0 g). The alcohol form (1.0 g) was dissolved in chloroform (15 ml). Thionyl chloride (2 ml) was added under ice-cooling, and the mixture was heated under reflux for 1 hr. The solvent was evaporated, and the obtained residue was dissolved in N,N-dimethylformamide (12 ml). 4-(2-Keto-1-benzimidazolinyl)piperidine (900 mg), potassium carbonate (2.2 g) and sodium iodide (800 mg) were added, and the mixture was stirred at 145° C. for 1 hr. After allowing to cool, the reaction mixture was extracted with ethyl acetate, and the extract was washed with saturated brine, dried over anhydrous magnesium sulfate, and concentrated under reduced pressure. The residue was purified by silica gel chromatography, and recrystallized from ethyl acetate to give the title compound (1.0 g).

$^1$H-NMR (CDCl$_3$)$\delta_{TMS}$:1.70-1.90(m, 2H), 2.35-2.65(m, 4H), 2.70-2.80(m, 1H), 3.00-3.10(m, 1H), 3.35-3.45(m, 2H), 4.30-4.40(m, 1H), 4.90-5.00(m, 1H), 7.00-7.15(m, 3H), 7.25-7.35(m, 1H), 7.49(d, 1H), 7.50-7.60(m, 3H), 7.70(d, 1H), 9.60(brs, 1H)
FAB-MS (M+H)$^+$:404

Example 108

2-{3-[1-(3-chloroacenaphthen-1-yl)piperidin-4-yl]-2,3-dihydro-2-oxo-benzimidazol-1-yl}-N-methylacetamide.1/2 fumarate A crude product obtained in the same manner as Example 104 and using 1-[1-(3-chloroacenaphthen-1-yl)piperidin-4-yl]-1,3-dihydro-2H-benzimidazol-2-one (1.3 g) was treated with 1.0 equivalent of fumaric acid to give the title compound (277 mg).

$^1$H-NMR (DMSO-d$_6$)$\delta_{TMS}$:1.60-1.80(m, 2H), 2.25-2.60(m, 5H), 2.60(s, 3H), 2.90-3.05(m, 1H), 3.15-3.55(m, 3H), 4.25-4.40(m, 1H), 4.41(s, 2H), 5.00-5.10(m, 1H), 6.62(s, 1H), 7.00-7.15(m, 2H), 7.30(d, 1H), 7.48(d, 1H), 7.55-7.65(m, 2H), 7.74(d, 1H), 7.75-7.85(m, 1H), 8.05-8.15(m, 1H)
FAB-MS (M+H)$^+$:475

Example 109

1-[1-(5-chloroacenaphthen-1-yl)piperidin-4-yl]-1,3-dihydro-2H-benzimidazol-2-one (1) Acenaphthen-1-one (11 g) was dissolved in N,N-dimethylformamide (80 ml), N-chlorosuccinimide (9.0 g) was added, and the mixture was stirred at room temperature for 2 days. The reaction mixture was extracted with ethyl acetate, and the extract was washed with saturated sodium chloride, dried over anhydrous magnesium sulfate, and concentrated under reduced pressure. The residue was purified by silica gel chromatography, and recrystallized from ethanol to give crude crystals (3.5 g) of 5-chloro-acenaphthen-1-one.
(2) 5-Chloroacenaphthen-1-one (1.9 g) was dissolved in methanol (35 ml), sodium borohydride (430 mg) was added, and the mixture was stirred at room temperature for 1 hr. To the reaction mixture was gradually added aqueous ammonium chloride solution, and the mixture was extracted with ethyl acetate. The extract was washed with saturated brine, dried over anhydrous magnesium sulfate, and concentrated under reduced pressure to give 5-chloro-1-acenaphthenol (1.9 g).

$^1$H-NMR (CDCl$_3$)$\delta_{TMS}$:1.80-2.30(brs, 1H), 3.20(d, 1H), 3.77(dd, 1H), 5.70-5.75(m, 1H), 7.21(d, 1H), 7.52(d, 1H), 7.55-7.60(m, 1H), 7.66(dd, 1H), 7.99(d, 1H)

(3) The alcohol form (1.9 g) was dissolved in chloroform (20 ml). Thionyl chloride (3 ml) was added under ice-cooling, and the mixture was heated under reflux for 1 hr. The solvent was evaporated, and N,N-dimethylformamide (20 ml) was dissolved in the obtained residue. 4-(2-Keto-1-benzimidazolinyl)piperidine (1.7 g), potassium carbonate (4.14 g) and sodium iodide (1.5 g) were added, and the mixture was stirred at 140° C. for 1 hr. After allowing to cool, the reaction mixture was extracted with ethyl acetate, and the extract was washed with saturated sodium chloride, dried over anhydrous magnesium sulfate, and concentrated under reduced pressure. The residue was purified by silica gel chromatography to give the title compound (1.1 g).

$^1$H-NMR (DMSO$_6$)$\delta_{TMS}$:1.50-1.70(m, 2H), 2.25-2.60(m, 5H), 2.90-3.00(m, 1H), 3.30-3.40(m, 2H), 4.05-4.20(m, 1H), 4.95-5.00(m, 1H), 6.90-7.00(m, 3H), 7.23(d, 1H), 7.33(d, 1H), 7.62(m, 2H), 7.73(dd, 1H), 7.86(d, 1H), 10.82(brs, 1H)

FAB-MS (M+H)$^+$:404

Example 110

2-{3-[1-(5-chloroacenaphthen-1-yl)piperidin-4-yl]-2, 3-dihydro-2-oxo-benzimidazol-1-yl}-N-methylacetamide A crude product obtained in the same manner as Example 104 and using 1-[1-(5-chloroacenaphthen-1-yl)piperidin-4-yl]-1,3-dihydro-2H-benzimidazol-2-one (1.3 g) was washed by suspending in acetone to give the title compound (237 mg).

$^1$H-NMR (DMSO-d$_6$)$\delta_{TMS}$:1.60-1.75(m, 2H), 2.25-2.65 (m, 5H), 2.59(s, 3H), 2.90-3.00(m, 1H), 3.30-3.40(m, 2H), 4.10-4.20(m, 1H), 4.41(s, 2H), 4.95-5.05(m, 1H), 7.00-7.10 (m, 3H), 7.25-7.35(m, 2H), 7.55-7.65(m, 2H), 7.70-7.80(dd, 1H), 7.80-7.90(d, 1H), 8.05-8.15(brs, 1H)

FAB-MS (M+H)$^+$:475

Example 111

1-[1-(8-chloroacenaphthen-1-yl)piperidin-4-yl]-1,3-dihydro-2H-benzimidazol-2-one.hydrochloride (1) 8-Chloroacenaphthen-1-one (2.0 g, 9.87 mmol) was dissolved in methanol (40 ml), sodium borohydride (400 mg) was added, and the mixture was stirred at room temperature for 1 hr. To the reaction mixture was gradually added aqueous ammonium chloride solution, and the mixture was extracted with ethyl acetate. The extract was washed with saturated brine, dried over anhydrous magnesium sulfate, and concentrated under reduced pressure to give 8-chloro-1-acenaphthenol (2.0 g).

$^1$H-NMR (CDCl$_3$)$\delta_{TMS}$:1.50-1.60(brs, 1H), 3.30(d, 1H), 3.79(dd, 1H), 5.70-5.80(m, 1H), 7.34(d, 1H), 7.42(d, 1H), 7.48(dd, 1H), 7.63(d, 1H), 7.69(d, 1H)

(2) The alcohol form (2.0 g) was dissolved in chloroform (18 ml). Thionyl chloride (2 ml) was added under ice-cooling, and the mixture was heated under reflux for 1 hr. The solvent was evaporated, and the obtained residue was dissolved in N,N-dimethylformamide (20 ml). 4-(2-Keto-1-benzimidazolinyl)piperidine (1.7 g), potassium carbonate (4.14 g) and sodium iodide (1.5 g) were added, and the mixture was stirred at 140° C. for 1 hr. After allowing to cool, the reaction mixture was extracted with ethyl acetate, and the extract was washed with saturated sodium chloride, dried over anhydrous magnesium sulfate, and concentrated under reduced pressure. The residue was purified by silica gel chromatography to give crude crystals (2.1 g) of (RS)-1-[1-(8-chloroacenaphthen-1-yl)piperidin-4-yl]-1,3-dihydro-2H-benzimidazol-2-one. The crude crystals were treated with 4N hydrochloric acid-ethyl acetate solution and recrystallized from acetone to give the title compound (305 mg).

$^1$H-NMR (DMSO$_6$)$\delta_{TMS}$: 1.65-1.75(m, 1H), 1.90-2.00(m, 1H), 2.60-2.75(m, 1H), 2.80-3.15(m, 3H), 3.60-3.75(m, 1H), 3.80-3.90(m, 2H), 4.05-4.20(m, 1H), 3.50-3.65(m, 1H), 5.55-5.70(m, 1H), 6.90-7.00(m, 3H), 7.50-7.60(m, 1H), 7.60-7.75 (m, 3H), 7.84(d, 1H), 8.05(d, 1H), 10.92(brs, 1H), 11.67(brs, 1H)

FAB-MS (M+H)$^+$:404

Example 112

2-{3-[1-(8-chloroacenaphthen-1-yl)piperidin-4-yl]-2, 3-dihydro-2-oxo-benzimidazol-1-yl}-N-methylacetamide-oxalate A crude product obtained in the same manner as Example 104 and using 1-[1-(8-chloroacenaphthen-1-yl)piperidin-4-yl]-1,3-dihydro-2H-benzimidazol-2-one (1.2 g) was treated with 1.1 equivalents of oxalic acid to give the title compound (473 mg).

$^1$H-NMR (DMSO-d$_6$)$\delta_{TMS}$:1.55-1.65(m, 1H), 1.70-1.80 (m, 1H), 2.60(s, 3H), 2.25-2.70(m, 5H), 3.05-3.15(m, 1H), 3.35-3.45(m, 1H), 3.55-3.65(m, 1H), 4.20-4.30(m, 1H), 4.40 (s, 2H), 5.15-5.25(m, 1H), 7.00-7.10(m, 3H), 7.26(d, 1H), 7.43(d, 1H), 7.50-7.60(m, 2H), 7.73(d, 1H), 7.85(d, 1H), 8.10(brs, 1H)

FAB-MS (M+H)$^+$:475

Example 113

1-[1-(5-bromoacenaphthen-1-yl)piperidin-4-yl]-1,3-dihydro-2H-benzimidazol-2-one (1) Acenaphthen-1-one (25 g) was dissolved in N,N-dimethylformamide (200 ml), N-bromosuccinimide (27 g) was added, and the mixture was stirred at room temperature for 2 days. The precipitated crystals were collected by filtration, and recrystallized from ethanol to give 5-bromoacenaphthen-1-one (16 g).

$^1$H-NMR (CDCl$_3$)$\delta_{TMS}$:3.79(s, 2H), 7.33(d, 1H), 7.80-7.90(m, 2H), 8.01(d, 1H), 8.28(d, 1H)

(2) 5-Bromoacenaphthen-1-one (5.3 g) was dissolved in methanol (80 ml), sodium borohydride (1.0 g) was added, and the mixture was stirred at room temperature for 1 hr. To the reaction mixture was gradually added aqueous ammonium chloride solution, and the mixture was extracted with ethyl acetate. The extract was washed with saturated brine, dried over anhydrous magnesium sulfate, and concentrated under reduced pressure to give 5-bromo-1-acenaphthenol (4.4 g).

$^1$H-NMR (CDCl$_3$)$\delta_{TMS}$:1.60-1.80(brs, 1H), 3.19(d, 1H), 3.76(dd, 1H), 5.74(d, 1H), 7.17(d, 1H), 7.60(d, 1H), 7.67(dd, 1H), 7.72(d, 1H), 7.94(d, 1H)

(3) The alcohol form (4.4 g) was dissolved in chloroform (40 ml). Thionyl chloride (5 ml) was added under ice-cooling, and the mixture was heated under reflux for 1 hr. The solvent was evaporated, and the obtained residue was dissolved in N,N-dimethylformamide (40 ml). 4-(2-Keto-1-benzimidazolinyl)piperidine (3.2 g), potassium carbonate (7.0 g) and sodium iodide (2.65 g) were added, and the mixture was stirred at 140° C. for 1 hr. After allowing to cool, the reaction mixture was extracted with ethyl acetate, and the extract was washed with saturated brine, dried over anhydrous magnesium sulfate, and concentrated under reduced pressure. The residue was purified by silica gel chromatography to give crude crystals (8.0 g). The crude crystals (300 mg) were washed by suspending in acetone to give the title compound (121 mg).

¹H-NMR (CDCl₃)δ$_{TMS}$:1.70-1.90(m, 2H), 2.35-2.60(m, 4H), 2.70-2.80(m, 1H), 3.00-3.10(m, 1H), 3.35-3.40(m, 2H), 4.25-4.40(m, 1H), 4.95-5.05(m, 1H), 7.00-7.10(m, 3H), 7.17 (d, 1H), 7.25-7.35(m, 1H), 7.59(d, 1H), 7.60-7.70(m, 2H), 7.89(d, 1H), 8.78(brs, 1H)
FAB-MS (M+H)⁺:450

Example 114

2-{3-[1-(5-bromoacenaphthen-1-yl)piperidin-4-yl]-2,3-dihydro-2-oxo-benzimidazol-1-yl}-N-methylacetamide A crude product obtained in the same manner as Example 104 and using 1-[1-(5-bromoacenaphthen-1-yl)piperidin-4-yl]-1,3-dihydro-2H-benzimidazol-2-one (1.2 g) was washed by suspending in acetone to give the title compound (597 mg).
¹H-NMR (DMSO-d₆)δ$_{TMS}$:1.50-1.75(m, 2H), 2.20-2.60 (m, 5H), 2.59(s, 3H), 2.90-3.00(m, 1H), 3.30-3.45(m, 1H), 4.00-4.40(m, 2H), 4.42(s, 2H), 4.95-5.05(m, 1H), 6.85-7.10 (m, 3H), 7.25-7.35(m, 2H), 7.63(d, 1H), 7.70-7.85(m, 3H), 8.19(m, 1H)
FAB-MS (M+H)⁺:521

Example 115

1-[1-(3-bromoacenaphthen-1-yl)piperidin-4-yl]-1,3-dihydro-2H-benzimidazol-2-one (1) To a mixture (43 g) of 2-bromo-1-naphthylacetic acid and 7-bromo-1-naphthylacetic acid were added thionyl chloride (100 ml) and N,N-dimethylformamide (several drops), and the mixture was heated under reflux for 1 hr. The reaction mixture was concentrated under reduced pressure, and the obtained residue was dissolved in dichloromethane (1000 ml). Aluminum chloride (43 g) was added under ice-cooling, and the mixture was stirred at room temperature for 2 hr. The reaction mixture was poured into ice water, and the mixture was extracted with chloroform. The extract was washed with water and saturated brine, dried over sodium sulfate, and concentrated. The residue was isolated and purified by silica gel column chromatography to give 3-bromoacenaphthen-1-one (1.5 g) and 8-bromoacenaphthen-1-one (6.8 g).
3-bromoacenaphthen-1-one
¹H-NMR (CDCl₃)δ$_{TMS}$:3.77(s, 2H), 7.66(d, 1H), 7.70-7.75(m, 2H), 7.97(d, 1H), 8.06(d, 1H)
8-bromoacenaphthen-1-one
¹H-NMR (CDCl₃)δ$_{TMS}$:3.85(s, 2H), 7.49(d, 1H), 7.61(dd, 1H), 7.74-7.80(m, 2H), 7.89(d, 1H)
(2) 3-Bromoacenaphthen-1-one (1.5 g, 6.07 mmol) was dissolved in methanol (30 ml), sodium borohydride (280 mg) was added, and the mixture was stirred at room temperature for 1 hr. To the reaction mixture was gradually added aqueous ammonium chloride solution, and the mixture was extracted with ethyl acetate. The extract was washed with saturated brine, dried over anhydrous magnesium sulfate, and concentrated under reduced pressure to give 3-bromo-1-acenaphthenol (1.6 g). The alcohol form (1.6 g) was dissolved in chloroform (18 ml). Thionyl chloride (2 ml) was added under ice-cooling, and the mixture was heated under reflux for 1 hr. The solvent was evaporated, and the obtained residue was dissolved in N,N-dimethylformamide (13 ml). 4-(2-Keto-1-benzimidazolinyl)piperidine (1.5 g, 5.26 mmol), potassium carbonate (2.7 g) and sodium iodide (970 mg) were added, and the mixture was stirred at 140° C. for 1 hr. After allowing to cool, the reaction mixture was extracted with ethyl acetate, and the extract was washed with saturated brine, dried over anhydrous magnesium sulfate, and concentrated under reduced pressure. The residue was purified by silica gel chromatography, and recrystallized from acetone to give the title compound (1.8 g).
¹H-NMR (CDCl₃)δ$_{TMS}$:1.70-1.90(m, 2H), 2.40-2.60(m, 4H), 2.70-2.80(m, 1H), 3.00-3.10(m, 1H), 3.35-3.45(m, 2H), 4.30-4.40(m, 1H), 4.90-5.00(m, 1H), 7.00-7.15(m, 3H), 7.25-7.35(m, 1H), 7.50-7.60(m, 4H), 7.60-7.70(m, 1H), 9.85(brs, 1H)
FAB-MS (M+H)⁺:450

Example 116

2-{3-[1-(3-bromoacenaphthen-1-yl)piperidin-4-yl]-2,3-dihydro-2-oxo-benzimidazol-1-yl}-N-methylacetamide A crude product obtained in the same manner as Example 104 and using 1-[1-(3-bromoacenaphthen-1-yl)piperidin-4-yl]-1,3-dihydro-2H-benzimidazol-2-one (700 mg) was recrystallized from acetone to give the title compound (125 mg). ¹H-NMR (CDCl₃)δ$_{TMS}$:1.60-1.75(m, 2H), 2.25-2.65 (m, 7H), 2.59(s, 3H), 2.90-3.00(m, 1H), 3.30-3.40(m, 1H), 4.15-4.25(m, 1H), 4.41(s, 2H), 5.01(brs, 1H), 6.95-7.10(m, 3H), 7.31(d, 1H), 7.55-7.70(m, 3H), 7.79(d, 1H), 8.05-8.15 (m, 1H)
FAB-MS (M+H)⁺:521

Example 117

1-[1-(8-bromoacenaphthen-1-yl)piperidin-4-yl]-1,3-dihydro-2H-benzimidazol-2-one (1) 8-Bromoacenaphthen-1-one (2.4 g) was dissolved in methanol (45 ml), sodium borohydride (450 mg) was added, and the mixture was stirred at room temperature for 1 hr. To the reaction mixture was gradually added aqueous ammonium chloride solution, and the mixture was extracted with ethyl acetate. The extract was washed with saturated brine, dried over anhydrous magnesium sulfate, and concentrated under reduced pressure to give a crude product (2.2 g) of 8-bromo-1-acenaphthenol.
(2) The crude product of the alcohol form (2.2 g) was dissolved in chloroform (18 ml). Thionyl chloride (2.5 ml) was added under ice-cooling, and the mixture was heated under reflux for 1 hr. The solvent was evaporated, and the obtained residue was dissolved in N,N-dimethylformamide (18 ml). 4-(2-Keto-1-benzimidazolinyl)piperidine (2.0 g), potassium carbonate (3.7 g) and sodium iodide (1.35 g) were added, and the mixture was stirred at 140° C. for 1 hr. After allowing to cool, the reaction mixture was extracted with ethyl acetate, and the extract was washed with saturated brine, dried over anhydrous magnesium sulfate, and concentrated under reduced pressure. The residue was purified by silica gel chromatography, and recrystallized from ethyl acetate to give the title compound (1.1 g).
¹H-NMR (CDCl₃)δ$_{TMS}$:1.60-1.70(m, 1H), 1.80-1.90(m, 1H), 2.25-2.50(m, 3H), 2.50-2.70(m, 2H), 3.15-3.30(m, 2H), 3.45-3.55(m, 1H), 4.30-4.40(m, 1H), 4.90-5.00(m, 1H), 7.00-7.15(m, 3H), 7.25-7.40(m, 2H), 7.48(dd, 1H), 7.50-7.65(m, 3H), 9.48(brs, 1H)
FAB-MS (M+H)⁺:450

Example 118

2-{3-[1-(8-bromoacenaphthen-1-yl)piperidin-4-yl]-2,3-dihydro-2-oxo-benzimidazol-1-yl}-N-methylacetamide A crude product obtained in the same manner as Example 104 and using 1-[1-(8-bromoacenaphthen-1-yl)piperidin-4- yl]-1,3-dihydro-2H-benzimidazol-2-one (500 mg) was recrystallized from ethyl acetate to give the title compound (285 mg).

$^1$H-NMR (CDCl$_3$)$\delta_{TMS}$:1.60-1.70(m, 1H), 1.80-1.90(m, 1H), 2.20-2.30(m, 1H), 2.30-2.40(m, 2H), 2.50-2.75(m, 2H), 2.78(d, 3H), 3.15-3.30(m, 2H), 3.45-3.55(m, 1H), 4.30-4.40 (m, 1H), 4.49(s, 2H), 4.95-5.00(m, 1H), 6.15(brs, 1H), 7.00-7.10(m, 1H), 7.10-7.20(m, 2H), 7.30-7.40(m, 2H), 7.48(dd, 1H), 7.75-7.65(m, 3H)

FAB-MS (M+H)$^+$:521

Example 119

1-[1-(3-cyanoacenaphthen-1-yl)piperidin-4-yl]-1,3-dihydro-2H-benzimidazol-2-one

1-[1-(3-Bromoacenaphthen-1-yl)piperidin-4-yl]-1,3-dihydro-2H-benzimidazol-2-one (1.25 g) was dissolved in N,N-dimethylformamide (16 ml), zinc cyanide (380 mg) and tetrakistriphenylphosphinepalladium (1.6 g) were added, and the mixture was stirred at 110° C. for 1 hr. After allowing to cool, water and ethyl acetate were poured into the reaction mixture, and the mixture was subjected to celite filtration. The filtrate was extracted with ethyl acetate, and the extract was washed with saturated brine, and dried over magnesium sulfate. The solvent was evaporated under reduced pressure, and the residue was purified by silica gel column chromatography, and recrystallized from acetone to give the title compound (1.0 g).

$^1$H-NMR (CDCl$_3$)$\delta_{TMS}$:1.60-1.80(m, 2H), 2.40-2.65(m, 4H), 2.70-2.80(m, 1H), 3.00-3.10(m, 1H), 3.55-3.65(m, 2H), 4.25-4.40(m, 1H), 5.00-5.10(m, 1H), 7.00-7.15(m, 3H), 7.20-7.30(m, 1H), 7.35-7.50(m, 1H), 7.57(d, 1H), 7.60-7.80(m, 3H), 9.55(brs, 1H)

FAB-MS (M+H)$^+$:395

Example 120

2-{3-[1-(3-cyanoacenaphthen-1-yl)piperidin-4-yl]-2,3-dihydro-2-oxo-benzimidazol-1-yl}-N-methylacetamide A crude product obtained in the same manner as Example 104 and using 1-[1-(3-cyanoacenaphthen-1-yl)piperidin-4-yl]-1,3-dihydro-2H-benzimidazol-2-one (800 mg) was recrystallized from a mixed solvent of acetone/ethyl acetate to give the title compound (450 mg).

$^1$H-NMR (CDCl$_3$)$\delta_{TMS}$:1.70-1.90(m, 3H), 2.40-2.65(m, 3H), 2.70-2.80(m, 1H), 2.78(d, 3H), 3.00-3.20(m, 1H), 3.55-3.60(m, 2H), 4.25-4.40(m, 1H), 4.49(s, 2H), 5.03-5.06(m, 1H), 6.18(brs, 1H), 7.00-7.20(m, 3H), 7.33(d, 1H), 7.57(d, 1H), 7.65-7.80(m, 4H)

FAB-MS (M+H)$^+$:466

Example 121

1-[1-(5-cyanoacenaphthen-1-yl)piperidin-4-yl]-1,3-dihydro-2H-benzimidazol-2-one

A crude product obtained in the same manner as Example 119 and using 1-[1-(5-bromoacenaphthen-1-yl)piperidin-4-yl]-1,3-dihydro-2H-benzimidazol-2-one (2.5 g) was recrystallized from acetone to give the title compound (850 mg).

$^1$H-NMR (DMSO$_6$)$\delta_{TMS}$:1.55-1.70(m, 2H), 2.25-2.60(m, 5H), 2.90-3.00(m, 1H), 3.45-3.50(m, 2H), 4.10-4.20(m, 1H), 5.00-5.10(m, 1H), 6.90-7.00(m, 3H), 7.22(d, 1H), 7.51(d, 1H), 7.72(d, 1H), 7.80-7.90(m, 2H), 8.11(d, 1H), 10.83(brs, 1H)

FAB-MS (M+H)$^+$:395

Example 122

2-{3-[1-(5-cyanoacenaphthen-1-yl)piperidin-4-yl]-2,3-dihydro-2-oxo-benzimidazol-1-yl}-N-methylacetamide.oxalate A crude product obtained in the same manner as Example 104 and using 1-[1-(5-cyanoacenaphthen-1-yl)piperidin-4-yl]-1,3-dihydro-2H-benzimidazol-2-one (550 mg) was treated with 1.1 equivalents of oxalic acid to give the title compound (481 mg).

$^1$H-NMR (DMSO$_6$)$\delta_{TMS}$:1.70-1.85(m, 2H), 2.45-2.70(m, 2H), 2.60(s, 3H), 2.70-2.95(m, 3H), 3.20-3.30(m, 1H), 3.60-3.80(m, 2H), 4.35-4.50(m, 1H), 4.41(s, 2H), 5.30-5.40(m, 1H), 7.00-7.10(m, 3H), 7.30-7.40(m, 1H), 7.58(d, 1H), 7.85-8.00(m, 3H), 8.05-8.15(m, 1H), 8.17(d, 1H)

FAB-MS (M+H)$^+$:466

Example 123

1-[1-(8-cyanoacenaphthen-1-yl)piperidin-4-yl]-1,3-dihydro-2H-benzimidazol-2-one

A crude product obtained in the same manner as Example 119 and using 1-[1-(8-bromoacenaphthen-1-yl)piperidin-4-yl]-1,3-dihydro-2H-benzimidazol-2-one (1.0 g) was recrystallized from a mixed solvent of acetone/ethyl acetate to give the title compound (1.4 g).

$^1$H-NMR (CDCl$_3$)$\delta_{TMS}$:1.65-1.75(m, 1H), 1.85-1.95(m, 1H), 2.30-2.60(m, 3H), 2.65-2.80(m, 2H), 3.25-3.40(m, 2H), 3.50-3.60(m, 1H), 4.40-4.55(m, 1H), 5.10-5.20(m, 1H), 7.00-7.15(m, 3H), 7.40-7.50(m, 2H), 7.60-7.70(m, 3H), 7.75(d, 1H), 9.63(brs, 1H)

FAB-MS (M+H)$^+$:395

Example 124

2-{3-[1-(8-cyanoacenaphthen-1-yl)piperidin-4-yl]-2,3-dihydro-2-oxo-benzimidazol-1-yl}-N-methylacetamide A crude product obtained in the same manner as Example 104 and using 1-[1-(8-cyanoacenaphthen-1-yl)piperidin-4-yl]-1,3-dihydro-2H-benzimidazol-2-one (1.3 g) was purified twice by silica gel chromatography to give the title compound (122 mg).

$^1$H-NMR (CDCl$_3$)$\delta_{TMS}$:1.70-1.95(m, 2H), 2.30-2.60(m, 3H), 2.60-2.80(m, 2H), 2.78(d, 2H), 3.25-3.35(m, 2H), 3.50-3.60(m, 1H), 4.40-4.45(m, 1H), 4.50(s, 2H), 5.10-5.20(m, 1H), 6.20(brs, 1H), 7.04(d, 2H), 7.11(dd, 1H), 7.17(dd, 1H), 7.40-7.50(m, 1H), 7.51(d, 1H), 7.60-7.70(m, 3H), 7.68(d, 1H)

FAB-MS (M+H)$^+$:466

Example 125

1-[1-(5-methoxyacenaphthen-1-yl)piperidin-4-yl]-1,3-dihydro-2H-benzimidazol-2-one (1) 5-Bromo-1-acenaphthenol (6.4 g) and tert-butyldimethylsilyl chloride (4.6 g) were dissolved in N,N-dimethylformamide (20 ml), imidazole (4.1 g) was added while stirring the mixture at room temperature, and the mixture was stirred at 40° C. for 30 min. After completion of the reaction, the mixture was extracted with ethyl acetate, and the extract was washed with saturated brine, and dried over magnesium sulfate. The solvent was evaporated under reduced pressure, and the residue was purified by silica gel column chromatography to give 5-bromo-1-(tert-butoxydimethylsilyloxy)acenaphthene (8.3 g).

$^1$H-NMR (CDCl$_3$)δ$_{TMS}$:0.10(s, 6H), 0.86(s, 9H), 3.05(dd, 1H), 3.56(dd, 1H), 5.60-5.70(m, 1H), 6.99(d, 1H), 7.35(d, 1H), 7.45-7.60(m, 2H), 7.77(d, 1H)

(2) 5-Bromo-1-(tert-butoxydimethylsilyloxy)acenaphthene (3.0 g) was dissolved in tetrahydrofuran (40 ml), and n-butyllithium-hexane solution (1.6 mol/l, 5.5 ml) was added dropwise under a nitrogen stream while cooling the mixture to −78° C. After stirring at −78° C. for 1 hr, a solution of N,N-dimethylformamide (640 mg) in tetrahydrofuran was added dropwise, and the mixture was further stirred for 15 min. After completion of the reaction, 1N hydrochloric acid was added, and the mixture was extracted with ethyl acetate. The extract was washed with saturated brine, and dried over magnesium sulfate. The solvent was evaporated under reduced pressure to give a crude product of (RS)-5-formyl-1-(tert-butoxydimethylsilyloxy)acenaphthene.

The crude product of the formyl form was dissolved in dichloromethane (60 ml), m-chloroperbenzoic acid (65%, 3.8 g) was added under ice-cooling, and the mixture was stirred at room temperature for 15 hr. After completion of the reaction, the mixture was extracted with chloroform, and the extract was washed with saturated aqueous sodium hydrogen carbonate solution, and dried over sodium sulfate. The solvent was evaporated under reduced pressure, and the residue was purified by silica gel column chromatography to give 5-hydroxy-1-(tert-butoxydimethylsilyloxy)acenaphthene (2.1 g).

$^1$H-NMR (CDCl$_3$)δ$_{TMS}$:0.10(s, 6H), 0.86(s, 9H), 3.09(dd, 1H), 3.60(dd, 1H), 5.65-5.70(m, 1H), 7.10-7.15(m, 2H), 7.36 (d, 1H), 7.47(dd, 1H), 7.56(d, 1H), 8.36(s, 1H)

(3) To a solution of 5-hydroxy-1-(tert-butoxydimethylsilyloxy)acenaphthene (8.5 g) in N,N-dimethylformamide (70 ml) was added potassium carbonate (6.0 g), methyl iodide (5.0 g) was added dropwise thereto while stirring the mixture at room temperature, and the mixture was stirred for 9 hr. After completion of the reaction, the mixture was extracted with ethyl acetate, and the extract was washed with saturated brine, and dried over magnesium sulfate. The solvent was evaporated under reduced pressure, and the residue was purified by silica gel column chromatography to give (RS)-5-methoxy-1-(tert-butoxydimethylsilyloxy)acenaphthene (7.7 g).

$^1$H-NMR (CDCl$_3$)δ$_{TMS}$:0.10(s, 6H), 0.86(s, 9H), 3.04(dd, 1H), 3.55(dd, 1H), 3.86(s, 3H), 5.65-5.70(m, 1H), 6.66(d, 1H), 7.02(d, 1H), 7.32(d, 1H), 7.40(dd, 1H), 7.82(d, 1H)

(4) 5-Methoxy-1-(tert-butoxydimethylsilyloxy)acenaphthene (7.7 g) was dissolved in tetrahydrofuran (100 ml), a solution (120 ml) of tetrabutylammonium fluoride (1.0 mol) in tetrahydrofuran was added dropwise under ice-cooling, and the mixture was stirred at room temperature for 1 hr. After completion of the reaction, saturated aqueous ammonium chloride solution was added, and the mixture was extracted with ethyl acetate. The extract was washed with saturated brine, and dried over magnesium sulfate. The solvent was evaporated under reduced pressure, and the residue was purified by silica gel column chromatography to give 5-methoxy-1-acenaphthenol (4.0 g). A crude product obtained in the same manner as Example 103 (3) ff. and using the obtained alcohol form (4.0 g) was recrystallized from acetone to give the title compound (1.6 g).

$^1$H-NMR (CDCl$_3$)δ$_{TMS}$:1.70-1.90(m, 2H), 2.35-2.65(m, 4H), 2.75-2.85(m, 1H), 2.95-3.05(m, 1H), 3.30-3.40(m, 2H), 3.98(s, 3H), 4.25-4.40(m, 1H), 4.90-5.00(m, 1H), 6.78(d, 1H), 7.00-7.15(m, 3H), 7.15-7.20(d, 1H), 7.25-7.35(m, 1H), 7.50-7.60(m, 2H), 7.94(d, 1H), 9.97(brs, 1H)

Example

FAB-MS (M+H)$^+$:400 126

2-{3-[1-(5-methoxyacenaphthen-1-yl)piperidin-4-yl]-2,3-dihydro-2-oxo-benzimidazol-1-yl}-N-methylacetamide A crude product obtained in the same manner as Example 104 and using 1-[1-(5-methoxyacenaphthen-1-yl)piperidin-4-yl]-1,3-dihydro-2H-benzimidazol-2-one (400 mg) was recrystallized from ethyl acetate to give the title compound.

$^1$H-NMR (CDCl$_3$)δ$_{TMS}$:1.70-1.85(m, 3H), 2.35-2.60(m, 4H), 2.78(d, 3H), 3.00-3.05(m, 1H), 3.30-3.40(m, 2H), 3.99 (s, 3H), 4.25-4.40(m, 1H), 4.49(s, 2H), 4.95-5.00(m, 1H), 6.14(brs, 1H), 6.79(d, 1H), 7.00-7.20(m, 4H), 7.30-7.40(m, 1H), 7.45-7.60(m, 2H), 7.90-8.00(m, 1H)

FAB-MS (M+H)$^+$:471

Example 127

1-[1-(5-hydroxyacenaphthen-1-yl)piperidin-4-yl]-1,3-dihydro-2H-benzimidazol-2-one The title compound is obtained according to the method of Example 128 and using 1-[1-(5-methoxyacenaphthen-1-yl)piperidin-4-yl]-1,3-dihydro-2H-benzimidazol-2-one.

Example 128

2-{3-[1-(5-hydroxyacenaphthen-1-yl)piperidin-4-yl]-2,3-dihydro-2-oxo-benzimidazol-1-yl}-N-methylacetamide 2-{3-[1-(5-Methoxyacenaphthen-1-yl)piperidin-4-yl]-2,3-dihydro-2-oxo-benzimidazol-1-yl}-N-methylacetamide (780 mg) was dissolved in dichloromethane (50 ml), a solution (8.0 ml) of boron tribromide (1.0 mol) in dichloromethane was added dropwise under a nitrogen stream while cooling to −50° C., and the mixture was gradually warmed over 1 hr. After completion of the reaction, the reaction mixture was poured into an aqueous potassium carbonate solution by small portions, during which unnecessary substances were dissolved in acetone), the mixture was extracted with chloroform, and the extract was dried over sodium sulfate. The solvent was evaporated under reduced pressure, and the residue was purified by NH-coating silica gel column chromatography to give a crude product of the title compound.

$^1$H-NMR (DMSO-d$_6$)δ$_{TMS}$:1.55-1.80(m, 2H), 2.45-2.60 (m, 5H), 2.60(s, 3H), 2.90-3.00(m, 1H), 3.15-3.35(m, 3H), 4.10-4.25(m, 1H), 4.41(s, 2H), 4.90-5.00(m, 1H), 6.82(d, 1H), 7.00-7.15(m, 3H), 7.30(d, 1H), 7.40-7.50(m, 2H), 7.75-7.85(m, 1H), 8.08-8.15(m, 1H), 9.78(brs, 1H)

FAB-MS (M+H)$^+$:457

Example 129

1-[1-(3-methoxyacenaphthen-1-yl)piperidin-4-yl]-1,3-dihydro-2H-benzimidazol-2-one The title compound is obtained according to the method of Example 125 and using 3-bromo-1-acenaphthenol.

Example 130

2-{3-[1-(3-methoxyacenaphthen-1-yl)piperidin-4-yl]-2,3-dihydro-2-oxo-benzimidazol-1-yl}-N-methylacetamide The title compound is obtained according to the method of Example 104 and using 1-[1-(3-methoxyacenaphthen-1-yl)piperidin-4-yl]-1,3-dihydro-2H-benzimidazol-2-one.

Example 131

1-[1-(3-hydroxyacenaphthen-1-yl)piperidin-4-yl]-1,3-dihydro-2H-benzimidazol-2-one The title compound is obtained according to the method of Example 128 and using 1-[1-(3-methoxyacenaphthen-1-yl)piperidin-4-yl]-1,3-dihydro-2H-benzimidazol-2-one.

Example 132

2-{3-[1-(3-hydroxyacenaphthen-1-yl)piperidin-4-yl]-2,3-dihydro-2-oxo-benzimidazol-1-yl}-N-methylacetamide The title compound is obtained according to the method of Example 104 and using 1-[1-(3-hydroxyacenaphthen-1-yl)piperidin-4-yl]-1,3-dihydro-2H-benzimidazol-2-one.

Example 133

1-[1-(8-methoxyacenaphthen-1-yl)piperidin-4-yl]-1,3-dihydro-2H-benzimidazol-2-one A known compound, 8-hydroxyacenaphthen-1-one (7.0 g) (J. Chem. Soc., 1954, p. 4299), was dissolved in N,N-dimethylformamide (70 ml), potassium carbonate (7.9 g) and methyl iodide (6.8 g) were added, and the mixture was stirred at room temperature for 5 hr. After completion of the reaction, the mixture was extracted with ethyl acetate, and the extract was washed with saturated brine, and dried over magnesium sulfate. The solvent was evaporated under reduced pressure, and the residue was purified by silica gel column chromatography to give 8-methoxyacenaphthen-1-one (5.7 g). The obtained methoxy form was dissolved in methanol (25 ml), sodium borohydride (220 mg) was added, and the mixture was stirred at room temperature for 1 hr. To the reaction mixture was gradually added aqueous ammonium chloride solution, and the mixture was extracted with ethyl acetate. The extract was washed with saturated sodium chloride, dried over anhydrous magnesium sulfate, and concentrated under reduced pressure to give 8-methoxy-1-acenaphthenol (5.6 g). The title compound (2.28 g) was obtained according to the method of Example 125 and using the obtained alcohol form.

$^1$H-NMR (CDCl$_3$)$\delta_{TMS}$:1.65-1.95(m, 2H), 2.10-2.20(m, 1H), 2.30-2.50(m, 2H), 2.65-2.90(m, 3H), 3.30-3.40(m, 1H), 3.45-3.60(m, 1H), 4.07(s, 3H), 4.20-4.40(m, 1H), 5.00-5.10 (m, 1H), 7.00-7.15(m, 3H), 7.20-7.35(m, 4H), 7.56(d, 1H), 7.71(d, 1H), 9.80-10.10(brs, 1H)

FAB-MS (M+H)$^+$:400

Example 134

2-{3-[1-(8-methoxyacenaphthen-1-yl)piperidin-4-yl]-2,3-dihydro-2-oxo-benzimidazol-1-yl}-N-methylacetamide The title compound (1.4 g) was obtained according to the method of Example 104 and using 1-[1-(8-methoxyacenaphthen-1-yl)piperidin-4-yl]-1,3-dihydro-2H-benzimidazol-2-one (1.58 g).

$^1$H-NMR(CDCl$_3$)$\delta_{TMS}$:1.65-1.85(m, 2H), 2.10-2.20(m, 1H), 2.35-2.50(m, 2H), 2.78(d, 3H), 2.65-2.95(m, 3H), 3.30-3.40(m, 1H), 3.45-3.55(m, 1H), 4.07(s, 3H), 4.20-4.35(m, 1H), 4.48(s, 2H), 5.00-5.05(m, 1H), 6.14(brs, 1H), 7.00-7.15 (m, 3H), 7.20-7.40(m, 4H), 7.57(d, 1H), 7.72(d, 1H)

FAB-MS (M+H)$^+$:471

Example 135

1-[1-(8-hydroxyacenaphthen-1-yl)piperidin-4-yl]-1,3-dihydro-2H-benzimidazol-2-one The title compound is obtained according to the method of Example 128 and using 1-[1-(8-methoxyacenaphthen-1-yl)piperidin-4-yl]-1,3-dihydro-2H-benzimidazol-2-one.

Example 136

2-{3-[1-(8-hydroxyacenaphthen-1-yl)piperidin-4-yl]-2,3-dihydro-2-oxo-benzimidazol-1-yl}-N-methylacetamide The title compound is obtained according to the method of Example 104 and using 1-[1-(8-hydroxyacenaphthen-1-yl)piperidin-4-yl]-1,3-dihydro-2H-benzimidazol-2-one.

Example 137

(R)-1-[1-(6-fluoroacenaphthen-1-yl)piperidin-4-yl]-1,3-dihydro-2H-benzimidazol-2-one To a suspension of 60% sodium hydride (5.00 g) in toluene (250 ml) was added dropwise ethyl diethylphosphonoacetate (23.9 ml) under ice-cooling, and the mixture was stirred at room temperature for 1 hr. Then, a solution of 5-fluoro-3,4-dihydro-2H-naphthalen-1-one (18.0 g) in toluene (50 ml) was added dropwise, and the mixture was stirred at 80° C. for 3 hr. After cooling to room temperature, the reaction mixture was poured into ice water, and the mixture was extracted with toluene. The extract was washed with water and saturated brine, dried over magnesium sulfate, and concentrated under reduced pressure. The obtained residue was purified by silica gel column chromatography (hexane/ethyl acetate) to give ethyl (5-fluoro-3,4-dihydronaphthalen-1-yl)acetate (17.4 g).

To a solution of ethyl (5-fluoro-3,4-dihydronaphthalen-1-yl)acetate (16.4 g) in benzene (500 mL) was DDQ (2,3-dichloro-5,6-dicyanobenzoquinone)(21.5 g), and the mixture was stirred with heating for 3 hr. After cooling, the precipitated solid was dissolved in 1N sodium hydroxide, and the mixture was extracted with toluene. The extract was washed with water and saturated brine, dried over magnesium sulfate, and concentrated under reduced pressure. The obtained residue was purified by silica gel column chromatography (hexane/ethyl acetate) to give ethyl (5-fluoronaphthalen-1-yl)acetate (5.66 g).

To a solution of ethyl (5-fluoronaphthalen-1-yl)acetate (5.96 g) in ethanol (50 mL) was added 1N sodium hydroxide (50 mL), and the mixture was stirred at room temperature for 2 hr. The reaction mixture was concentrated under reduced pressure, the obtained residue was poured into water, and the mixture was washed with ethyl acetate. The aqueous layer was acidified with 1N hydrochloric acid, and extracted with chloroform, and the extract was washed with water and saturated brine, dried is over magnesium sulfate, and concentrated under reduced pressure to give (5-fluoronaphthalen-1-yl)acetic acid (4.34 g). The title compound was obtained according to the method of Example 103 and using (5-fluoronaphthalen-1-yl)acetic acid.

¹H-NMR (DMSO-d₆)$\delta_{TMS}$:1.56-1.68(m, 2H), 2.27-2.59 (m, 5H), 2.95(d, 1H), 3.39-3.45(m, 2H), 4.11-4.13(m, 1H), 4.91-4.94(m, 1H), 6.92-7.00(m, 4H), 7.22-7.48(m, 4H), 7.59 (t, 1H), 7.72(d, 1H)
FAB-MS (M+H)⁺:388

Example 138

(R)-2-{3-[1-(6-fluoroacenaphthen-1-yl)piperidin-4-yl]-2,3-dihydro-2-oxo-benzimidazol-1-yl}-N-methylacetamide The title compound was obtained according to the method of Example 104 and using (R)-1-[1-(6-fluoroacenaphthen-1-yl)piperidin-4-yl]-1,3-dihydro-2H-benzimidazol-2-one.
¹H-NMR (DMSO-d₆)$\delta_{TMS}$:1.62-1.72(m, 2H), 2.29-2.62 (m, 9H), 2.95(d, 2H), 3.30-3.40(m, 1H), 3.40-3.55(m, 2H), 4.10-4.30(m, 1H), 4.41(s, 2H), 4.92-4.95(m, 1H), 7.01-7.06 (m, 4H), 7.29-7.48(m, 4H), 7.61-7.56(m, 1H), 7.72(d, 1H), 8.07-8.08(m, 1H),
FAB-MS (M+H)⁺:458
$[\alpha]D^{20}$=+32.2°

Example 139

(R)-1-[1-(6-chloroacenaphthen-1-yl)piperidin-4-yl]-1,3-dihydro-2H-benzimidazol-2-one The title compound is obtained according to the method of Example 103 and using 6-chloro-1-acenaphthenone.

Example 140

(R)-2-{3-[1-(6-chloroacenaphthen-1-yl)piperidin-4-yl]-2,3-dihydro-2-oxo-benzimidazol-1-yl}-N-methylacetamide The title compound is obtained according to the method of Example 104 and using (R)-1-[1-(6-chloroacenaphthen-1-yl)piperidin-4-yl]-1,3-dihydro-2H-benzimidazol-2-one.

Example 141

(R)-1-[1-acenaphthen-1-yl)piperidin-4-yl]-1,3-dihydro-2H-imidazo[4,5-b]pyridin-2-one (1) (R)-1-(1-Acenaphthen-1-yl)piperidin-4-one (2.5 g) was dissolved in ethanol (20 ml), and 2,3-diaminopyridine (1.1 g) was added. The solution was ice-cooled, and tetraisopropyl orthotitanate (3.5 g) was added. The mixture was stirred at room temperature for 3 hr, the reaction mixture was ice-cooled, and sodium borohydride (0.6 g) was added. The mixture was stirred at room temperature for 3 hr, the reaction mixture was poured into ice water, and the insoluble material was removed by filtration. The filtrate was extracted with chloroform, and the extract was washed with saturated brine, dried over anhydrous sodium sulfate, and concentrated. The obtained residue was purified by silica gel column chromatography (chloroform/methanol) to give (R)-N³-[1-(1-acenaphthen-1-yl)piperidin-4-yl]-pyridine-2,3-diamine (1.4 g) as a red-yellow powder.
¹H-NMR (CDCl₃)$\delta_{TMS}$:1.45-1.56(m, 2H), 1.94-2.01(m, 2H), 2.26(m, 1H), 2.49(m, 1H), 2.66(m, 1H), 2.85(m, 1H), 3.07-3.20(m, 2H), 3.39(m, 2H), 4.26(brs, 1H), 4.91(t, J=5 Hz, 1H), 6.63(dd, J=5 Hz, 7.6 Hz, 1H), 6.74(d, J=7.6 Hz, 1H), 7.27(d, J=6.9 Hz, 1H), 7.43-7.52(m, 3H), 7.56(d, J=5 Hz, 1H), 7.61(d, J=8.2 Hz, 1H), 7.68(d, J=7.7 Hz, 1H)
(2) (R)-N³-[1-(1-Acenaphthen-1-yl)piperidin-4-yl]-pyridine-2,3-diamine (1.4 g) was dissolved in tetrahydrofuran (10 ml), 1,1'-carbonyldiimidazole (0.8 g) was added, and the mixture was stirred at room temperature for 5 hr. The reaction mixture was poured into water, and the mixture was extracted with ethyl acetate. The extract was washed with saturated aqueous ammonium chloride solution, dried over anhydrous magnesium sulfate, and concentrated. The obtained residue was purified by silica gel column chromatography (chloroform/methanol) to give the title compound (1.3 g) as a yellow solid.
¹H-NMR (CDCl₃)$\delta_{TMS}$:1.78-1.85(m, 2H), 2.26-2.46(m, 3H), 2.54-2.60(m, 1H), 2.81(m, 1H), 3.02(m, 1H), 3.43(m, 2H), 4.38(m, 1H), 4.99(t, J=5.5 Hz, 1H), 6.99(dd, J=5.3 Hz, 7.8 Hz, 1H), 7.30(d, J=6.8 Hz, 1H), 7.45-7.55(m, 4H), 7.63(d, J=8.2 Hz, 1H), 7.71(m, 1H), 8.04(d, J=5.3 Hz, 1H), 10.34(brs, 1H)
FAB-MS (M+H)⁺:371
$[\alpha]_L$=+48.44° (c1.0, chloroform)

Example 142

(R)-2-{1-[1-(acenaphthen-1-yl)piperidin-4-yl]-2,3-dihydro-2-oxo-imidazo[4,5-b]pyridin-3-yl}-N-methylacetamide (R)-1-[1-(Acenaphthen-1-yl)piperidin-4-yl]-1,3-dihydro-2H-imidazo[4,5-b]pyridin-2-one (1 g) was dissolved in DMF (30 ml). Sodium hydride (120 mg, 60%) was added, and the suspension was stirred at room temperature for 20 min. Ethyl bromoacetate (500 mg) was added, and the mixture was stirred for 2 hr. The reaction mixture was poured into ice water, and the mixture was extracted with ethyl acetate. The extract was washed with water and saturated aqueous ammonium chloride solution, dried over magnesium sulfate, and concentration to give ethyl (R)-2-{1-[1-(acenaphthen-1-yl)piperidin-4-yl]-1,2-dihydro-2-oxo-imidazo[4,5-b]pyridin-3-yl}acetate. 40% Methylamine-methanol solution (20 ml) was added, the mixture was stirred at room temperature for 2 hr, and the reaction mixture was concentrated under reduced pressure. The obtained residue was purified by silica gel column chromatography (chloroform/methanol) to give the title compound (0.86 g) as a white powder.
¹H-NMR (CDCl₃)$\delta_{TMS}$:1.78-1.86(m, 2H), 2.24-2.44(m, 3H), 2.54(m, 1H), 2.78(m, 1H), 2.80(d, J=4.7 Hz, 3H), 3.02 (m, 1H), 3.42(d, J=5.4 Hz, 2H), 4.38(m, 1H), 4.62(s, 2H), 4.98(t, J=5.4 Hz, 1H), 6.24(brs, 1H), 7.02(dd, J=5.2 Hz, 7.8 Hz, 1H), 7.30(d, J=6.9 Hz, 1H), 7.45-7.55(m, 4H), 7.63(d, J=8.2 Hz, 1H), 7.71(m, 1H), 8.03 dd, J=1.2 Hz, 5.2 Hz, 1H)
FAB-MS (M+H)⁺:442
$[\alpha]_D^{24}$=+42.16° (c1.0, chloroform)

Example 143

(R)-1-[1-(1,2,3,4-tetrahydronaphthalen-1-yl)piperidin-4-yl]-1,3-dihydro-2H-imidazo[4,5-b]pyridin-2-one The title compound was obtained as a white solid according to the method of Example 141 and using (R)-1-(1,2,3,4-tetrahydronaphthalen-1-yl)piperidin-4-one and 2,3-diaminopyridine.
¹H-NMR (CDCl₃)$\delta_{TMS}$:1.60-1.80(m, 3H), 1.85-2.10(m, 3H), 2.15-2.25(m, 2H), 2.45(m, 1H), 2.70-2.90(m, 4H), 3.05 (m, 1H), 3.92(m, 1H), 4.37(m, 1H), 7.00-7.12(m, 2H), 7.14 (dd, J=7.7, 7.8 Hz, 1H), 7.19(dd, J=7.7, 7.8 Hz, 1H), 7.51(d, J=7.8 Hz, 1H), 7.77(d, J=7.7 Hz, 1H), 8.06(d, J=5.4 Hz, 1H), 10.00(brs, 1H)
FAB-MS (M+H)⁺:349
$[\alpha]_D^{24}$=+46.0° (c0.5, chloroform)

Example 144

(R)-2-{3-[1-(1,2,3,4-tetrahydronaphthalen-1-yl)piperidin-4-yl]-2,3-dihydro-2-oxo-imidazo[4,5-b]pyridin-1-yl}-N-methylacetamide.fumarate The title compound was obtained as a white powder by preparing an acetone solution of an amorphous form obtained in the same manner as Example 142 and using (R)-1-[1-(1,2,3,4-tetrahydronaphthalen-1-yl)piperidin-4-yl]-1,3-dihydro-2H-imidazo[4,5-b]pyridin-2-one and treating the acetone solution with 1.1 equivalents of fumaric acid.

$^1$H-NMR (DMSO-d$_6$)$\delta_{TMS}$:1.60-1.75(m, 3H), 1.82(m, 1H), 1.85-2.00(m, 2H), 2.10-2.30(m, 2H), 2.35-2.55(m, 2H), 2.57(s, 3H), 2.60-2.90(m, 3H), 3.02(m, 1H), 3.90(m, 1H), 4.33(m, 1H), 4.41(s, 2H), 6.62(s, 2H), 7.02-7.25(m, 4H), 7.65-7.75(m, 2H), 7.94(d, J=5.2 Hz, 1H), 8.08(m, 1H)

FAB-MS (M+H)$^+$:420

$[\alpha]_D^{24}$=+13.65° (c0.25, methanol)

Example 145

(R)-1-[1-(acenaphthen-1-yl)piperidin-4-yl]-3-methyl-1,3-dihydro-2H-imidazo[4,5-b]pyridin-2-one (R)-1-[1-(Acenaphthen-1-yl)piperidin-4-yl]-1,3-dihydro-2H-imidazo[4,5-b]pyridin-2-one (0.78 g) was dissolved in DMF (20 ml), 60% sodium hydride (90 mg) was added, and the suspension was stirred for 20 min. Then, methyl iodide (340 mg) was added, and the mixture was stirred at room temperature for 3 hr. The reaction mixture was poured into saturated aqueous ammonium chloride solution, and the mixture was extracted with ethyl acetate. The extract was washed with water and saturated brine, dried over magnesium sulfate, and concentrated. The obtained residue was purified by silica gel column chromatography (chloroform/methanol) to give the title compound (0.58 g) as a yellow powder.

$^1$H-NMR (CDCl$_3$)$\delta_{TMS}$:1.76-1.84(m, 2H), 2.24-2.45(m, 3H), 2.53-2.59(m, 1H), 2.78(m, 1H), 3.01(m, 1H), 3.43(m, 2H), 3.49(s, 3H), 4.39(m, 1H), 4.98(t, J=5.5 Hz, 1H), 6.98(dd, J=5.3 Hz, 7.8 Hz, 1H), 7.30(d, J=6.8 Hz, 1H), 7.45-7.55(m, 4H), 7.63(d, J=8.2 Hz, 1H), 7.72(m, 1H), 8.04(d, J=5.3 Hz, 1H)

FAB-MS (M+H)$^+$:385

$[\alpha]_D^{24}$=+45.29° (c0.6, chloroform)

Example 146

(R)-1-[1-(acenaphthen-1-yl)piperidin-4-yl]-3-ethyl-1,3-dihydro-2H-imidazo[4,5-b]pyridin-2-one-2 hydrochloride A crude product obtained in the same manner as Example 145 and using ethyl bromide (250 mg) was treated with 4N hydrochloric acid-ethyl acetate solution to give the title compound (150 mg) as a yellow solid.

$^1$H-NMR (DMSO-d$_6$)$\delta_{TMS}$:1.25(t, J=7.2 Hz, 3H), 1.83(m, 1H), 1.96(m, 1H), 2.82(m, 1H), 2.94(m, 1H), 3.10(m, 1H), 3.30(m, 2H), 3.56(m, 1H), 3.68-3.75(m, 1H), 3.90(q, J=7.2 Hz, 2H), 4.79(m, 1H), 5.65(m, 1H), 7.08(m, 1H), 7.47(m, 1H), 7.59(m, 1H), 7.68(m, 1H), 7.78(m, 1H), 7.93(m, 1H), 8.01(m, 1H), 8.25-8.30(m, 2H), 12.41(brs, 1H)

FAB-MS (M+H)$^+$:399

$[\alpha]_D^{24}$=+46.76° (c0.6, methanol)

Example 147

(R)-1-[1-(acenaphthen-1-yl)piperidin-4-yl]-3-(2-methoxyethyl)-1,3-dihydro-2H-imidazo[4,5-b]pyridin-2-one The title compound (670 mg) was obtained as a yellow powder according to the method of Example 145 and using 2-bromoethylmethylether (320 mg).

$^1$H-NMR (CDCl$_3$)$\delta_{TMS}$:1.77-1.85(m, 2H), 2.26-2.44(m, 3H), 2.53-2.59(m, 1H), 2.78(m, 1H), 3.01(m, 1H), 3.35(s, 3H), 3.42(m, 2H), 3.76(t, J=5.7 Hz, 2H), 4.18(t, J=5.7 Hz, 2H), 4.39(m, 1H), 4.98(t, J=5.5 Hz, 1H), 6.97(dd, J=5.3 Hz, 7.8 Hz, 1H), 7.30(d, J=6.8 Hz, 1H), 7.45-7.55(m, 4H), 7.63(d, J=8.2 Hz, 1H), 7.71(m, 1H), 8.04(d, J=5.3 Hz, 1H)

FAB-MS (M+H)$^+$:429

$[\alpha]_D^{24}$=+40.22° (c1.0, chloroform)

Example 148

(R)-1-[1-(acenaphthen-1-yl)piperidin-4-yl]-3-cyclopropylmethyl-1,3-dihydro-2H-imidazo[4,5-b]pyridin-2-one.2 hydrochloride The title compound (270 mg) was obtained as a yellow solid by treating a crude product obtained in the same manner as Example 145 and using 1-(bromomethyl)cyclopropane (310 mg) with 4N hydrochloric acid-ethyl acetate solution.

$^1$H-NMR (DMSO-d$_6$)$\delta_{TMS}$:0.38-0.47(m, 4H), 1.24(m, 1H), 1.83(m, 1H), 1.97(m, 1H), 2.85(m, 1H), 2.95(m, 1H), 3.13(m, 1H), 3.32(m, 2H), 3.57(m, 1H), 3.69-3.75(m, 3H), 3.96(m, 1H), 4.78(m, 1H), 5.66(m, 1H), 7.08(m, 1H), 7.47(m, 1H), 7.59(m, 1H), 7.68(m, 1H), 7.78(m, 1H), 7.93(m, 1H), 8.01(m, 1H), 8.25-8.30(m, 2H), 12.42(brs, 1H)

FAB-MS (M+H)$^+$:425

$[\alpha]_D^{24}$=+38.58° (c0.7, methanol)

The structural formulas of the Example compounds of the present invention are shown in the following Tables.

TABLE 1

| Example No. | Structural formula |
| --- | --- |
| 1 | |
| 2 | |
| 3 | |

TABLE 1-continued

| Example No. | Structural formula |
|---|---|
| 4 | (tetrahydronaphthalene)-N-piperidine-N-benzimidazolone-CH2-C(O)-NH-CH3 |

TABLE 2

| Example No. | Structural formula |
|---|---|
| 5 | (tetrahydronaphthalene)-N-piperidine-N-benzimidazolone (NH) |
| 6 | (tetrahydronaphthalene)-N-piperidine-N-benzimidazolone-CH2-C(O)-NH-CH3 |
| 7 | (5-methyl-tetrahydronaphthalene)-N-piperidine-N-benzimidazolone (NH) |
| 8 | (5-methyl-tetrahydronaphthalene)-N-piperidine-N-benzimidazolone-CH2-C(O)-NH-CH3 |

TABLE 3

| Example No. | Structural formula |
|---|---|
| 9 | (5-methyl-tetrahydronaphthalene)-N-piperidine-N-benzimidazolone (NH) |
| 10 | (5-methyl-tetrahydronaphthalene)-N-piperidine-N-benzimidazolone-CH2-C(O)-NH-CH3 |
| 11 | (5-chloro-tetrahydronaphthalene)-N-piperidine-N-benzimidazolone (NH) |
| 12 | (5-chloro-tetrahydronaphthalene)-N-piperidine-N-benzimidazolone-CH2-C(O)-NH-CH3 |

TABLE 4

| Example No. | Structural formula |
|---|---|
| 13 | (5,7-dimethyl-tetrahydronaphthalene)-N-piperidine-N-benzimidazolone (NH) |
| 14 | (5,7-dimethyl-tetrahydronaphthalene)-N-piperidine-N-benzimidazolone-CH2-C(O)-NH-CH3 |

TABLE 4-continued

| Example No. | Structural formula |
|---|---|
| 15 | |
| 16 | |

TABLE 5

| Example No. | Structural formula |
|---|---|
| 17 | hydrochloride |
| 18 | hydrochloride |
| 19 | |
| 20 | hydrochloride |

TABLE 6
| Example No. | Structural formula |
|---|---|
| 21 | 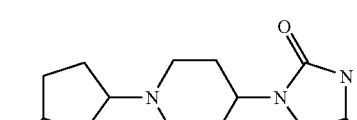 |
| 22 | 
hydrochloride |
TABLE 6-continued
| Example No. | Structural formula |
|---|---|
| 23 |  |
| 24 | 
hydrochloride |
TABLE 7
| Example No. | Structural formula |
|---|---|
| 25 | |
| 26 | |
| 27 | |
| 28 | |

TABLE 8
| Example No. | Structural formula |
|---|---|
| 29 | 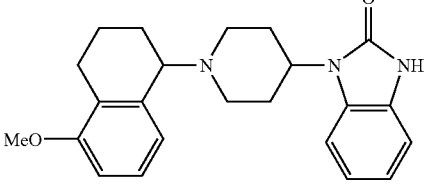 |
| 30 | 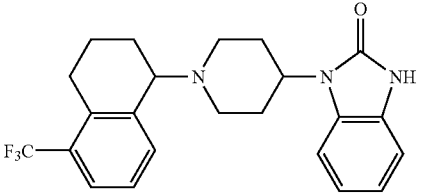 [SMILES: O=c1[nH]c2ccccc2n1C1CCN(C2CCCc3c2cccc3C(F)(F)F)CC1] |
| 31 | 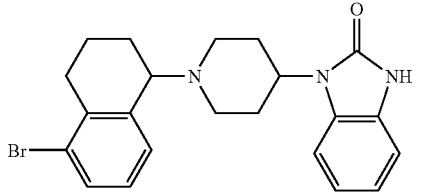 [SMILES: O=c1[nH]c2ccccc2n1C1CCN(C2CCCc3c(Br)cccc32)CC1] |
| 32 | 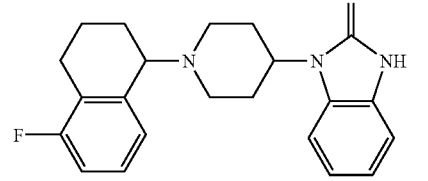 |
TABLE 9
| Example No. | Structural formula |
|---|---|
| 33 | 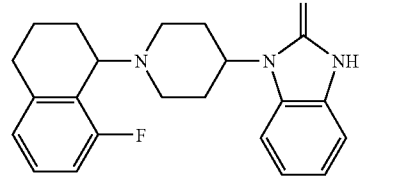 |
| 34 | 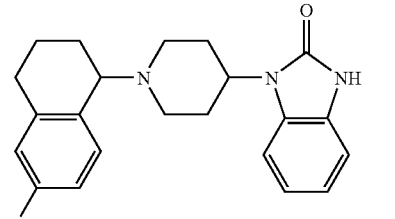 |
TABLE 9-continued
| Example No. | Structural formula |
|---|---|
| 35 | 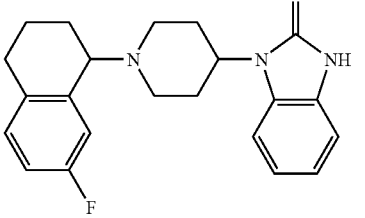 |
| 36 | 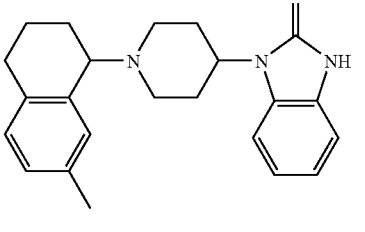 |
TABLE 10
| Example No. | Structural formula |
|---|---|
| 37 | 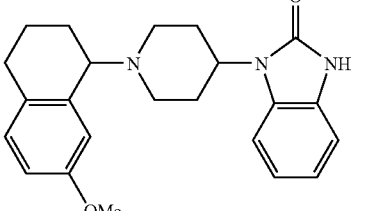 |
| 38 | 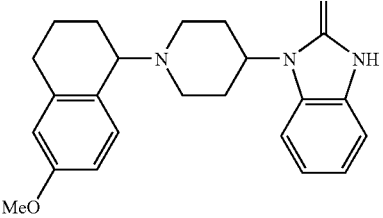 |
| 39 | 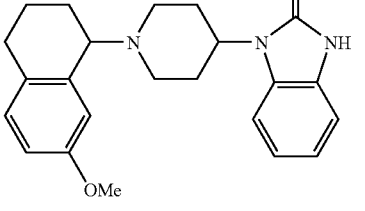 |
| 40 | 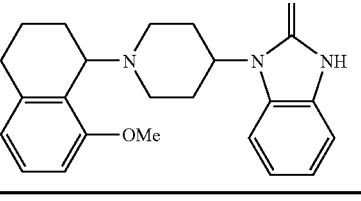 |

TABLE 11

| Example No. | Structural formula |
|---|---|
| 41 | (chroman-4-yl)-piperidin-1-yl-benzimidazol-2(3H)-one |
| 42 | (thiochroman-4-yl)-piperidin-1-yl-benzimidazol-2(3H)-one |
| 43 | (1,1-dioxo-thiochroman-4-yl)-piperidin-1-yl-benzimidazol-2(3H)-one |

TABLE 11-continued

| Example No. | Structural formula |
|---|---|
| 44 | (5-cyano-1,2,3,4-tetrahydronaphthalen-1-yl)-piperidin-1-yl-benzimidazol-2(3H)-one |
| 45 | (5-acetamido-1,2,3,4-tetrahydronaphthalen-1-yl)-piperidin-1-yl-benzimidazol-2(3H)-one |

TABLE 12

| Example No. | Structural formula |
|---|---|
| 46 | (5-methoxy-1,2,3,4-tetrahydronaphthalen-1-yl)-piperidin-1-yl-[3-(N-methylcarbamoylmethyl)-benzimidazol-2(3H)-one] |
| 47 | (5-trifluoromethyl-1,2,3,4-tetrahydronaphthalen-1-yl)-piperidin-1-yl-[3-(N-methylcarbamoylmethyl)-benzimidazol-2(3H)-one] |
| 48 | (5-bromo-1,2,3,4-tetrahydronaphthalen-1-yl)-piperidin-1-yl-[3-(N-methylcarbamoylmethyl)-benzimidazol-2(3H)-one] |
| 49 | (5-fluoro-1,2,3,4-tetrahydronaphthalen-1-yl)-piperidin-1-yl-[3-(N-methylcarbamoylmethyl)-benzimidazol-2(3H)-one] |

TABLE 13
| Example No. | Structural formula |
|---|---|
| 50 | 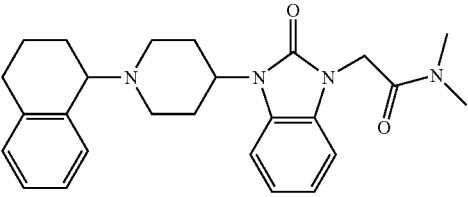 [SMILES: CN(C)C(=O)Cn1c(=O)n(C2CCN(C3CCCc4ccccc43)CC2)c2ccccc21] |
| 51 | 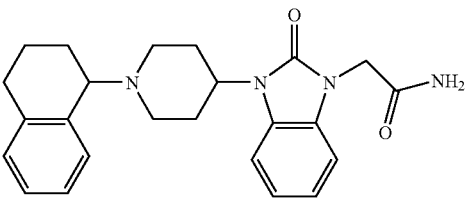 [SMILES: NC(=O)Cn1c(=O)n(C2CCN(C3CCCc4ccccc43)CC2)c2ccccc21] |
| 52 | 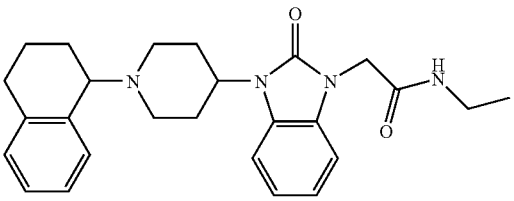 [SMILES: CCNC(=O)Cn1c(=O)n(C2CCN(C3CCCc4ccccc43)CC2)c2ccccc21] |
| 53 | 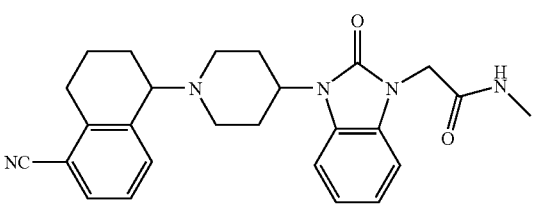 |
TABLE 14
| Example No. | Structural formula |
|---|---|
| 54 | 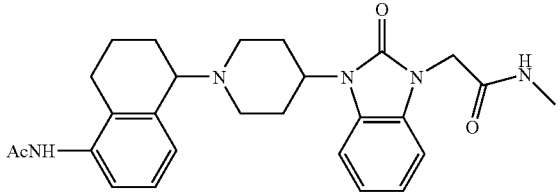 |
| 55 | 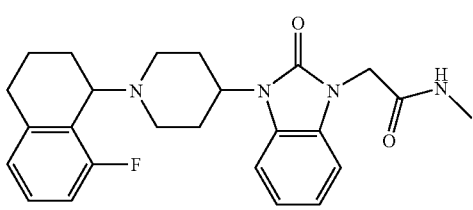 [SMILES: CNC(=O)Cn1c(=O)n(C2CCN(C3CCCc4cccc(F)c43)CC2)c2ccccc21] |

TABLE 14-continued

| Example No. | Structural formula |
|---|---|
| 56 | (6-fluoro-tetrahydronaphthalen-1-yl)-piperidinyl-benzimidazolone-CH2-C(=O)NHMe |
| 57 | (7-fluoro-tetrahydronaphthalen-1-yl)-piperidinyl-benzimidazolone-CH2-C(=O)NHMe |
| 58 | (6-methyl-tetrahydronaphthalen-1-yl)-piperidinyl-benzimidazolone-CH2-C(=O)NHMe |

TABLE 15

| Example No. | Structural formula |
|---|---|
| 59 | (7-methyl-tetrahydronaphthalen-1-yl)-piperidinyl-benzimidazolone-CH2-C(=O)NHMe |
| 60 | (6-MeO-tetrahydronaphthalen-1-yl)-piperidinyl-benzimidazolone-CH2-C(=O)NHMe |
| 61 | (7-OMe-tetrahydronaphthalen-1-yl)-piperidinyl-benzimidazolone-CH2-C(=O)NHMe |
| 62 | (8-OMe-tetrahydronaphthalen-1-yl)-piperidinyl-benzimidazolone-CH2-C(=O)NHMe |

TABLE 16
| Example No. | Structural formula |
|---|---|
| 63 | 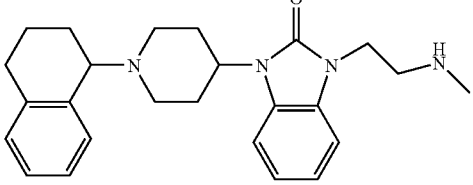 |
| 64 | 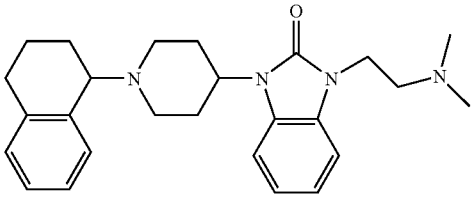 [SMILES: CN(C)CCn1c(=O)n(C2CCN(C3CCCc4ccccc43)CC2)c2ccccc21] |
TABLE 16-continued
| Example No. | Structural formula |
|---|---|
| 65 | 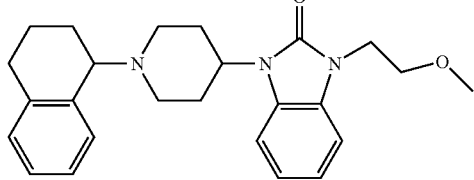 |
| 66 | 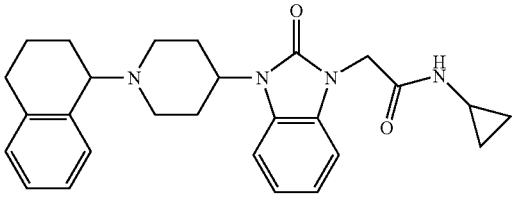 [SMILES: O=C(Cn1c(=O)n(C2CCN(C3CCCc4ccccc43)CC2)c2ccccc21)NC1CC1] |
TABLE 17
| Example No. | Structural formula |
|---|---|
| 67 | 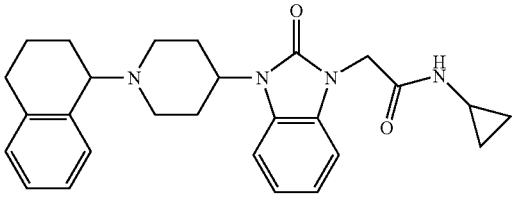 [SMILES: O=C(Cn1c(=O)n(C2CCN(C3CCCc4ccccc43)CC2)c2ccccc21)NC1CC1] |
| 68 | 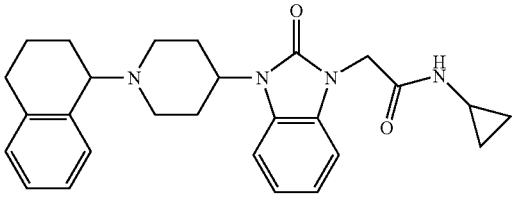 [SMILES: O=C(Cn1c(=O)n(C2CCN(C3CCCc4ccccc43)CC2)c2ccccc21)NC1CC1] |
| 69 | 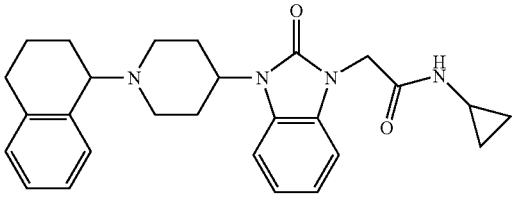 [SMILES: O=C(Cn1c(=O)n(C2CCN(C3CCCc4ccccc43)CC2)c2ccccc21)NC1CC1] |
| 70 | 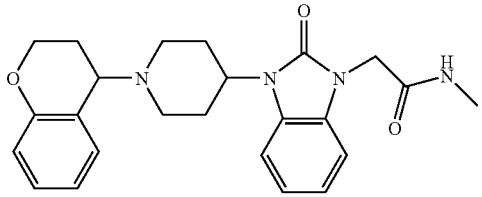 [SMILES: CNC(=O)Cn1c(=O)n(C2CCN(C3CCSc4ccccc43)CC2)c2ccccc21] |

TABLE 18
| Example No. | Structural formula |
|---|---|
| 71 | 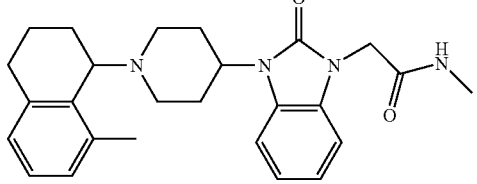 |
| 72 | 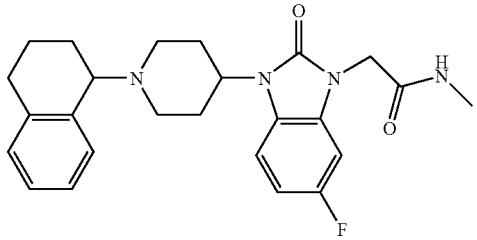 [SMILES: CNC(=O)Cn1c(=O)n(C2CCN(C3CCCc4ccccc43)CC2)c2ccc(F)cc21] |
TABLE 18-continued
| Example No. | Structural formula |
|---|---|
| 73 | 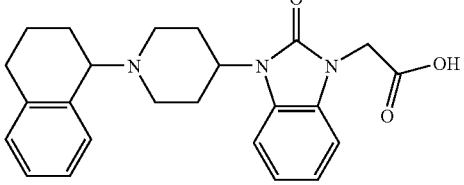 |
| 74 | 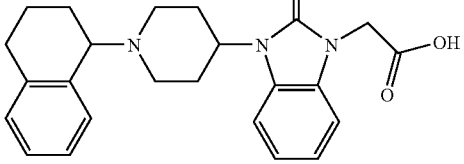 |
TABLE 19
| Example No. | Structural formula |
|---|---|
| 75 | 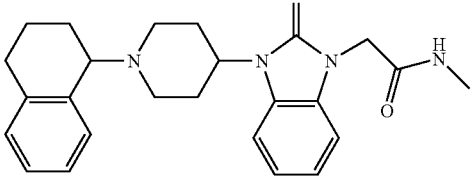 |
| 76 | 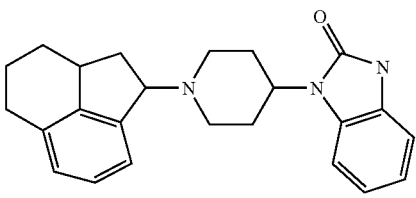 [SMILES: O=c1[nH]c2ccccc2n1C1CCN(C2CC3CCCc4cccc2c43)CC1] |
| 77 | 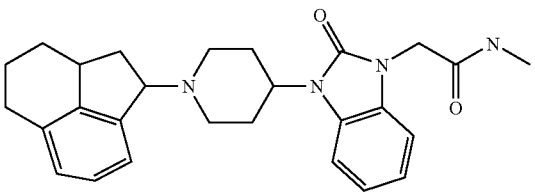 [SMILES: CNC(=O)Cn1c(=O)n(C2CCN(C3CC4CCCc5cccc3c54)CC2)c2ccccc21]<br>stereoisomer of Example 75 |
| 78 | 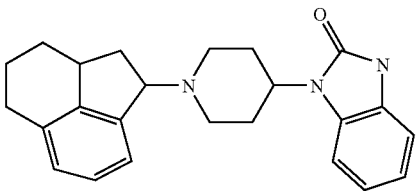<br>stereoisomer of Example 76 |

TABLE 20
| Example No. | Structural formula |
|---|---|
| 79 | 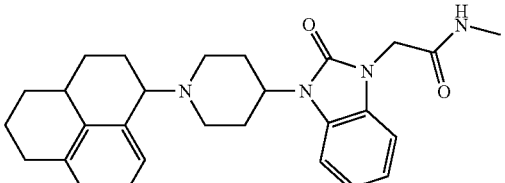 (1RS, 3aSR form) |
| 80 | 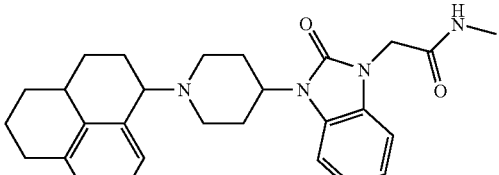 (1RS, 3aRS form) |
TABLE 20-continued
| Example No. | Structural formula |
|---|---|
| 81 | 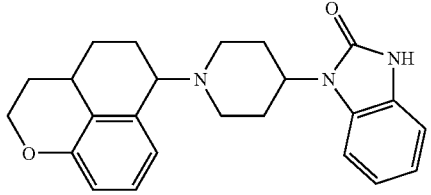 [SMILES: O=c1[nH]c2ccccc2n1C1CCN(C2CCC3CCOc4cccc2c43)CC1] |
| 82 | 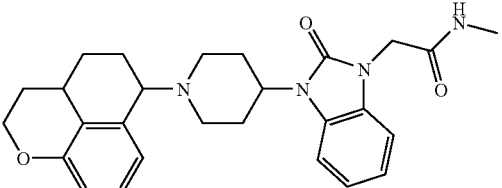 |
TABLE 21
| Example No. | Structural formula |
|---|---|
| 83 | 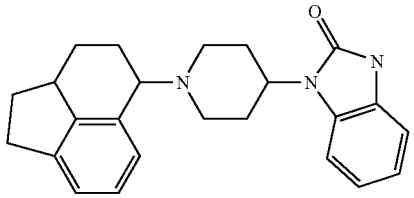 [SMILES: O=c1[nH]c2ccccc2n1C1CCN(C2CCC3CCc4cccc2c43)CC1] |
| 84 | 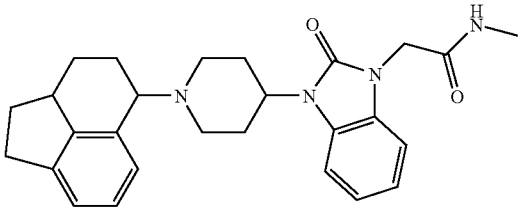 [SMILES: CNC(=O)Cn1c(=O)n(C2CCN(C3CCC4CCc5cccc3c54)CC2)c2ccccc21] |
| 85 | 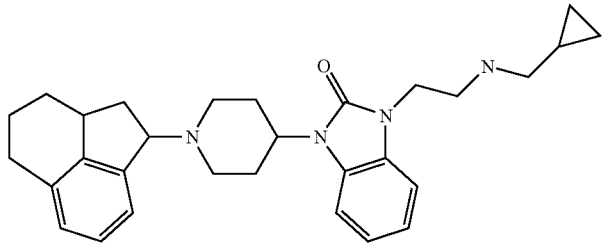 [SMILES: O=c1n(CCNCC2CC2)c2ccccc2n1C1CCN(C2CC3CCCc4cccc2c43)CC1] |
| 86 | 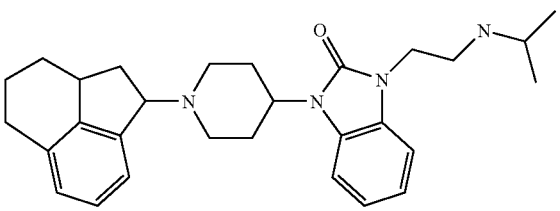 [SMILES: CC(C)NCCn1c(=O)n(C2CCN(C3CC4CCCc5cccc3c54)CC2)c2ccccc21] |

TABLE 22

| Example No. | Structural formula |
|---|---|
| 87 | |
| 88 | |
| 89 | |
| 90 | |
| 91 | |

TABLE 23
| Example No. | Structural formula |
|---|---|
| 92 | 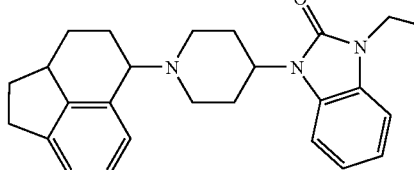 |
| 93 |  |
| 94 | 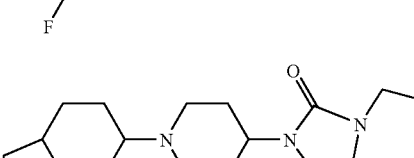 |
TABLE 23-continued
| Example No. | Structural formula |
|---|---|
| 95 | 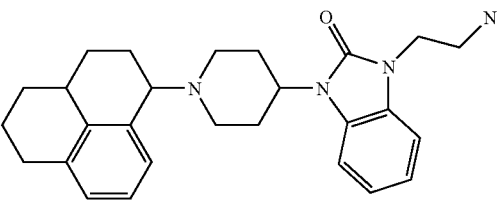 |
| 96 | 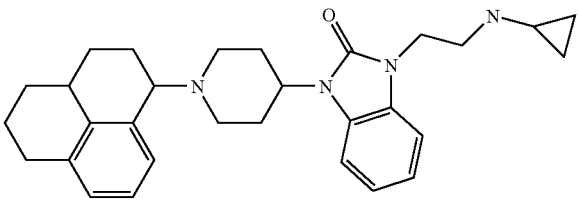 [SMILES: O=c1n(CCNC2CC2)c2ccccc2n1C1CCN(C2CCC3CCCc4cccc2c43)CC1] |
TABLE 24
| Example No. | Structural formula |
|---|---|
| 97 | 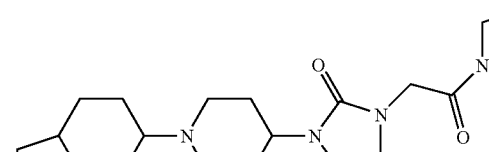 |
| 98 | |
| 99 | |

TABLE 24-continued

| Example No. | Structural formula |
|---|---|
| 100 | |

TABLE 25

| Example No. | Structural formula |
|---|---|
| 101 | |
| 102 | |
| 103 | |
| 104 | (maleate) |
| 105 | |

TABLE 26
| Example No. | Structural formula |
|---|---|
| 106 | 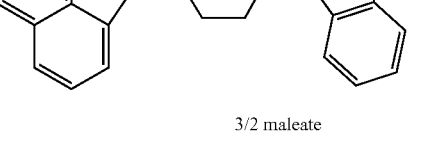<br>3/2 maleate |
| 107 | 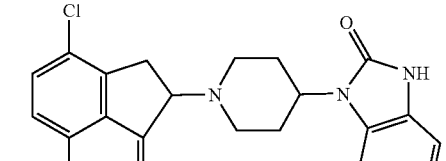 |
| 108 | <br>1/2 maleate |
| 109 | 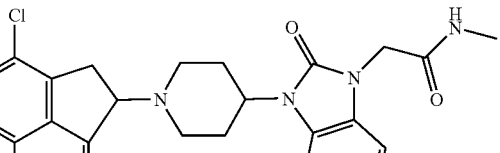 |
| 110 | 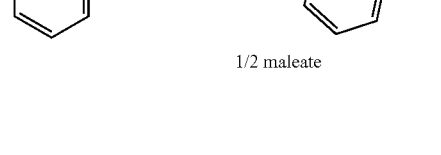 |

TABLE 27
| Example No. | Structural formula |
|---|---|
| 111 | 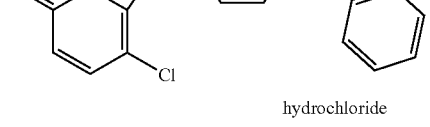 hydrochloride |
| 112 | 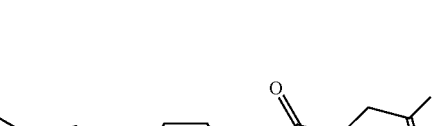 oxalate |
| 113 | 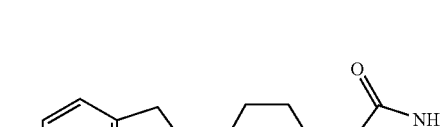 |
| 114 |  |
| 115 | 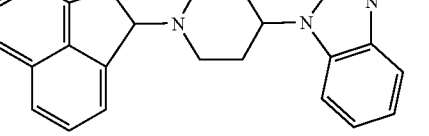 |

TABLE 28
| Example No. | Structural formula |
|---|---|
| 116 | 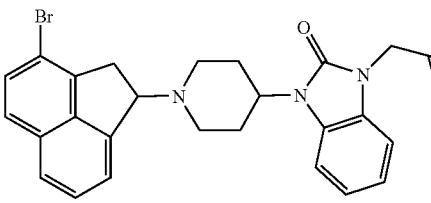 |
| 117 | 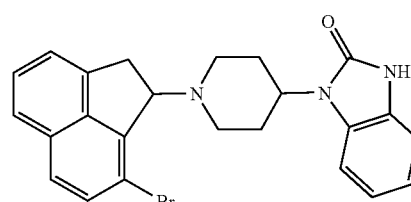 |
| 118 | 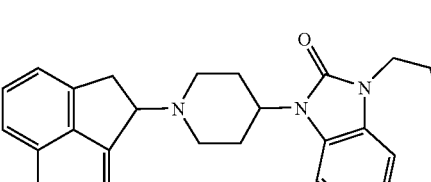 |
TABLE 28-continued
| Example No. | Structural formula |
|---|---|
| 119 | 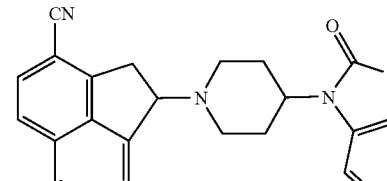 |
| 120 |  |
TABLE 29
| Example No. | Structural formula |
|---|---|
| 121 | 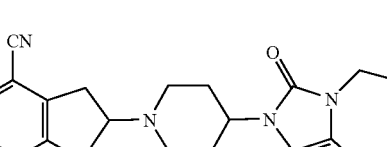 |
| 122 |  oxalate |
| 123 |  |

TABLE 29-continued

| Example No. | Structural formula |
|---|---|
| 124 | (structure: acenaphthylene-CN substituted, piperidine, benzimidazolone with CH2C(O)NHMe) |
| 125 | (structure: MeO-acenaphthylene, piperidine, benzimidazol-2(3H)-one) |

TABLE 30

| Example No. | Structural formula |
|---|---|
| 126 | (structure: MeO-acenaphthylene, piperidine, benzimidazolone with CH2C(O)NHMe) |
| 127 | (structure: HO-acenaphthylene, piperidine, benzimidazol-2(3H)-one) |
| 128 | (structure: HO-acenaphthylene, piperidine, benzimidazolone with CH2C(O)NHMe) |
| 129 | (structure: OMe-acenaphthylene, piperidine, benzimidazol-2(3H)-one) |

TABLE 30-continued
| Example No. | Structural formula |
|---|---|
| 130 |  |
TABLE 31
| Example No. | Structural formula |
|---|---|
| 131 | 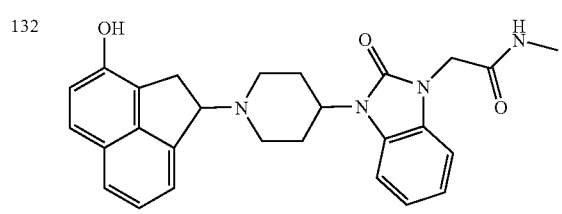 |
| 132 | 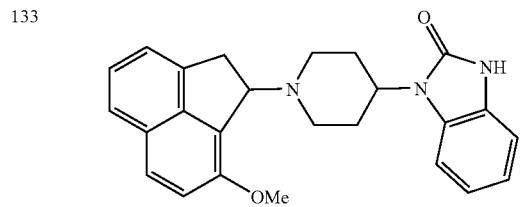 |
| 133 | 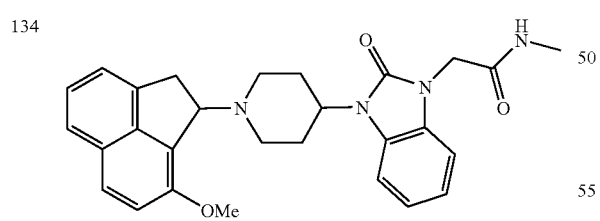 |
| 134 | 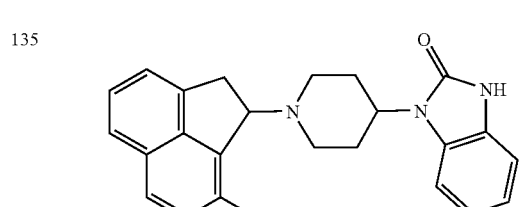 |
| 135 | |
TABLE 32
| Example No. | Structural formula |
|---|---|
| 136 | 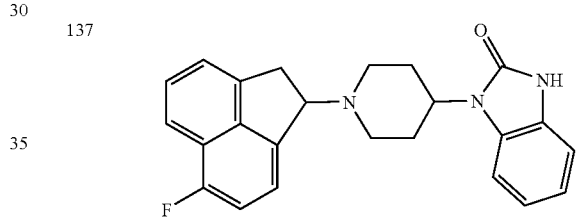 |
| 137 | 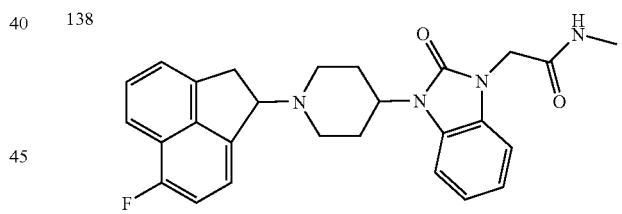 |
| 138 | 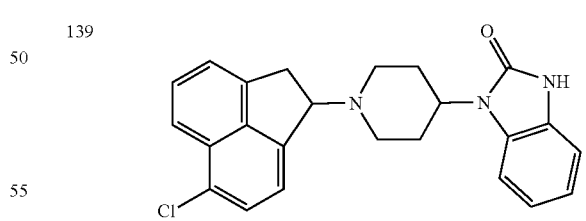 |
| 139 | 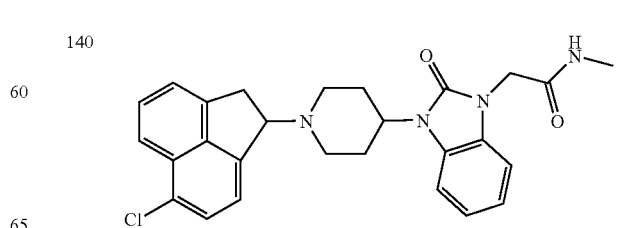 |
| 140 | |

TABLE 33

| Example No. | Structural formula |
|---|---|
| 141 | (acenaphthyl-piperidine-imidazo[4,5-b]pyridin-2(3H)-one, NH) |
| 142 | (acenaphthyl-piperidine-imidazo[4,5-b]pyridin-2-one-CH2-C(O)NHMe) |
| 143 | (tetrahydronaphthyl-piperidine-imidazo[4,5-b]pyridin-2(3H)-one, NH) |
| 144 | (tetrahydronaphthyl-piperidine-imidazo[4,5-b]pyridin-2-one-CH2-C(O)NHMe), fumarate |

TABLE 34

| Example No. | Structural formula |
|---|---|
| 145 | (acenaphthyl-piperidine-imidazo[4,5-b]pyridin-2-one-N-Me) |
| 146 | (acenaphthyl-piperidine-imidazo[4,5-b]pyridin-2-one-N-Et), dihydrochloride |

TABLE 34-continued

| Example No. | Structural formula |
|---|---|
| 147 | (acenaphthyl-piperidine-imidazo[4,5-b]pyridin-2-one-N-CH2CH2OMe) |
| 148 | (acenaphthyl-piperidine-imidazo[4,5-b]pyridin-2-one-N-CH2-cyclopropyl), dihydrochloride |

The pharmacological action of the compound of the present invention is explained in the following by way of Experimental Examples.

The comparison control compounds used were as shown below.

Compound A (WO2005/028466, cis or trans stereoisomer of compound 1)

Compound B (WO2005/028466, the other stereoisomer of compound A)

Experimental Example 1

ORL-1 Receptor-Binding Test (Experimental Method and Measurement)

Using a receptor membrane product prepared from HEK293 cell forcively expressing human ORL-1 receptor, a [$^3$H]-nociceptin binding test was performed. To be specific, a test substance solution (50 μL) having various concentrations, a receptor product solution (900 μL) and a labeled ligand [$^3$H]-nociceptin (50 μL) were successively added to a polypropylene tube and reacted at 25° C. for 60 min. The reaction mixture was filtered by suction in a cell harvester using a glass filter Whatman GF/B. The filter was washed 3 times with ice-cooled 50 mmol/L HEPES buffer, and placed in a measurement vial. A liquid scintillation cocktail ACS-II (Amersham) (2 mL) was added, and the radiation dose was measured by a liquid scintillation counter (LSC-5100, Aloka). The non-specific binding level was determined using an unlabeled ligand naltrexone. The binding inhibitory rate (%) and inhibitory constant (Ki value) were calculated according to the following calculation formula.

binding inhibitory rate (%)={1−(B−N)/(T−N)}×100

N: non-specific binding level, T: total binding level, B: binding level in the presence of a test substance inhibitory constant (Ki value)=$IC_{50}/(1+L/Kd)$ $IC_{50}$: 50% inhibitory concentration, L: labeled ligand concentration, Kd: dissociation constant of labeled ligand Experimental Example 2

μ Receptor-Binding Test (Test Method and Measurement)

Using a receptor membrane product prepared from CHO cell forcively expressing human p receptor, a [$^3$H]-DAMGO binding test was performed. To be specific, a test substance solution (50 μL) having various concentrations, a receptor product solution (900 μL) and a labeled ligand [$^3$H]-DAMGO (50 μL) were successively added to a polypropylene tube and reacted at 25° C. for 60 min. The reaction mixture was filtered by suction in a cell harvester using a glass filter Whatman GF/B. The filter was washed 3 times with ice-cooled 50 mmol/L Tris/HCl buffer, and placed in a measurement vial. A liquid scintillation cocktail ACS-II (Amersham) (2 mL) was added, and the radiation dose was measured by a liquid scintillation counter (LSC-5100, Aloka). The non-specific binding level was determined using an unlabeled ligand test compound A. The binding inhibitory rate (%) and inhibitory constant (Ki value) were calculated according to the following calculation formula.

$$\text{binding inhibitory rate (\%)} = \{1-(B-N)/(T-N)\} \times 100$$

N: non-specific binding level, T: total binding level, B: binding level in the presence of a test substance inhibitory constant (Ki value)=$IC_{50}/(1+L/Kd)$ $IC_{50}$: 50% inhibitory concentration, L: labeled ligand concentration, Kd: dissociation constant of labeled ligand (Results and Discussion)

The results are shown in the following Table. The affinity (Ki value) in the above-mentioned experiments is shown with "+++" for not more than 10 nM, "++" for 10 nM-30 nM, "+" for 30 nM-100 nM, "−" for not less than 100 nM for inhibition, and ND shows no data is available.

TABLE 35

| Test compound | Affinity Ki (nM) | |
| --- | --- | --- |
| | ORL-1 | μ |
| compound A | +++ | ++ |
| compound B | +++ | ++ |
| Example 2 | +++ | ND |
| Example 4 | +++ | ND |
| Example 8 | +++ | ND |
| Example 16 | +++ | ND |
| Example 79 | +++ | + |
| Example 80 | +++ | − |
| Example 103 | +++ | ND |
| Example 104 | +++ | ND |
| Example 108 | +++ | ND |
| Example 110 | +++ | ND |

As shown in the above-mentioned Table, the compounds of Examples 2, 4, 8, 16, 79, 80, 103, 104, 108 and 110 showed high affinity for ORL-1 receptor as evidenced by Ki value of 10 nM or lower.

Moreover, it was found that the compounds of Examples 79 and 80 have weak affinity for p receptor, and selectively act on ORL-1 receptor.

Experimental Example 3

Agonistic Action (Experimental Method and Measurement)

Using a receptor membrane product prepared from HEK293 cell forcively expressing human ORL-1 receptor, a GTPγ$^{35}$S-binding test was performed. To be specific, a reaction buffer or a test substance solution (50 μL) having various concentrations, a reaction buffer (for total binding) or a GTPγS solution (for non-specific binding, final concentration: 10 μmol/L) (50 μL), a membrane solution (850 μL) and a GTPγ$^{35}$S (Amersham Pharmacia Biotech) solution (final concentration: 100 μmol/L)(50 μL) were successively added to a polypropylene tube, and reacted at 30° C. for 60 min. The reaction mixture was filtered by suction in a cell harvester using a glass filter Whatman GF/B. The filter was washed 3 times with ice-cooled 50 mmol Tris/HCl buffer (pH 7.4), and placed in a measurement vial. A liquid scintillation cocktail ACS-II (Amersham) (2 mL) was added, and the radiation dose was measured by a liquid scintillation counter (LSC-5100, Aloka). Expressing the non-specific binding level with the addition of GTPγS as N, the binding level with the addition of a reaction buffer instead of a test substance as A and the binding level in the presence of a test substance as B, the agonistic activity, namely, GTPγ$^{35}$S bound (%) is shown by the following calculation formula.

$$\text{GTP}\gamma^{35}\text{S bound (\%)} = \{(B-N)/(A-N)\} \times 100$$

(Results and Discussion)

Figure 2:
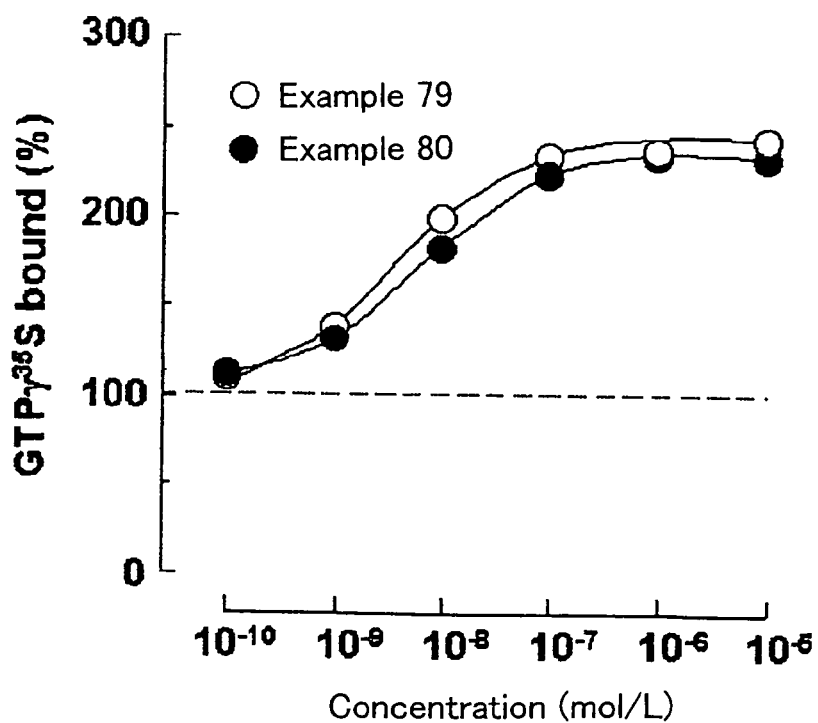
FIG. 2 shows the ORL-1 receptor agonistic activity of the compounds of Examples 79 and 80.
Figure 3:
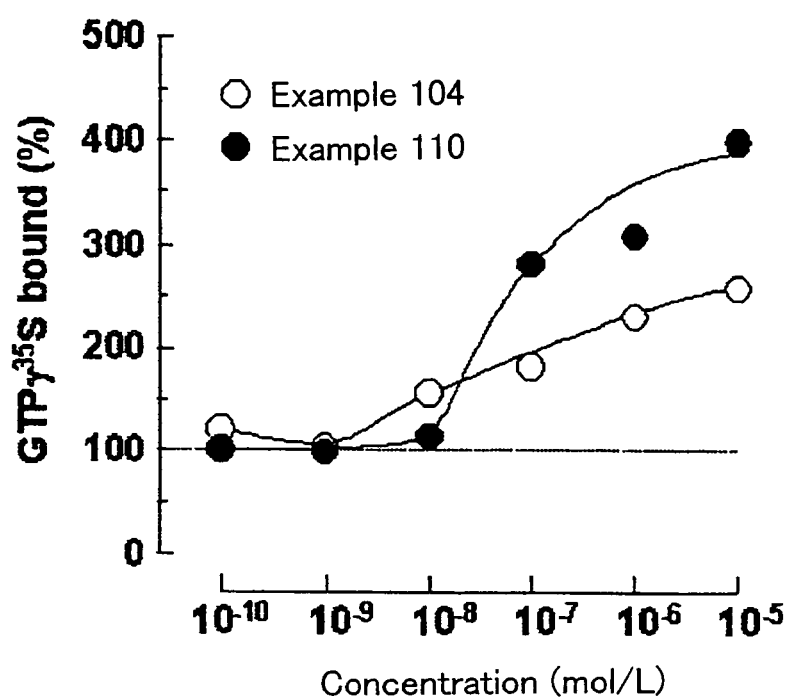
FIG. 3 shows the ORL-1 receptor agonistic activity of the compounds of Examples 104 and 110.

As shown in FIGS. 1-3, the compounds of Examples 2, 4, 8, 79, 80, 104 and 110 increased the proportion of GTPγ$^{35}$S bound in a concentration-dependent manner. Thus, it has been clarified that the compounds of Examples 2, 4, 8, 79, 80, 104 and 110 act as agonists for ORL-1 receptor.

Experimental Example 4

Food Consumption Increasing Action in Rat (Experimental Method and Measurement)

It has been reported that administration of nociceptin, which is an endogenous agonist of ORL-1 receptor, into the brain ventricle of rat temporarily increases food consumption (NeuroReport 8: 369-371, 1996). Therefore, it is possible to measure in vivo ORL-1 receptor agonistic activity with an increase in the food consumption in rat as an index. When rat is housed in a 12 hr light-dark cycle, the rat ingests most food in the dark period. Therefore, the experiment was performed in the light period when rat generally rarely ingests food. To be specific, a test substance was orally administered at 3-4 hr after the start of the light period, and the food weight was measured at 1, 2, 4 and 6 hr after administration. The difference between the food weight immediately before administration and that after administration was taken as a food consumption amount, which was converted to the amount per 1 kg of the body weight of the rat.

(Results and Discussion)

The compounds of Examples 2, 4, 8, 79 and 80 significantly increase food consumption in rats. Thus, it has been clarified that these compounds act as ORL-1 receptor agonists in vivo.

Formulation Example 1

Tablet

| compound of the present invention | 10 mg |
| crystalline cellulose | 180 mg |
| cornstarch | 300 mg |
| lactose | 600 mg |
| magnesium stearate | 15 mg |

The above-mentioned components are mixed according to a conventional method, and tableted by a conventional apparatus.

Formulation Example 2

Tablet

| compound of the present invention | 10.0 mg |
| lactose | 50.0 mg |
| cornstarch | 20.0 mg |
| crystalline cellulose | 29.7 mg |
| polyvinylpyrrolidone K30 | 5.0 mg |
| talc | 5.0 mg |
| magnesium stearate | 0.3 mg |
|  | 120.0 mg |

The compound of the present invention, lactose, cornstarch and crystalline cellulose were mixed and kneaded using polyvinylpyrrolidone K30 paste, and the mixture was passed through a 20 mesh sieve to give granules. After drying at 50° C. for 2 hr, the granules were passed through a 24 mesh sieve, mixed with talc and magnesium stearate, and tablet weighing 120 mg per tablet was produced using a pestle with diameter 7 mm.

INDUSTRIAL APPLICABILITY

Compound (I) of the present invention has superior metabolic stability and strong ORL-1 receptor agonistic action, and can be used for the prophylaxis and/or treatment of diseases relating to ORL-1 receptors, such as central nervous system diseases (e.g., anxiety and stress disorder, melancholia, traumatic injury, Alzheimer's disease, dementia, sleep disorder, drug addiction, alcoholism), acute and/or chronic pain symptom, arterial blood pressure disorder and eating disorders such as obesity and anorexia.

This application is based on patent application Nos. 2007-051842, 2007-059260, 2007-078845 and 2007-093846 filed in Japan, the contents of which are incorporated in full herein by this reference. In addition, the patent documents and non-patent documents cited in the present specification are hereby incorporated in their entireties by reference, to the extent that they have been disclosed in the present specification.

The invention claimed is:

1. A compound represented by the formula (I)

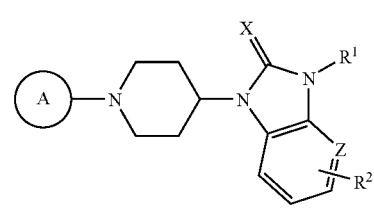

wherein

is the following formula (a)

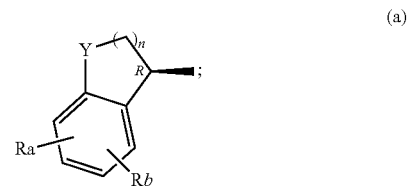

n is an integer of 2;
$R^1$ is —$CH_2$—C(O)—$NR^3R^4$;
one of $R^3$ and $R^4$ is hydrogen, and the other is lower alkyl;
$R^2$ is hydrogen;
Ra and Rb are the same or different and each is hydrogen or lower alkyl;
X is O;
Y is $CH_2$; and
Z is CH,
or a pharmaceutically acceptable salt thereof.

2. The compound of claim 1, which is (R)-2-{3[1-(1,2,3,4-tetrahydronaphthalen-1-yl)piperidin-4-yl]-2,3-dihydro-2-oxo-benzimidazol-1-yl}-N-methylacetamide, or a pharmaceutically acceptable salt thereof.

3. The compound of claim 1, which is (R)-2-{3-[(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof.

4. A method for the treatment of alcoholism, comprising administering the compound of claim 1 or a pharmaceutically acceptable salt thereof to a patient in need thereof.

5. A method for the treatment of alcoholism, comprising administering the compound of claim 2 or a pharmaceutically acceptable salt thereof to a patient in need thereof.

6. A method for the treatment of alcoholism, comprising administering the compound of claim 3 or a pharmaceutically acceptable salt thereof to a patient in need thereof.

7. A method for the treatment of drug addiction, comprising administering the compound of claim 1 or a pharmaceutically acceptable salt thereof to a patient in need thereof.

8. A method for the treatment of drug addiction, comprising administering the compound of claim 2 or a pharmaceutically acceptable salt thereof to a patient in need thereof.

9. A method for the treatment of drug addiction, comprising administering the compound of claim 3 or a pharmaceutically acceptable salt thereof to a patient in need thereof.

10. A method for the treatment of anxiety and stress disorder, comprising administering the compound of claim 1 or a pharmaceutically acceptable salt thereof to a patient in need thereof.

11. A method for the treatment of anxiety and stress disorder, comprising administering the compound of claim 2 or a pharmaceutically acceptable salt thereof to a patient in need thereof.

12. A method for the treatment of anxiety and stress disorder, comprising administering the compound of claim 3 or a pharmaceutically acceptable salt thereof to a patient in need thereof.

* * * * *